(12) United States Patent
Everett et al.

(10) Patent No.: US 9,746,481 B2
(45) Date of Patent: Aug. 29, 2017

(54) BIOMARKERS OF BRAIN INJURY

(75) Inventors: Allen Dale Everett, Glenwood, MD (US); James Francis Casella, Baltimore, MD (US); Jennifer Van Eyk, Los Angeles, CA (US)

(73) Assignee: The Johns Hopkins University, Baltimore, MD (US)

( * ) Notice: Subject to any disclaimer, the term of this patent is extended or adjusted under 35 U.S.C. 154(b) by 245 days.

(21) Appl. No.: 13/879,470

(22) PCT Filed: Oct. 14, 2011

(86) PCT No.: PCT/US2011/056338
§ 371 (c)(1),
(2), (4) Date: Oct. 18, 2013

(87) PCT Pub. No.: WO2012/051519
PCT Pub. Date: Apr. 19, 2012

(65) Prior Publication Data
US 2014/0045713 A1     Feb. 13, 2014

Related U.S. Application Data

(60) Provisional application No. 61/393,009, filed on Oct. 14, 2010, provisional application No. 61/436,956, filed on Jan. 27, 2011, provisional application No. 61/436,955, filed on Jan. 27, 2011.

(51) Int. Cl.
*C07K 16/18* (2006.01)
*A61B 5/1477* (2006.01)
*G01N 33/68* (2006.01)

(52) U.S. Cl.
CPC ......... *G01N 33/6896* (2013.01); *C07K 16/18* (2013.01); *G01N 2800/2871* (2013.01)

(58) Field of Classification Search
None
See application file for complete search history.

(56) References Cited

U.S. PATENT DOCUMENTS

| | | |
|---|---|---|
| 6,780,606 B1 | 8/2004 | Jackowski |
| 6,884,591 B2 | 4/2005 | Janigro et al. |
| 7,144,708 B2 | 12/2006 | Janigro et al. |
| 7,396,654 B2 | 7/2008 | Hayes |
| 7,427,490 B2 | 9/2008 | Valkirs |
| 7,456,027 B2 | 11/2008 | Wang et al. |
| 8,460,888 B2 | 6/2013 | Lafaye et al. |
| 8,492,107 B2 | 7/2013 | Wang et al. |
| 8,557,526 B2 | 10/2013 | Ottens et al. |
| 8,663,911 B2 | 3/2014 | Vojdani |
| 9,194,867 B2 | 11/2015 | Vojdani |
| 2003/0077590 A1 | 4/2003 | Pedersen et al. |
| 2003/0224460 A1 | 12/2003 | Pedersen et al. |
| 2006/0257943 A1 | 11/2006 | Dambinova |
| 2007/0098728 A1 | 5/2007 | Pedersen et al. |
| 2008/0026485 A1 | 1/2008 | Hueber et al. |
| 2008/0131881 A1* | 6/2008 | Ladenson ............ C12Q 1/6883 435/6.16 |
| 2008/0220013 A1 | 9/2008 | Hochstrasser et al. |
| 2009/0068691 A1 | 3/2009 | Dave et al. |
| 2011/0207126 A1 | 8/2011 | Popko et al. |
| 2013/0252834 A1* | 9/2013 | Dayon ............... G01N 33/6896 506/9 |
| 2014/0303041 A1 | 10/2014 | Hayes et al. |
| 2014/0342381 A1 | 11/2014 | Hayes |
| 2015/0118218 A1 | 4/2015 | Travis et al. |
| 2015/0119273 A1 | 4/2015 | Goldstein et al. |
| 2015/0141528 A1 | 5/2015 | Larner |
| 2015/0247867 A1 | 9/2015 | Curdt et al. |
| 2015/0268252 A1 | 9/2015 | Svetlov et al. |

FOREIGN PATENT DOCUMENTS

| | | |
|---|---|---|
| WO | 2006/012351 A2 | 2/2006 |
| WO | 2008/046509 A1 | 4/2008 |
| WO | WO2008046509 * | 4/2008 |
| WO | 2009/143519 A2 | 11/2009 |

(Continued)

OTHER PUBLICATIONS

Pelinka et al. Journal of Neurotrauma 21.11 (2004): 1553.*
Zetterberg et al.( Arch Neurol. 2006;63:1277-1280).*
Kobeissy et al., Mol and Cell Proteomics, 5.10:1887-1898, 2006.*
Wang et al (2008) MRI abnormalities of the brain in one-year-old children with sickle cell anemia. Pediatr Blood Cancer. Nov. 2008;51(5):643-6. doi: 10.1002/pbc.21612.
Pegelow et al (2008) Silent infarcts in children with sickle cell anemia and abnormal cerebral artery velocity. Arch Neurol. Dec. 2001;58(12):2017-21.
Vendt et al (2009) Silent Cerebral Infarct Transfusion (SIT) trial imaging core: application of novel imaging information technology for rapid and central review of MRI of the brain. J Digit Imaging. Jun. 2009;22(3):326-43. doi:10.1007/s10278-008-9114-3. Epub Apr. 9, 2008.
Ottens et al (2006) Neuroproteomics in neurotrauma. Mass Spectrom Rev. May-Jun. 2006;25(3):380-408.
Berger et al (2006) The Use of Biomarkers After Inflicted Traumatic Brain Injury: Insight into Etiology, Pathophysiology, and Biochemistry. Clin Ped Emer Med 7(3):186-193.

(Continued)

*Primary Examiner* — Kimberly A. Ballard
*Assistant Examiner* — Stacey N MacFarlane
(74) *Attorney, Agent, or Firm* — Melissa Hunter-Ensor; Leslie Serunian; Greenberg Traurig, LLP

(57) ABSTRACT

The present invention relates to the field of biomarkers. More specifically, the present invention relates to biomarkers useful in diagnosing brain injuries. Brain injury can include overt or traumatic brain injury, as well as subclinical brain injury (SCI). In one embodiment, a method for diagnosing SCI in a patient comprises (a) collecting a sample from the patient; (b) measuring the levels of a panel of biomarkers in the sample collected from the patient, wherein the panel of biomarkers comprises ASTN1, BAI3, CNDP1, ERMIN, GFAP, GRM3, KLH32, MAGE2, NRG3, NRGN, OMG, SLC39A12, RTN1, and MT3; and (c) comparing the levels of the panel of biomarkers with predefined levels of the same panel of biomarkers that correlate to a patient having SCI and predefined levels of the same panel of biomarkers that correlate to a patient not having SCI, wherein a correlation to one of the predefined levels provides the diagnosis.

4 Claims, 29 Drawing Sheets

(56) References Cited

FOREIGN PATENT DOCUMENTS

| WO | 2010/019553 A2 | 2/2010 |
|---|---|---|
| WO | 2011/032155 A2 | 3/2011 |
| WO | 2012/155134 A2 | 11/2012 |
| WO | 2015066211 A1 | 5/2015 |

OTHER PUBLICATIONS

Haqqani et al (2007) Biomarkers and diagnosis; protein biomarkers in serum of pediatric patients with severe traumatic brain injury identified by ICAT-LC-MS/MS. J Neurotrauma. Jan. 2007;24(1):54-74.

Hergenroeder et al (2008) Biomarkers in the clinical diagnosis and management of traumatic brain injury. Mol Diagn Ther. 2008;12(6):345-58. doi: 10.2165/1250444-200812060-00002.

Zetterberg, H., et al., "Neurochemical aftermath of amateur boxing", Arch Neurol. (2006) vol. 63, pp. 1277-1280.

Laterza, O., et al., "Biomarkers of tissue injury", Biomarkers Med. (2008) vol. 2, No. 1, pp. 81-92.

Extended European Search Report dated Feb. 10, 2014 for EP application 11833480.

Savage, W., et al., "Glial fibrillary acidic protein as a plasma biomarker of brain injury in children with sickle cell disease", American Journal of Hematology (2011) vol. 86, No. 5.

Williams, L., et al., "Proteomic-based approach for biomarker discovery to predict silent cerebral infarct in patients with sickle cell disease" (2009) 51st annual meeting of the american society of hematology, New Orleans, LA.

Hoshi, T., et al., "Relations of serum high-sensitivity c-reactive protein and interleukin-6 levels with silent brain infarction", Stroke (2005) vol. 36, No. 4.

Ishigami, A., et al., "Abnormal accumulation of citrullinated proteins catalyzed by peptidylarginine deiminase in hippocampal extracts from patients with alzheimer's disease" Journal of Neuroscience Research (2005) vol. 80, pp. 120-128.

Oguz, K., et al., Assessment of citrullinated myelin by 1H-MR spectroscopy in early-onset multiple sclerosis Am. J. Neuroradiol (2009) vol. 30, pp. 716-721.

Thorsell, A., et al., "Neurogranin in cerebrospinal fluid as a marker of synaptic degeneration in Alzheimer's disease" Brain Research (2010) vol. 1362, pp. 13-22.

Pak, J., et al., "Involvement of neurogranin in the modulation of calcium/calmodulin-dependent protein kinase II, synaptic plasticity, and spatial learning: a study with knockout mice", Proc. Natl. Acad. Sci. USA, Oct. 10, 2000, vol. 97, No. 21, pp. 11232-11237.

NCBI GeneBank Accession No. NP_006167 (Jan. 14, 2011).

Tok, J., et al., "Single microbead SELEX for efficient ssDNA aptamer generation against botulinum neurotoxin", Chem. Commun., Mar. 18, 2008, pp. 1883-1885.

Watson, J., et al., "Localization of RC3 (neurogranin) in rat brain subcellular fractions", Molecular Brain Research, Dec. 1, 1994, vol. 27, No. 2, pp. 323-328.

Neuner-Jehle, M., et al., "Sleep deprivation differentially alters the mRNA and protein levels of neurogranin in rat brain", Brain Research, Jul. 1, 1995, vol. 685, No. 1-2, pp. 143-153.

Clayton, D., et al., "Conservation and expression of IQ-domain-containing calpacitin gene products (neuromodulin/GAP-43, neurogranin/RC3) in the adult and developing oscine song control system", Developmental Neurobiology, Feb. 1, 2009, vol. 69, No. 2-3, pp. 124-140.

Laterza O. et al., "Identification of novel brain biomarkers", Clinical Chemistry, American Association for Clinical Chemistry, Washington, DC, Sep. 1, 2006, vol. 52, No. 9, pp. 1713-1721.

Hoehna, Y., et al., "Matrix metalloproteinase 9 regulates cell death following pilocarpine-induced seizures in the developing brain" Neurobiology of Disease (2012) vol. 48, pp. 339-347.

Koumura, A., et al., "Metallothionein-3 deficient mice exhibit abnormalities of psychological behaviors" Neuroscience Letters (2009) vol. 467, pp. 11-14.

European Search Report dated Oct. 9, 2015 for EP application 13760865.

Oliveira, C., et al., "Outcome biomarkers following severe traumatic brain injury" Rev Bras Ter Intensiva (2008) vol. 20, No. 4, pp. 411-421.

Radka, S., et al., "Presence of brain-derived neurotrophic factor in brain and human and rat but not mouse serum detected by a sensitive and specific immunoassay" Brain Research (1996) vol. 709, pp. 122-130.

Zhang, H., et al., "Methods for peptide and protein quantitation by liquid chromatography-multiple reaction monitoring mass spectrometry" Molecular & Cellular Proteomics (2011) pp. 1-62.

European Search Report dated Jul. 13, 2015 for EP application 12782967.

Wu, L., et al., "Characterization, using comparative proteomics, of differentially expressed proteins in the hippocampus of the mesial temporal lobe of epileptic rats following treatment with valproate" Amino Acids (2011) vol. 40, pp. 221-238.

Iliuk, A., et al., "Aptamer in Bioanalytical applications" Analytical Chemistry (2011) vol. 83, pp. 4440-4452.

Tang, L., et al., "Attenuation of opioid tolerance by antisense oligodeoxynucleotides targeting neurogranin" European Journal of Pharmacology (2006) vol. 542, pp. 106-107.

Tang, L., et al., "Disruption of acute opioid dependence by antisense oligodeoxynucleotides targeting neurogranin" Brain Research (2007) vol. 1143, pp. 78-82.

* cited by examiner

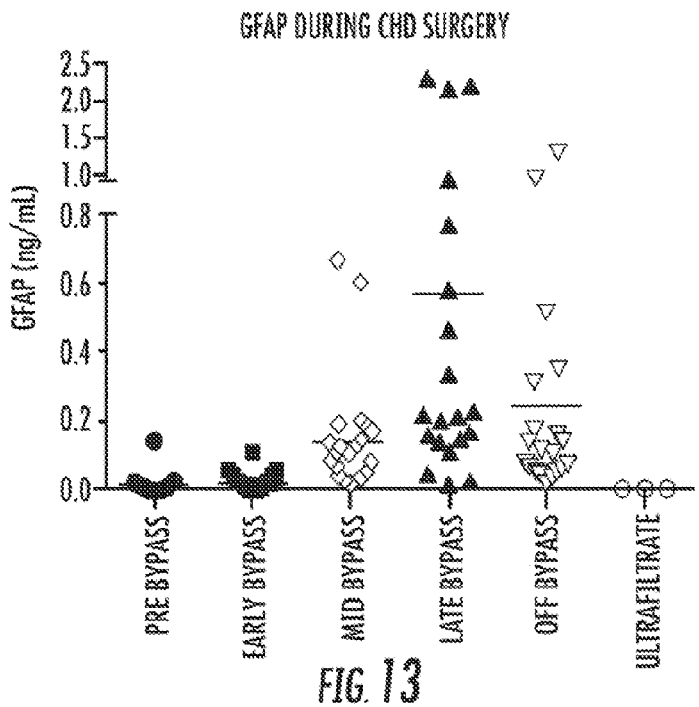

FIG. 13

| PATIENT CHARACTERISTICS | | ECMO COURSE CHARACTERISTICS | |
|---|---|---|---|
| Age, median (range) | 10 days (2 days to 16 yrs) | Primary indication for ECMO, NO. (%) | |
| Male, no. (%) | 12 (54.5) | Cardiac failure | 6 (27.3) |
| Race, no. (%) | | Respiratory failure | 12 (54.5) |
| Black | 12 (54.5) | Cardiac arrest/ECPR | 3 (13.6) |
| White | 7 (31.8) | Sepsis | 1 (4.6) |
| Other | 3 (13.6) | Mode of extracorporeal support, no. (%)a | |
| Hispanic, no. (%) | 2 (9.1) | VA ECMO | 17 (77.3) |
| Weight, kg, median (IQR) | 3.8 (3.1, 6.9) | VV ECMO | 3 (13.6) |
| Illness category, no (%) | | VV to VA ECMO | 2 (9.1) |
| Medical cardiac | 5 (22.7) | Complications on ECMO, NO. (%) | |
| Medical noncardiac | 14 (63.6) | Acute neurologic injury | 7 (31.8) |
| Surgical cardiac | 1 (4.6) | Intracranial hemorrhage | 5 (22.7) |
| Surgical noncardiac | 2 (9.1) | Severe cerebral edema | 1 (4.6) |
| PICU length of stay, median (IQR) | 15 days (8-23 days) | Brain death | 1 (4.6) |
| Hospital length of stay, median (IQR) | 30 days (19-53 days) | Pulmonary hemorrhage | 2 (9.1) |
| Mortality before PICU discharge, no. (%) | 7 (31.8) | Renal replacement therapy, no. (%) | 14 (63.6) |
| ECMO to ANI diagnosis, median (IQR) | 82 hrs (69-104 hrs) | Duration of ECMO support, median (IQR) | 114 hrs (86 hrs to 12 days) |

ECMO, extracorporeal membrane oxygenation; IQR, interquartile range; PICU, pediatric intensive care unit; ANI, acute neurologic injury; ECPR, extracorporeal cardiopulmonary resuscitation; VA, venoarterial; VV, venovenous aAll ECMO cannulations were performed through the right jugular vein and right carotid artery for VA ECMO and through the right jugular vein using a double-lumen cannula for VV ECMO. None of the patients enrolled in this study underwent direct intracardiac cannulation.

FIG. 14

| Patient No. | Primary Diagnosis | ECMO Indication | ECMO Duration | No. of GFAP Measurements | Peak GFAP | ANI Diagnosed During ECMO |
|---|---|---|---|---|---|---|
| 1 | Liver failure, CPA posttransplant | Cardiac Disease | 4 days | 5 | 5.86 | Unilateral IVH, intraparenchymal (basal ganglia, right temporal and occipital) hemorrhage, 2-cm midline shift, edema |
| 2 | Dilated cardiomyopathy | Cardiac Disease | 3 days | 4 | 20.5 | Frontoparietal 4 x 5 x 4-cm intraparenchymal hemorrhage, 2.5-cm midline shift, unilateral SDH, SAH, IVH |
| 3 | Dilated cardiomyopathy | Cardiac Disease | 5 days | 3 | 0.053 | No |
| 4 | PPHN | Respiratory Disease | 6 days | 4 | 0.164 | No |
| 5 | Septic shock | Sepsis | 1 day | 1 | 0[a] | No |
| 6 | PPHN | Respiratory Disease | 5 days | 8 | 0.088 | No |
| 7 | PPHN | Respiratory Disease | 4 days | 5 | 0.081 | No |
| 8 | Dilated Cardiomyopathy | Cardiac Disease | 1 day | 2 | 0.162 | No |
| 9 | PPHN | Respiratory Disease | 7 days | 7 | 0.062 | No |
| 10 | Critical aortic stenosis | Cardiac Disease | 12 days | 6 | 0.194 | No |
| 11 | PPHN | Respiratory Disease | 30 days | 16 | 1.43 | No |
| 12 | Diaphragmatic eventration | Respiratory Disease | 14 days | 11 | 0.398 | Unilateral cerebellar hemisphere, 1.5 x 2-cm intraparenchymal hemorrhage |
| 13 | TOF, Pulmonary atresia | ECPR | 4 days | 3 | 0.090 | No |
| 14 | Status asthmaticus | ECPR | 4 days | 2 | 44.9 | Rapid progression to brain death |
| 15 | PPHN | Respiratory Disease | 12 days | 3 | 0.795 | No |
| 16 | PPHN | Respiratory Disease | 15 days | 11 | 0.111 | Small SDH along the falx cerebri |
| 17 | PPHN | Respiratory Disease | 4 days | 3 | 0.155 | No |
| 18 | CDH | Respiratory Disease | 18 days | 13 | 0.400 | No |
| 19 | Truncus arteriosus | Cardiac Disease | 4 days | 2 | 0[a] | No |
| 20 | PPHN | Respiratory Disease | 3 days | 1 | 0[a] | Unilateral subependymal grade I IVH |
| 21 | CDH | Respiratory Disease | 17 days | 8 | 0[a] | No |
| 22 | Neonatal enterovirus sepsis | ECPR | 8 days | 8 | 14.6 | Severe diffuse cerebral edema |

ECMO, extracorporeal membrane oxygenation; GFAP, glial fibrillary acidic protein; ANI, acute neurologic injury; PCPC, Pediatric Cerebral Performance Category; PICU, pediatric intensive care unit; CPA, cardiopulmonary arrest; PPHN, persistent pulmonary hypertension of the newborn; TOF, tetralogy of Fallot; CDH, congenital diaphragmatic hernia; ECPR, extracorporeal cardiopulmonary resuscitation; IVH, intraventricular hemorrhage; SDH, subdural hemorrhage; SAH, subarachnoid hemorrhage; HCT, head computed tomography; HUS, head ultrasound; BD, brain death.

[a] Values below the lower limit of quantification (LLQ=0.040 ng/mL); [b] normal serial HUS during ECMO. Brain magnetic resonance imaging 6 weeks post-ECMO decannulation: few old intraventricular and intraparenchymal hemorrhagic foci; [c] normal serial HUS during ECMO. Brain magnetic resonance imaging 2 weeks post-ECMO decannulation: unilateral unilobar focal encephalomalacia consistent with prior ischemic event.

FIG. 15

| ANI Diagnostic Modality | ECMO to ANI Diagnosis | ECMO to GFAP >95th Percentile | Baseline PCPC | Discharge PCPC | Neurologic Outcome | PICU Survival |
|---|---|---|---|---|---|---|
| HCT | 104 hrs | 24 hrs | 1 | 6 | Poor | No |
| HUS | 11 hrs | 19 hrs | 2 | 6 | Poor | No |
| --- | --- | --- | 1 | 1 | Good | Yes |
| --- | --- | --- | 1 | 2 | Good | Yes |
| --- | --- | --- | 1 | 6 | Poor | No |
| --- | --- | --- | 2 | 2 | Good | Yes |
| --- | --- | --- | 1 | 1 | Good | Yes |
| --- | --- | --- | 1 | 1 | Good | Yes |
| --- | --- | --- | 1 | 2 | Good | Yes |
| --- | --- | --- | 1 | 1 | Good | Yes |
| --- | --- | 12 hrs[b] | 1 | 3 | Poor | Yes |
| HUS | 82 hrs | --- | 1 | 6 | Poor | No |
| --- | --- | --- | 1 | 2 | Good | Yes |
| BD examination | 64 hrs | 12 hrs | 1 | 6 | Poor | No |
| --- | --- | 10 days[c] | 1 | 2 | Good | Yes |
| HUS | 10 days | --- | 1 | 1 | Good | Yes |
| --- | --- | --- | 1 | 1 | Good | Yes |
| --- | --- | --- | 1 | 6 | Poor | No |
| --- | --- | --- | 1 | 1 | Good | Yes |
| HUS | 69 hrs | --- | 1 | 1 | Good | Yes |
| --- | --- | --- | 1 | 1 | Good | Yes |
| HUS | 2 hrs | 6 hrs | 3 | 6 | Poor | No |

*FIG. 15 (cont.)*

PEAK PLASMA GLIAL FIBRILLARY ACIDIC PROTEIN (GFAP) CONCENTRATIONS IN CHILDREN ON EXTRACORPOREAL MEMBRANE OXYGENATION WITH AND WITHOUT ACUTE NEUROLOGIC INJURY (n=22). PLEASE NOTE LOGARITHMIC SCALE ON Y-AXIS.

| TABLE 1 MATERNAL AND NEONATAL CHARACTERISTICS | | | |
|---|---|---|---|
| CHARACTERISTIC | COOLING (n=23) | COOLINGS (n=23) | P VALUE |
| MATERNAL AGE, y | 26.2±7.1 | 26.9±6.9 | .739 |
| MATERNAL RACE | | | .244 |
|    WHITE | 9 (39.1%) | 5 (21.7%) | |
|    BLACK | 11 (47.8%) | 17 (73.9%) | |
|    OTHER | 3 (13%) | 1 (4.3%) | |
| NULLIPAROUS | 14 (60.9%) | 8 (34.8%) | .078 |
| CESAREAN DELIVERY | 15 (65.2%) | 12 (52.2%) | .369 |
| TWIN GESTATION | 1 (4.3%) | 0 | 1.00 |
| PREECLAMPSIA | 3 (13%) | 3 (13%) | 1.00 |
| MAGNESIUM EXPOSURE | 1 (4.3%) | 3 (13%) | .608 |
| INTRAUTERINE GROWTH RESTRICTION | 4 (17.4%) | 2 (8.7%) | .665 |
| CLINICAL CHORIOAMNIONITIS | 3 (13%) | 4 (17.4%) | 1.00 |
| MECONIUM STAINING (MODERATE-THICK) | 6 (26.1%) | 7 (30.4%) | .743 |
| NONREASSURING FHR TRACING | 11 (47.8%) | 6 (21.6%) | .127 |
| ABRUPTION | 8 (34.8%) | 1 (4.3%) | .022[a] |
| BIRTHWEIGHT, g | 2978±630 | 3269±655 | .132 |
| UMBILICAL ARTERY pH | 6.92±0.19 | 7.14±0.13 | <.001[a] |
| UMBILICAL ARTERY BASE DEFICIT, mM | 15.5±6.7 | 7.8±5.9 | .001[a] |
| CORD pH <7.0 OR BASE DEFICIT>12 | 16/19 (84.2%) | 3/17 (17.6%) | <.001[a] |
| 5 MINUTE APGAR <7 | 21 (91.3%) | 6 (21.6%) | <.001[a] |
| RESPIRATORY DISTRESS | 11 (47.8%) | 16 (69.6%) | .134 |
| SEPSIS (PLUS BLOOD OR CSF CULTURE) | 1 (4.3%) | 1 (4.3%) | 1.00 |
| DEATH | 1 (4.3%) | 0 | 1.00 |
| NICU LENGTH OF STAY, d | 18.4±11.4 | 6.7±2.7 | <.001[a] |

MEANS AND SDS ARE PRESENTED FOR CONTINUOUS VARIABLES; COUNTS AND PERCENTAGES, ODDS, RATIOS, AND 95% CONFIDENCE INTERVALS ARE PRESENTED FOR CATEGORICAL VARIABLES.
CSF, CEREBROSPINAL FLUID; FHR, FETAL HEART RATE; HIE, HYPOXIC-ISCHEMIC ENCEPHALOPATHY; NICU, NEONATAL INTENSIVE CARE UNIT.

[a] STATISTICAL SIGNIFICANCE WITH P< .05.

*Ennen. Glial fibrillary acidic protein in hypoxic-ischemic encephalopathy. Am J Obstet Gynecol 2011.*

FIG. 18

| CHARACTERISTICS FOR NEONATES TREATED WITH COOLING | | | |
|---|---|---|---|
| CHARACTERISTIC | ABNORMAL MRI (n=8) | NORMAL MRI (n=15) | P VALUE |
| GESTATIONAL AGE, WKS | 37.9±1.3 | 39.0±1.4 | .073 |
| BIRTHWEIGHT, g | 2807±643 | 3069±625 | .353 |
| NULLIPAROUS | 6(75%) | 8(53.3%) | .400 |
| CESAREAN DELIVERY | 7(87.5%) | 8(53.3%) | .176 |
| IUGR | 0 | 4(26.7%) | .257 |
| CLINICAL CHORIOAMNIONITIS | 1(12.5%) | 2(13.3%) | 1.00 |
| NONREASSURING FHR TRACING | 5(62.5%) | 3(20%) | .400 |
| ABRUPTION | 6(75%) | 2(13.3%) | .006[a] |
| pH | 6.85±0.20 | 6.95±0.19 | .322 |
| BASE DEFICIT, mM | 19.6±4.3 | 13.8±6.9 | .104 |
| CORD pH <7.0 AND BASE DEFICIT >12 | 7/7(100%) | 9/12(75%) | .263 |

MEANS AND SDS ARE PRESENTED FOR CONTINUOUS VARIABLES; COUNTS AND PERCENTAGES ARE PRESENTED FOR CATEGORICAL VARIABLES. FHR, FETAL HEART RATE; HIE, HYPOXIC-ISCHEMIC ENCEPHALOPATHY; IUGR, INTRAUTERINE GROWTH RESTRICTION; MRI, MAGNETIC RESONANCE IMAGING.

[a] STATISTICAL SIGNIFICANCE WITH P<.05.

Ennen. Glial fibrillary acidic protein in hypoxic-ischemic encephalopathy. Am J Obstet Gynecol 2011.

FIG. 20

GFAP LEVELS AND NEUROLOGICAL OUTCOMES

| VARIABLE | n | AGE, d | GFAP ON NICU ADMISSION, ng/mL |
|---|---|---|---|
| ABNORMAL MRI (n=8) | | | |
| DEATH | 1 | 7 | .61 |
| G-TUBEFEEDING | 5 | 114±81 | 0.26±0.10 |
| FULL ORAL FEEDING | 2 | 17±9 | 0.04±0.06$^a$ |
| NORMAL MRI (n=15) | | | |
| DEATH | — | — | — |
| G-TUBEFEEDING | — | — | — |
| FULL ORAL FEEDING | 15 | 9±5 | 0.08±0.09 |

*GFAP, glial fibrillary acidic protein; HIE, HYPOXIC-ISCHEMIC ENCEPHALOPATHY; MRI, MAGNETIC RESONANCE IMAGING; NICU, intensive care unit.*

$^a P$ = .03 compared with normal MRI.

*Ennen. Glial fibrillary acidic protein in hypoxic-ischemic encephalopathy. AmJObstetGynecol 2011.*

FIG. 22

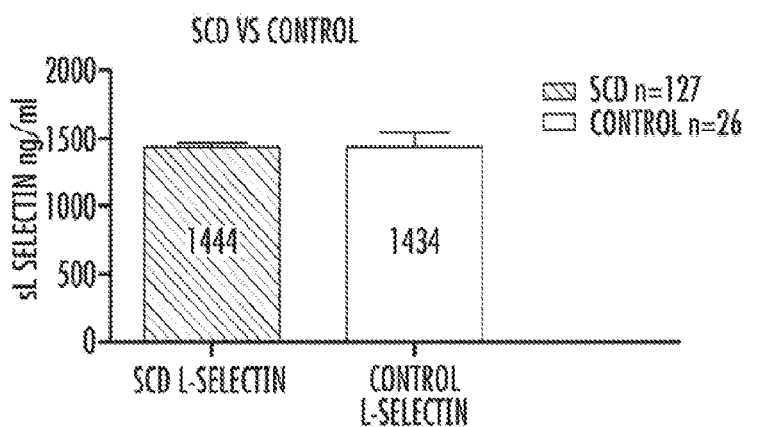
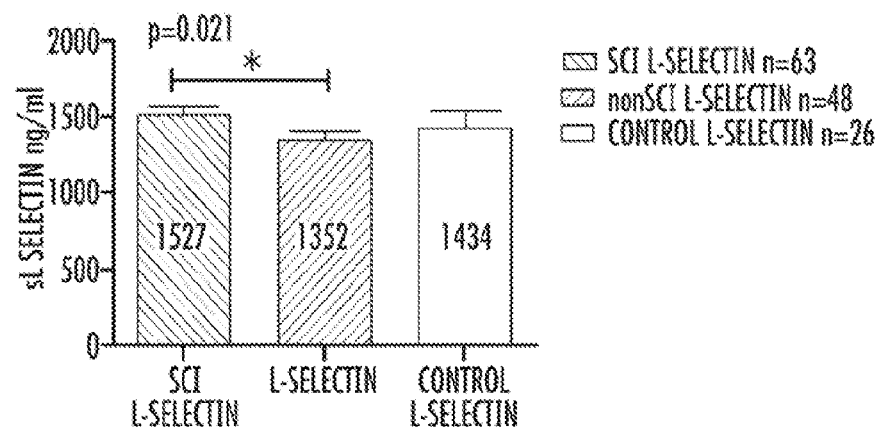
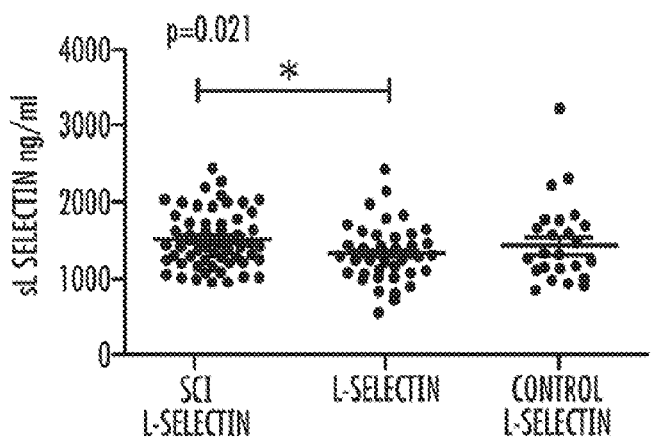
FIG. 27

BIOMARKERS OF BRAIN INJURY

CROSS-REFERENCE TO RELATED APPLICATIONS

This application is a 35 U.S.C. §371 U.S. national entry of International Application PCT/US2011/056338 having an international filing date of Oct. 14, 2011, which claims the benefit of U.S. Provisional Application No. 61/436,956 filed Jan. 27, 2011, U.S. Provisional Application No. 61/436,955 filed Jan. 27, 2011 and U.S. Provisional Application 61/393,009 filed Oct. 14, 2010, the contents of each of the aforementioned applications are herein incorporated by reference in their entireties.

STATEMENT OF GOVERNMENTAL INTEREST

This invention was made with U.S. government support under grant no. NHLBI 1 R01 HL091759-02, and NHLBI 5U54HL090515-02. The U.S. government has certain rights in the invention.

FIELD OF THE INVENTION

The present invention relates to the field of biomarkers. More specifically, the present invention relates to biomarkers useful in diagnosing brain injuries.

INCORPORATION-BY-REFERENCE OF MATERIAL SUBMITTED ELECTRONICALLY

This application contains a sequence listing. It has been submitted electronically via EFS-Web as an ASCII text file entitled "P10784-08_Sequence_Listing-ST25.txt." The sequence listing is 1,947 bytes in size, and was created on Oct. 13, 2011. It is hereby incorporated by reference in its entirety.

BACKGROUND OF THE INVENTION

Brain injuries are complex and can have multiple severe clinical outcomes. Injury of the brain and spinal cord can result from head trauma, stroke, traumatic birth, heart surgery, cardiac arrest and patients requiring cardiovascular support with ventricular assist devices or extracorporeal membrane oxygenation (ECMO). Moreover, detection of subclinical brain injury is difficult, especially in children and neonates with birth-related injury. Children with sickle cell disease are at high risk for subclinical brain injury. Untreated subclinical brain injuries in children can progress to overt stroke, neurological damage, learning problems and memory loss.

Unfortunately, clinical tools such as physical exam, and imaging (CT Scan or MRI) are subjective, not widely available, not sensitive or specific enough and or too costly to identify the infant, child or adult with brain injury. There is a great clinical need to identify patients with brain injury and especially subclinical injury because these infants, children and adults are at significant risk of progressing to overt stroke and development of cognitive and motor loss, and dementia.

SUMMARY OF THE INVENTION

The present invention is based, at least in part, on the discovery of central nervous system (CNS)-specific protein biomarkers circulating in body fluids after brain and CNS injury. Release or secretion of proteins from cells of the CNS can be useful for diagnostic/prognostic assessment of patient viability, recovery and the effects of therapy to stabilize or prevent new or recurrent CNS injury in children and adults. Thus, detection of circulating CNS proteins improves the diagnostic accuracy of CNS injury by identifying children and adults with subclinical and overt brain injury and provides the means to determine and validate new and existing CNS injury treatments for efficacy to improve outcomes. This would also provide a means for screening new protocols or drugs (interventions) for reduced injury.

Accordingly, in one aspect, the present invention provides biomarkers useful for diagnosing children and adults with brain injury. In one embodiment, the brain injury is subclinical brain injury (SCI). In another embodiment, brain injury is overt brain injury. The biomarkers can be used to diagnose patients, assess a patient's prognosis over time, or generally determine a patient's brain injury status.

In particular embodiments, a method for diagnosing brain injury in a patient comprises the steps of (a) collecting a sample from the patient; (b) measuring the levels of one or more biomarkers in the sample collected from the patient; and (c) comparing the levels of the one or more biomarkers with predefined levels of the same biomarkers that correlate to a patient having brain injury and predefined levels of the same biomarkers that correlate to a patient not having brain injury, wherein a correlation to one of the predefined levels provides the diagnosis.

In more specific embodiments, a method for diagnosing subclinical brain injury (SCI) in a patient comprises the steps of (a) collecting a sample from the patient; (b) measuring the levels of one or more biomarkers in the sample collected from the patient; and (c) comparing the levels of the one or more biomarkers with predefined levels of the same biomarkers that correlate to a patient having SCI and predefined levels of the same biomarkers that correlate to a patient not having SCI, wherein a correlation to one of the predefined levels provides the diagnosis.

The one or more biomarkers can be selected from the group consisting of astrotactin 1 (ASTN1), brain angiogenesis inhibitor 3 (BAI3); carnosine dipeptidase 1 (CNDP1); ERMIN; glial fibrillary acidic protein (GFAP); glutamate receptor metabotropic 3 (GRM3); kelch-like protein 32 (KLH32); melanoma antigen family E,2 (MAGE2); neuregulin 3 (NRG3); neurogranin (NRGN); oligodendrocyte myelin glycoprotein (OMG); solute carrier family 39 (zinc transporter), member 12 (SLC39A12); reticulon 1 (RTN1); and metallothionein (MT3).

In a specific embodiment, the one or more biomarkers comprises NRGN. In another embodiment, the one or more biomarkers comprises OMG. In yet another embodiment, the one or more biomarkers comprises MT3. In a further embodiment, the one or more biomarkers further comprises GFAP.

In another embodiment, the one or more biomarkers comprise NRGN, OMG, and MT3. The biomarkers can further comprise GFAP. In yet another embodiment, the one or more biomarkers further comprise the biomarkers listed in Table 1 and Table 2.

In another embodiment, a method for diagnosing brain injury in a patient comprises the steps of (a) collecting a sample from the patient; (b) measuring the levels of a panel of biomarkers in the sample collected from the patient, wherein the panel of biomarkers comprises ASTN1, BAI3, CNDP1, ERMIN, GFAP, GRM3, KLH32, MAGE2, NRG3, NRGN, OMG, SLC39A12, RTN1, and MT3; and (c) comparing the levels of the panel of biomarkers with predefined levels of the same panel of biomarkers that correlate to a patient having brain injury and predefined levels of the same panel of biomarkers that correlate to a patient not having brain injury, wherein a correlation to one of the predefined levels provides the diagnosis.

In yet another embodiment, a method for diagnosing SCI in a patient comprises the steps of (a) collecting a sample from the patient; (b) measuring the levels of a panel of biomarkers in the sample collected from the patient, wherein the panel of biomarkers comprises ASTN1, BAI3, CNDP1, ERMIN, GFAP, GRM3, KLH32, MAGE2, NRG3, NRGN, OMG, SLC39A12, RTN1, and MT3; and (c) comparing the levels of the panel of biomarkers with predefined levels of the same panel of biomarkers that correlate to a patient having SCI and predefined levels of the same panel of biomarkers that correlate to a patient not having SCI, wherein a correlation to one of the predefined levels provides the diagnosis.

In an alternative embodiment, a method for diagnosing brain injury in a patient comprises the steps of (a) collecting a sample from the patient; (b) measuring the levels of a panel of biomarkers in the sample collected from the patient, wherein the panel of biomarkers comprises NRGN and GFAP; and (c) comparing the levels of the panel of biomarkers with predefined levels of the same biomarkers that correlate to a patient having brain injury and predefined levels of the same biomarkers that correlate to a patient not having brain injury, wherein a correlation to one of the predefined levels provides the diagnosis. In a more specific embodiment, the panel of biomarkers further comprises OMG, and MT3. In a further embodiment, the panel of biomarkers further comprises ASTN1, BAI3, CNDP1, ERMIN, GRM3, KLH32, MAGE2, NRG3, OMG, SLC39A12, RTN1, and MT3.

In a further embodiment, a method for diagnosing SCI in a patient comprises the steps of (a) collecting a sample from the patient; (b) measuring the levels of a panel of biomarkers in the sample collected from the patient, wherein the panel of biomarkers comprises NRGN and GFAP; and (c) comparing the levels of the panel of biomarkers with predefined levels of the same biomarkers that correlate to a patient having SCI and predefined levels of the same biomarkers that correlate to a patient not having SCI, wherein a correlation to one of the predefined levels provides the diagnosis. In a more specific embodiment, the panel of biomarkers further comprises OMG, and MT3. In a further embodiment, the panel of biomarkers further comprises ASTN1, BAI3, CNDP1, ERMIN, GRM3, KLH32, MAGE2, NRG3, OMG, SLC39A12, RTN1, and MT3.

In another embodiment, a method for diagnosing brain injury in a patient comprises the steps of (a) collecting a plasma sample from the patient; (b) measuring the levels of a panel of biomarkers in the plasma sample collected from the patient, wherein the panel of biomarkers comprises NRGN and GFAP; and (c) comparing the levels of the panel of biomarkers with predefined levels of the same biomarkers that correlate to a patient having brain injury and predefined levels of the same biomarkers that correlate to a patient not having brain injury, wherein a correlation to one of the predefined levels provides the diagnosis. In a more specific embodiment, the panel of biomarkers further comprises OMG, and MT3. Alternatively, the panel of biomarkers further comprises ASTN1, BAI3, CNDP1, ERMIN, GRM3, KLH32, MAGE2, NRG3, OMG, SLC39A12, RTN1, and MT3.

In yet another embodiment, a method for diagnosing SCI in a patient comprises the steps of (a) collecting a plasma sample from the patient; (b) measuring the levels of a panel of biomarkers in the plasma sample collected from the patient, wherein the panel of biomarkers comprises NRGN and GFAP; and (c) comparing the levels of the panel of biomarkers with predefined levels of the same biomarkers that correlate to a patient having SCI and predefined levels of the same biomarkers that correlate to a patient not having SCI, wherein a correlation to one of the predefined levels provides the diagnosis. In a more specific embodiment, the panel of biomarkers further comprises OMG, and MT3. Alternatively, the panel of biomarkers further comprises ASTN1, BAI3, CNDP1, ERMIN, GRM3, KLH32, MAGE2, NRG3, OMG, SLC39A12, RTN1, and MT3.

In another embodiment of the present invention, a method for determining the brain injury status in a patient comprises the steps of (a) collecting a sample from the patient; (b) measuring the levels of a panel of biomarkers in the sample collected from the patient, wherein the panel of biomarkers comprises ASTN1, BAI3, CNDP1, ERMIN, GFAP, GRM3, KLH32, MAGE2, NRG3, NRGN, OMG, SLC39A12, RTN1, and MT3; and (c) comparing the levels of the panel of biomarkers with predefined levels of the same panel of biomarkers that correlate to one or more brain injury statuses selected from the group consisting of having brain injury, not having brain injury, progressing brain injury, and regressing brain injury, wherein a correlation to one of the predefined levels determines the brain injury status of the patient.

In particular embodiments of the present invention, a method for determining the SCI status in a patient comprises the steps of (a) collecting a sample from the patient; (b) measuring the levels of a panel of biomarkers in the sample collected from the patient, wherein the panel of biomarkers comprises ASTN1, BAI3, CNDP1, ERMIN, GFAP, GRM3, KLH32, MAGE2, NRG3, NRGN, OMG, SLC39A12, RTN1, and MT3; and (c) comparing the levels of the panel of biomarkers with predefined levels of the same panel of biomarkers that correlate to one or more SCI statuses selected from the group consisting of having SCI, not having SCI, progressing SCI, and regressing SCI, wherein a correlation to one of the predefined levels determines the SCI status of the patient.

In particular embodiments of the present invention, the measuring step comprises immunoassay, immunoblotting method, immunoprecipitation assay, immunostaining method, quantitative assay, immunofluorescent assay, or a chemiluminescence assay. In certain embodiments, the sample is a blood, plasma serum, cerebrospinal fluid (CSF), or urine sample. In a specific embodiment, the sample is a blood sample. In a more specific embodiment, the sample is a serum sample.

In another aspect, the present invention provides kits for determining brain injury status in a patient. In particular embodiments, the diagnostic kit comprises a substrate for collecting a biological sample from the patient; and means for measuring the levels of one or more biomarkers selected from the group consisting of ASTN1, BAI3, CNDP1, ERMIN, GFAP, GRM3, KLH32, MAGE2, NRG3, NRGN, OMG, SLC39A12, RTN1, and MT3.

BRIEF DESCRIPTION OF THE FIGURES

FIG. 13 is a graph showing GFAP levels during cardiopulmonary bypass for repair of congenital heart disease.

FIG. 14 is table showing demographic and clinical characteristics of the 22 evaluated patients.

FIG. 15 is a table showing individual patient characteristics and outcomes.

FIG. 18 is a table summarizing the maternal and neonatal characteristics of the study population.

FIG. 20 is a table showing the characteristics for neonates treating with cooling.

FIG. 22 is table showing GFAP levels and neurological outcomes.

FIG. 27 shows SELL concentration (mean) by ELISA in SCI and non-SCI SCD children and age and race matched controls (top). The same data is shown in bar graph format (middle) and spot graph format with mean (bottom).

DETAILED DESCRIPTION OF THE INVENTION

Figure 1:
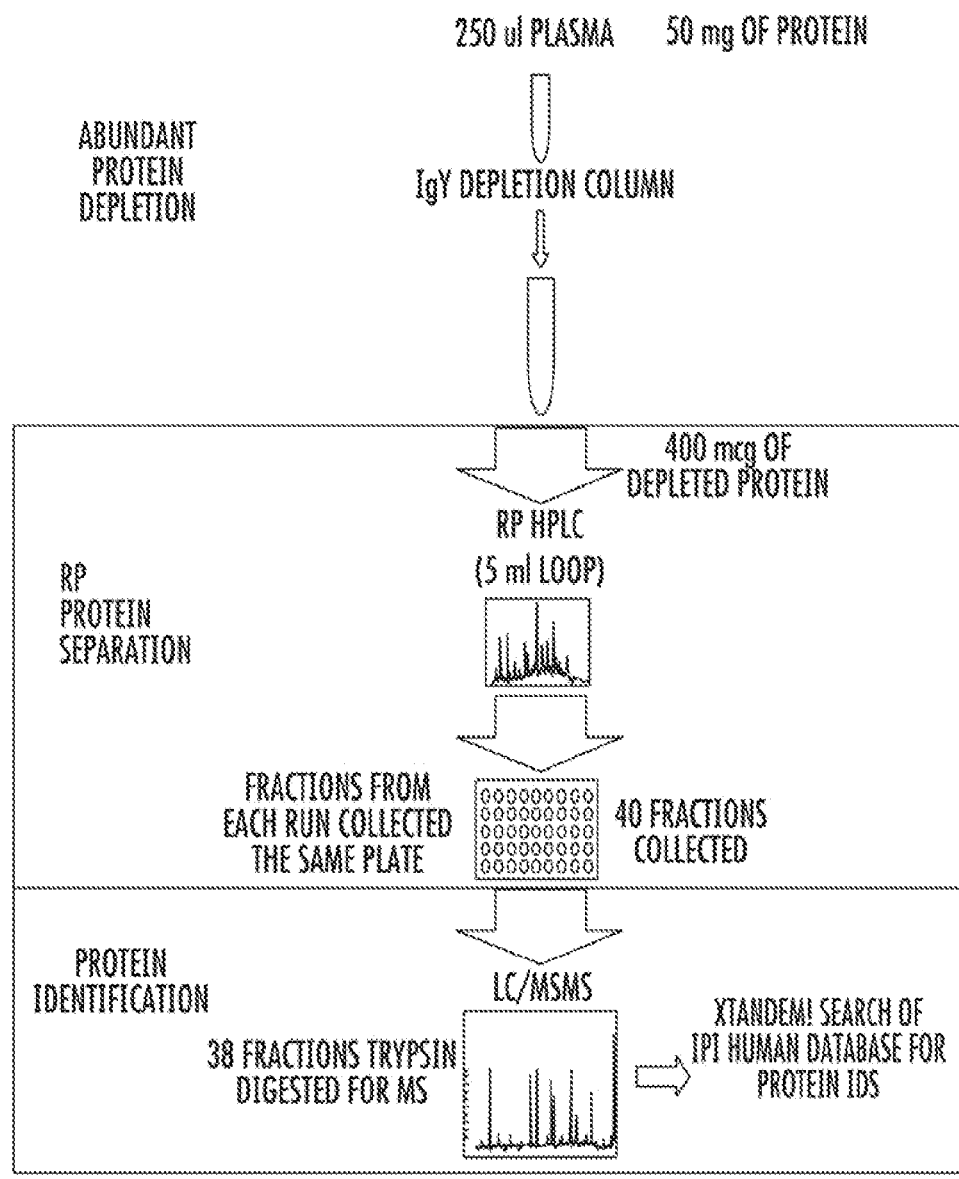
FIG. 1 is an overview of the approach for plasma depletion, RP-HPLC separation and MS analysis.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The term "brain injury" refers to a condition in which the brain is damaged by injury caused by an event. As used herein, an "injury" is an alteration in cellular or molecular integrity, activity, level, robustness, state, or other alteration that is traceable to an event. For example, an injury includes a physical, mechanical, chemical, biological, functional, infectious, or other modulator of cellular or molecular characteristics. An event can include a physical trauma such as an impact (percussive) or a biological abnormality such as a stroke resulting from either blockade or leakage of a blood vessel. An event is optionally an infection by an infectious agent. A person of skill in the art recognizes numerous equivalent events that are encompassed by the terms injury or event.

More specifically, the term "brain injury" refers to a condition that results in central nervous system damage, irrespective of its pathophysiological basis. Among the most frequent origins of a "brain injury" are stroke and traumatic brain injury (TBI). A "stroke" is classified into hemorrhagic and non-hemorrhagic. Examples of hemorrhagic stroke include cerebral hemorrhage, subarachnoid hemorrhage, and intracranial hemorrhage secondary to cerebral arterial malformation, while examples of non-hemorrhagic stroke include cerebral infarction.

The term "traumatic brain injury" or "TBI" refer to traumatic injuries to the brain which occur when physical trauma causes brain damage. For example, TBI can result from a closed head injury or a penetrating head injury. A "non-traumatic brain injury" refers to brain injuries that do not involve ischemia or external mechanical force (e.g., stroke, Alzheimer's disease, Parkinson's disease, Huntington's disease, multiple sclerosis, amyotrophic lateral sclerosis, brain hemorrhage, brain infections, brain tumor, among others).

The term "brain injury" also refers to subclinical brain injury, spinal cord injury, and anoxic-ischemic brain injury. The term "subclinical brain injury" (SCI) refers to brain injury without overt clinical evidence of brain injury. A lack of clinical evidence of brain injury when brain injury actually exists could result from degree of injury, type of injury, level of consciousness, medications particularly sedation and anesthesia.

The "spinal cord injury" refers to a condition in which the spinal cord receives compression/detrition due to a vertebral fracture or dislocation to cause dysfunction. As used herein, the term "anoxic-ischemic brain injury" refers to deprivation of oxygen supply to brain tissue resulting in compromised brain function and includes cerebral hypoxia. For example, anoxic-ischemic brain injury includes focal cerebral ischemia, global cerebral ischemia, hypoxic hypoxia (i.e., limited oxygen in the environment causes reduced brain function, such as with divers, aviators, mountain climbers, and fire fighters, all of whom are at risk for this kind of cerebral hypoxia), obstructions in the lungs (e.g., hypoxia resulting from choking, strangulation, the crushing of the windpipe).

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels that correspond to, for example, a patient having subclinical brain injury (SCI), not having SCI, is responding to treatment for SCI, is not responding to treatment for SCI, is/is not likely to respond to a particular SCI treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels of the same biomarkers in a control sample (e.g., predefined levels that correlate to uninfected individuals, standard SCI levels, etc.).

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has SCI. In specific embodiments, the parameter may comprise the level of one or more biomarkers of the present invention. A particular set or pattern of the amounts of one or more biomarkers may indicate that a patient has SCI (i.e., correlates to a patient having SCI). In other embodiments, a particular set or pattern of the amounts of one or more biomarkers may be correlated to a patient being unaffected (i.e., indicates a patient does not have SCI). In certain embodiments, "indicating," or "correlating," as used according to the present invention, may be by any linear or non-linear method of quantifying the relationship between levels of biomarkers to a standard, control or comparative value for the assessment of the diagnosis, prediction of SCI or SCI progression, assessment of efficacy of clinical treatment, identification of a patient that may respond to a particular treatment regime or pharmaceutical agent, monitoring of the progress of treatment, and in the context of a screening assay, for the identification of an anti-SCI therapeutic.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of SCI. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a serum sample is used. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., an SCI treatment) on a patient. In yet another embodiment, a transcription rate, mRNA level, translation rate, protein level, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, etc. A "suitable control" can be a profile or pattern of levels of one or more biomarkers of the present invention that correlates to SCI, to which a patient sample can be compared. The patient sample can also be compared to a negative control, i.e., a profile that correlates to not having SCI.

II. Detection of Brain Injury Biomarkers

A. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer, hybrids or combinations of the foregoing, and the like. In a specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein. In another embodiment, the mass spectrometric technique is multiple reaction monitoring (MRM) or quantitative MRM.

In an alternative embodiment, the mass spectrometric technique comprises surface enhanced laser desorption and ionization or "SELDI," as described, for example, in U.S. Pat. No. 6,225,047 and U.S. Pat. No. 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

B. Detection by Immunoassay

In other embodiments, the biomarkers of the present invention can be detected and/or measured by immunoassay. Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds all neurogranin and/or one or more of its breakdown products might be used. Aptamers are nucleic acid-based molecules that bind specific ligands. Methods for making aptamers with a particular binding specificity are known as detailed in U.S. Pat. No. 5,475,096; U.S. Pat. No. 5,670,637; U.S. Pat. No. 5,696,249; U.S. Pat. No. 5,270,163; U.S. Pat. No. 5,707,796; U.S. Pat. No. 5,595,877; U.S. Pat. No. 5,660,985; U.S. Pat. No. 5,567,588; U.S. Pat. No. 5,683,867; U.S. Pat. No. 5,637,459; and U.S. Pat. No. 6,011,020.

C. Detection by Electrochemicaluminescent Assay

In several embodiments, the biomarker biomarkers of the present invention may be detected by means of an electrochemicaluminescent assay developed by Meso Scale Discovery (Gaithersburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. No. 7,497,997; U.S. Pat. No. 7,491,540; U.S. Pat. No. 7,288,410; U.S. Pat. No. 7,036,946; U.S. Pat. No. 7,052,861; U.S. Pat. No. 6,977,722; U.S. Pat. No. 6,919,173; U.S. Pat. No. 6,673,533; U.S. Pat. No. 6,413,783; U.S. Pat. No. 6,362,011; U.S. Pat. No. 6,319,670; U.S. Pat. No. 6,207,369; U.S. Pat. No. 6,140,045; U.S. Pat. No. 6,090,545; and U.S. Pat. No. 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. No. 6,537,749; U.S. Pat. No. 6,329,209; U.S. Pat. No. 6,225,047; U.S. Pat. No. 5,242,828; PCT International Publication No. WO 00/56934; and PCT International Publication No. WO 03/048768.

III. Determination of a Patient's Brain Injury Status

The present invention relates to the use of biomarkers to diagnose brain injury. More specifically, the biomarkers of the present invention can be used in diagnostic tests to determine, qualify, and/or assess brain injury status, for example, to diagnose brain injury, in an individual, subject or patient. In particular embodiments, brain injury status can include determining a patient's subclinical brain injury status or SCI status, for example, to diagnose SCI, in an individual, subject or patient. More specifically, the biomarkers to be detected in diagnosing brain injury (e.g., SCI or overt brain injury) include, but are not limited to, ASTN1, BAI3, CNDP1, ERMIN, GFAP, GRM3, KLH32, MAGE2, NRG3, NRGN, OMG, SLC39A12, RTN1, and MT3. Other biomarkers known in the relevant art may be used in combination with the biomarkers described herein including, but not limited to, SBDP150, SBDP150i, NSE, S1OOβ, MAP2, MAPI, MAP3, MAP4, MAP5, MBP, Tau, NF-L, NF-M, NF-H, UCH-L1, NSE, NeuN, CNPase, α-internexin, CB-I, CB-2; ICAM, VAM, NCAM, NL-CAM, AL-CAM, C-CAM; synaptotagmin, synaptophysin, synapsin, SNAP; CRMP-2, CRMP-I, CRMP-3, CRMP-4 iNOS, and β111-tubulin.

A. Biomarker Panels

The biomarkers of the present invention can be used in diagnostic tests to assess, determine, and/or qualify (used interchangeably herein) brain injury status in a patient. The phrase "brain injury status" includes any distinguishable manifestation of the condition, including not having brain injury. For example, brain injury status includes, without limitation, the presence or absence of brain injury in a patient, the risk of developing brain injury, the stage or severity of brain injury, the progress of brain injury (e.g., progress of brain injury over time) and the effectiveness or response to treatment of brain injury (e.g., clinical follow up and surveillance of brain injury after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different SCI statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially present in UI (NC or non-brain injury) and brain injury and, therefore, are useful in aiding in the determination of brain injury status. In certain embodiments, the biomarkers are measured in a patient sample using the methods described herein and compared, for example, to predefined biomarker levels and correlated to brain injury status. In particular embodiments, the measurement(s) may then be compared with a relevant diagnostic amount(s), cut-off(s), or multivariate model scores that distinguish a positive brain injury status from a negative brain injury status. The diagnostic amount(s) represents a measured amount of a biomarker(s) above which or below which a patient is classified as having a particular brain injury status. For example, if the biomarker(s) is/are up-regulated compared to normal during brain injury, then a measured amount(s) above the diagnostic cutoff(s) provides a diagnosis of brain injury. Alternatively, if the biomarker(s) is/are down-regulated during brain injury, then a measured amount(s) at or below the diagnostic cutoff(s) provides a diagnosis of non-brain injury. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different brain injury statuses, and drawing the cut-off to suit the desired levels of specificity and sensitivity.

Indeed, as the skilled artisan will appreciate there are many ways to use the measurements of two or more biomarkers in order to improve the diagnostic question under investigation. In a quite simple, but nonetheless often effective approach, a positive result is assumed if a sample is positive for at least one of the markers investigated.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose brain injury, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Developing Brain Injury

In a specific embodiment, the present invention provides methods for determining the risk of developing brain injury in a patient. Biomarker percentages, amounts or patterns are characteristic of various risk states, e.g., high, medium or low. The risk of developing brain injury is determined by measuring the relevant biomarkers and then either submitting them to a classification algorithm or comparing them with a reference amount, i.e., a predefined level or pattern of biomarkers that is associated with the particular risk level.

C. Determining Brain Injury Severity

In another embodiment, the present invention provides methods for determining the severity of brain injury in a patient. Each grade or stage of brain injury likely has a characteristic level of a biomarker or relative levels of a set of biomarkers (a pattern). The severity of brain injury is determined by measuring the relevant biomarkers and then either submitting them to a classification algorithm or comparing them with a reference amount, i.e., a predefined level or pattern of biomarkers that is associated with the particular stage.

D. Determining Brain Injury Prognosis

In one embodiment, the present invention provides methods for determining the course of brain injury in a patient. brain injury course refers to changes in brain injury status over time, including brain injury progression (worsening) and brain injury regression (improvement). Over time, the amount or relative amount (e.g., the pattern) of the biomarkers changes. For example, biomarker "X" may be increased with brain injury, while biomarker "Y" may be decreased with brain injury. Therefore, the trend of these biomarkers, either increased or decreased over time toward brain injury or non-brain injury indicates the course of the condition. Accordingly, this method involves measuring the level of one or more biomarkers in a patient at least two different time points, e.g., a first time and a second time, and comparing the change, if any. The course of brain injury is determined based on these comparisons.

E. Patient Management

In certain embodiments of the methods of qualifying brain injury status, the methods further comprise managing patient treatment based on the status. Such management includes the actions of the physician or clinician subsequent to determining brain injury status. For example, if a physician makes a diagnosis of brain injury, then a certain regime of monitoring would follow. An assessment of the course of brain injury using the methods of the present invention may then require a certain brain injury therapy regimen. Alternatively, a diagnosis of non-brain injury might be followed with further testing to determine a specific disease that the patient might be suffering from. Also, further tests may be called for if the diagnostic test gives an inconclusive result on brain injury status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of one or more of the biomarkers of the present invention may change toward a non-brain injury profile. Therefore, one can follow the course of one or more biomarkers in the patient during the course of treatment. Accordingly, this method involves measuring one or more biomarkers in a patient receiving drug therapy, and correlating the biomarker levels with the brain injury status of the patient (e.g., by comparison to predefined levels of the biomarkers that correspond to different brain injury statuses). One embodiment of this method involves determining the levels of one or more biomarkers at at least two different time points during a course of drug therapy, e.g., a first time and a second time, and comparing the change in levels of the biomarkers, if any. For example, the levels of one or more biomarkers can be measured before and after drug administration or at two different time points during drug administration. The effect of therapy is determined based on these comparisons. If a treatment is effective, then the one or more biomarkers will trend toward normal, while if treatment is ineffective, the one or more biomarkers will trend toward brain injury indications.

G. Generation of Classification Algorithms for Qualifying Brain Injury Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data.

Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

H. Kits for the Detection of Brain Injury Biomarkers

In another aspect, the present invention provides kits for qualifying brain injury status, which kits are used to detect the biomarkers described herein. In a specific embodiment, the kit is provided as an ELISA kit comprising antibodies to the biomarkers of the present invention including, but not limited to, ASTN1, BAI3, CNDP1, ERMIN, GFAP, GRM3, KLH32, MAGE2, NRG3, NRGN, OMG, SLC39A12, RTN1, and MT3.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit for qualifying brain injury status may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding blood or blood serum from the patient to the kit and detecting the relevant biomarkers conjugated with antibodies, specifically, by a method which comprises the steps of: (i) collecting blood or blood serum from the patient; (ii) separating blood serum from the patient's blood; (iii) adding the blood serum from patient to a diagnostic kit; and, (iv) detecting the biomarkers conjugated with antibodies. In this method, the antibodies are brought into contact with the patient's blood. If the biomarkers are present in the sample, the antibodies will bind to the sample, or a portion thereof. In other kit and diagnostic embodiments, blood or blood serum need not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Discovery of Circulation Biomarkers of Subclinical Brain Injury (SCI) in Children with Sickle Cell Disease (SCD)

Children with SCD and SCI have significant learning defects and are at increased risk for stroke. Early detection of SCI would allow institution of therapies to prevent further brain injury and neurocognitive defects, including loss of I.Q. By definition, SCI patients have MRI and pathologic evidence of brain injury consistent with microinfarction. Therefore, it is likely that unique circulating biomarkers exist to identify patients with SCI as has been shown in non-SCD patients with overt stroke. The present goal of is to use non-biased proteomic techniques to explore clinically paired groups of SCI and non-SCI patient plasma samples to identify lead proteins for validation as circulating biomarkers of SCI.

Study Population.

The study population comprised male and female children 6-12 years old with SCD participating in the SIT Trial (24 institutions) having an adjudicated MRI with (SCI group) or without (non-SCI group) evidence of SCI. As part of the SIT Trial, in addition to an MRI and neurologic exam, patients have CBC, Hb/Hct, hemoglobin electrophoresis and other clinical studies determined. At entry into the trial, citrated plasma is prepared, frozen and stored in the Biologic Repository at Johns Hopkins at −70° C. The initial discovery cohort for this Example, as described in Table 1, includes 50 patients with SCI and 50 patients without SCI, all with an Hb<8.1 g/dL, as this has been shown to be an independent risk factor for SCI.

Depletion of Abundant Proteins.

To identify proteins with altered plasma expression in children with SCI, 250 µl aliquots of individual plasma samples from SCI and non-SCI children were affinity depleted using a new generation of the previously available LC10 polyclonal antibody affinity column (IgY high capacity LC10 column, Beckman-Coulter). This new generation column doubles the amount of plasma that can be depleted (from 125 to 250 µl), thereby increasing downstream sensitivity. This new column is coupled to the ProteomeLab PPS Proteome Partitioning System (Beckman-Coulter) for flow through and bound protein collection. For each 250 µl of plasma depleted, 7 ml of flow through protein is collected. Using a 5 ml loop, 400 µg of depleted protein was fractionated by RP HPLC (ProteomeLab PPS Proteome Partitioning System) coupled to a $C_{18}$ non-porous column, using a linear acetonitrile gradient, with 60 fractions collected over 30 minutes.

Identification and Quantification of Small and Low Abundant Plasma Proteins in SCI.

To identify the proteins contained in the RP HPLC fractions described above, LC/MS/MS (LTQ Orbitrap) analysis of each RP HPLC fraction was used to develop a non-SCI/SCI plasma protein database. Briefly, the pooled RP HPLC fractions from a single patient were completely dried using a SpeedVac, resuspended in neutralization buffer and trypsin digested overnight. After trypsin digestion, the RP HPLC fractions were analyzed by LC/MS/MS (Thermo LTQ-Orbitrap). RP HPLC fraction of intact proteins before trypsin digestion resulted in fractions contains 50-100 proteins each. To increase protein identification confidence, each tandem MS spectra RAW file was searched using X! Tandem, OMSSA, and SageN SEQUEST against the IPI protein database (currently vs. 3.6 with full trypsin digestion) and the protein and peptide identification results compiled for each patient in Maspectras and Scaffold. Initial lead proteins were identified based on presence/absence or a ≥1.5 fold change (increase or decrease) in spectral counts of peptides in the SCI and non-SCI samples.

Brain Injury Protein Identification.

Using semi-quantitative spectral count fold change cut off of 1.5, proteins circulating in children with SCI are listed below in Table 1. These peptide identifications have an expectation value of $<10^{-1}$.

TABLE 1

Brain Injury Protein Biomarkers

| Accession No. | Protein Name |
|---|---|
| P07996 | Thrombospondin-1 |
| P14151 | L-selectin |
| P31949 | Protein S100-A11 |
| Q9P273 | Teneurin-3 |
| P18206 | Vinculin |
| P25815 | Protein S100-P |
| Q86WP2 | Vasculin |
| P50552 | Vasodilator-stimulated phosphoprotein |
| P80511 | Protein S100-A12 |
| P41222 | Prostaglandin-H2 D-isomerase |
| Q86V38 | Atrophin 1 |
| Q92686 | Neurogranin |
| Q15465 | Sonic hedgehog protein |
| O43426 | Synaptojanin-1 |
| P02775 | Platelet basic protein |
| Q05682 | Caldesmon |
| Q9H461 | Frizzled-8 |
| P06703 | Protein S100-A6 |
| P62158 | Calmodulin |
| P80723 | Brain acid soluble protein 1 |
| Q9NQC3 | Reticulon-4 |
| Q9Y5Y7 | Lymphatic vessel endothelial hyaluronic acid receptor 1 |
| P36955 | Pigment epithelium-derived factor |
| P06702 | Protein S100-A9 |
| Q8TBZ2 | MYCBP-associated protein |
| A6NIX2 | Wilms tumor protein 1-interacting protein |
| A0AVI2 | Fer-1-like protein 5 |
| O00151 | PDZ and LIM domain protein 1 |
| O95744 | Postmeiotic segregation increased 2-like protein 2 |
| Q68D06 | Schlafen family member 13 |
| P40121 | Macrophage-capping protein |
| Q6UXX5 | Inter-alpha-trypsin inhibitor heavy chain H5-like protein |
| P02788 | Lactotransferrin |
| Q5JNX2 | Complement component 4A (Rodgers blood group) (Uncharacterized protein ENSP00000372815) |
| Q68CR7 | Leucine-rich repeat-containing protein 66 |
| A2BHY4 | Complement component C4B (Childo blood group) |
| P17097 | Zinc finger protein 7 |
| P19652 | Alpha-1-acid glycoprotein 2 |
| Q5VT06 | Centrosome-associated protein 350 |
| Q7L211 | Abhydrolase domain-containing protein 13 |
| Q9P1Z9 | Uncharacterized protein KIAA1529 |
| P98073 | Enteropeptidase |
| Q9P242 | Uncharacterized protein KIAA1486 |
| Q7Z5P9 | Mucin-19 |

TABLE 1-continued

Brain Injury Protein Biomarkers

| Accession No. | Protein Name |
|---|---|
| A6NII9 | Putative uncharacterized protein ENSP00000351043 (Family with sequence similarity 19 (Chemokine (C-C motif)-like), member A5, isoform CRA_a) (Putative uncharacterized protein ENSP00000336812) |
| A8MSL6 | Putative uncharacterized protein APOA4 |
| Q7Z7G8 | Vacuolar protein sorting-associated protein 13B |
| P02750 | Leucine-rich alpha-2-glycoprotein |
| P10720 | Platelet factor 4 variant |
| IPI00896413.1 | INTER-ALPHA (GLOBULIN) INHIBITOR H4 ISOFORM 2 PRECURSOR. |
| P15924 | Desmoplakin |
| Q9UKV3 | Apoptotic chromatin condensation inducer in the nucleus |
| O15417 | Trinucleotide repeat-containing gene 18 protein |
| Q06830 | Peroxiredoxin-1 |
| Q14766 | Latent-transforming growth factor beta-binding protein, isoform 1L |
| Q49AS2 | ELK2, member of ETS oncogene family, pseudogene 1 |
| P55042 | GTP-binding protein RAD |
| P10599 | Thioredoxin |
| P35579 | Myosin-9 |
| Q9NVN8 | Guanine nucleotide-binding protein-like 3-like protein |
| Q03828 | Homeobox even-skipped homolog protein 2 |
| P16401 | Histone H1.5 |
| Q7Z7M0 | Multiple epidermal growth factor-like domains 8 |
| Q9NYF0 | Dapper homolog 1 |
| Q02747 | Guanylin |
| Q9HCJ5 | Zinc finger SWIM domain-containing protein 6 |
| Q8TEH0 | FLJ00227 protein |
| P60323 | Nanos homolog 3 |
| Q9P2H0 | Uncharacterized protein KIAA1377 |
| Q9Y6X6 | Myosin-XVI |
| O60299 | Uncharacterized protein KIAA0552 |
| Q8NDT4 | Zinc finger protein 663 |
| Q8NDX1 | PH and SEC7 domain-containing protein 4 |
| P02760 | Protein AMBP |
| P20851 | C4b-binding protein beta chain |
| P52209 | 6-phosphogluconate dehydrogenase, decarboxylating |
| A6NI80 | Uncharacterized protein ENSP00000305613 |
| Q96LW6 | cDNA FLJ33157 fis, clone UTERU2000393 (HCG2021706) |
| Q9NZV6 | Methionine-R-sulfoxide reductase B1 |
| P04114 | Apolipoprotein B-100 |
| Q8WY24 | SNC66 protein |
| Q5T8A7 | Protein KIAA0649 |
| Q68DS3 | Putative uncharacterized protein DKFZp686H17246 |
| P02790 | Hemopexin |
| O60907 | F-box-like/WD repeat-containing protein TBL1X |
| P02745 | Complement C1q subcomponent subunit A |
| Q96IY4 | Carboxypeptidase B2 |
| Q12947 | Forkhead box protein F2 |
| Q13505 | Metaxin-1 |
| Q71RA9 | PP7706 |
| Q99747 | Gamma-soluble NSF attachment protein |
| P35858 | Insulin-like growth factor-binding protein complex acid labile chain |
| P00736 | Complement C1r subcomponent |
| O15370 | SOX-12 protein |
| P08670 | Vimentin |
| P02746 | Complement C1q subcomponent subunit B |
| Q96CP6 | GRAM domain-containing protein 1A |
| Q92954 | Proteoglycan 4 |
| P10412 | Histone H1.4 |
| P32119 | Peroxiredoxin-2 |
| P06733 | Alpha-enolase |
| Q9UPP5 | Uncharacterized protein KIAA1107 |
| Q5T8R8 | Uncharacterized protein C9orf66 |
| Q9NY12 | H/ACA ribonucleoprotein complex subunit 1 |
| P07360 | Complement component C8 gamma chain |
| P04004 | Vitronectin |
| Q8NCM2 | Potassium voltage-gated channel subfamily H member 5 |
| A8K5V8 | cDNA FLJ30633 fis, highly similar to Homo sapiens modulator of estrogen induced transcription, transcript variant 1, mRNA |
| Q9BTL4 | Immediate early response gene 2 protein |
| Q96PD5 | N-acetylmuramoyl-L-alanine amidase |
| IPI00807369.1 | IPI00807369.1 |
| IPI00788213.2 | IPI00788213.2 |
| B4E2M5 | cDNA FLJ58975 |
| IPI00782956.2 | IPI00782956.2 |
| IPI00878453.1 | IPI00878453.1 |
| P02452 | Collagen alpha-1(I) chain |

TABLE 1-continued

Brain Injury Protein Biomarkers

| Accession No. | Protein Name |
|---|---|
| Q9BXB5 | Oxysterol-binding protein-related protein 10 |
| IPI00457142.3 | SIMILAR TO U2 SMALL NUCLEAR RNA AUXILLARY FACTOR 1 |
| O75528 | Transcriptional adapter 3-like |
| P04196 | Histidine-rich glycoprotein |
| P08123 | Collagen alpha-2(I) chain |
| IPI00867606.2 | ISOFORM 2 OF RAS-GEF DOMAIN-CONTAINING FAMILY MEMBER 1B |
| O95696 | Bromodomain-containing protein 1 |
| P49588 | Alanyl-tRNA synthetase, cytoplasmic |
| IPI00794089.1 | IPI00794089.1 |
| O75052 | Carboxyl-terminal PDZ ligand of neuronal nitric oxide synthase protein |
| P49748 | Very long-chain specific acyl-CoA dehydrogenase, mitochondrial |
| Q96JQ0 | Protocadherin-16 |
| P02654 | Apolipoprotein C-I |
| O94906 | Pre-mRNA-processing factor 6 |
| Q96M32 | Putative adenylate kinase 7 |
| P36980 | Complement factor H-related protein 2 |
| Q9H2Y7 | Zinc finger protein 106 homolog |
| Q68DL7 | Uncharacterized protein DKFZp781G0119 |
| IPI00883666.2 | IPI00883666.2 |
| Q66PJ3 | ADP-ribosylation factor-like protein 6-interacting protein 4 |
| Q9UPA5 | Protein bassoon |
| P60602 | Protein MGR2 homolog |
| Q8N2B8 | Putative uncharacterized protein FLJ33534 |
| Q96HY7 | Probable 2-oxoglutarate dehydrogenase E1 component DHKTD1, mitochondrial |
| Q96T92 | Insulinoma-associated protein 2 |
| Q9UKK3 | Poly [ADP-ribose] polymerase 4 |
| O76042 | Uncharacterized protein C3orf51 |
| P02656 | Apolipoprotein C-III |
| P02461 | Collagen alpha-1(III) chain |
| IPI00219910.2 | IPI00219910.2 |
| IPI00442185.1 | IPI00442185.1 |
| IPI00794089.1 | IPI00794089.1 |
| IPI00847731.1 | IPI00847731.1 |

Example 2: Discovery of Circulation Biomarkers of Subclinical Brain Injury (SCI) in Children with Sickle Cell Disease (SCD)

Children with SCD and SCI have significant learning defects and are at increased risk for stroke. Early detection of SCI would allow institution of therapies to prevent further brain injury and neurocognitive defects, including loss of I.Q. By definition, SCI patients have MRI and pathologic evidence of brain injury consistent with microinfarction. Therefore, it is likely that unique circulating biomarkers exist to identify patients with SCI as has been shown in non-SCD patients with overt stroke. The present goal of is to use non-biased proteomic techniques to explore clinically paired groups of SCI and non-SCI patient plasma samples to identify lead proteins for validation as circulating biomarkers of SCI.

Study Population.

The study population comprised male and female children 6-12 years old with SCD participating in the SIT Trial (24 institutions) having an adjudicated MRI with (SCI group) or without (non-SCI group) evidence of SCI. As part of the SIT Trial, in addition to an MRI and neurologic exam, patients have CBC, Hb/Hct, hemoglobin electrophoresis and other clinical studies determined. At entry into the trial, citrated plasma is prepared, frozen and stored in the Biologic Repository at Johns Hopkins at −70° C. The initial discovery cohort for this Example, as described in Table 2, includes 50 patients with SCI and 50 patients without SCI, all with an Hb<8.1 g/dL, as this has been shown to be an independent risk factor for SCI.

Depletion of Abundant Proteins.

To identify proteins with altered plasma expression in children with SCI, 250 μL aliquots of individual plasma samples from SCI and non-SCI children were affinity depleted using a new generation of the previously available LC10 polyclonal antibody affinity column (IgY high capacity LC10 column, Beckman-Coulter). This new generation column doubles the amount of plasma that can be depleted (from 125 to 250 μl), thereby increasing downstream sensitivity. This new column is coupled to the ProteomeLab PPS Proteome Partitioning System (Beckman-Coulter) for flow through and bound protein collection. For each 250 μl of plasma depleted, 7 ml of flow through protein is collected. In total, 750 μl of plasma from each patient was depleted, providing >1 mg (as 21 ml of pooled column flow through) of depleted proteins for downstream RP-HPLC fractionation. Using a 4 ml loop, five separate runs of 4 ml each of the flow-through proteins (collected from depletion of 750 μl of plasma) was fractionated by RP-HPLC (ProteomeLab PPS Proteome Partitioning System) coupled to a $C_{18}$ non-porous column, using a linear acetonitrile gradient, with 60 fractions collected over 30 minutes. The RP-HPLC fractions for each of the five RP-HPLC runs are collected in the same plate to increase the protein concentration of each fraction. Although repeat RP-HPLC fractionation to process the large depleted protein volume (21 ml) is cumbersome, it is superior to the alternative, size exclusion centrifugation. Size exclusion centrifugation results in unacceptable protein loss from (a) non-specific binding of protein to the centrifugation column; and (b) inherent loss of proteins <10 kDa (which includes vasoactive peptides such as angiotensin II, bradykinin and endothelin, which may be quite important in the pathology of SCI). Protein loss of this magnitude is unacceptable for discovery based approaches as described in this Example. In contrast, repeat RP-HPLC fractionation is extremely reproducible.

To determine which peaks of the RP-HPLC chromatogram would be processed for MS, overlay software (32-Karat software, Beckman-Coulter) and newer algorithms (developed in cooperation with Ludesi, Inc.) were used. Both of these tools are particularly useful in later analysis of the discovery cohort. Based on the analysis of 4 SCI and 4 non-SCIRP-HPLC chromatograms, 32 (of 60 total) fractions vary enough between SCI and non-SCI patients for subsequent analysis. See FIG. 1.

Identification and Quantification of Small and Low Abundant Plasma Proteins in SCI.

To identify the proteins contained in the RP HPLC fractions described above, LC/MS/MS (LTQ Orbitrap) analysis of each RP HPLC fraction was used to develop a non-SCI/SCI plasma protein database. Briefly, the pooled RP HPLC fractions from a single patient were completely dried using a SpeedVac, resuspended in neutralization buffer and trypsin digested overnight. After trypsin digestion, the RP HPLC fractions were analyzed by LC/MS/MS (Thermo LTQ-Orbitrap). Each RP HPLC fraction contains 50-100 proteins. A database of protein (in Maspectras) was developed and mined for differential protein expression between the two groups and annotated into functional and cell-type specific proteins for subsequent study. Once specific RP-HPLC fractions from ASCI and non-SCI patients were identified to contain potential candidate proteins of interest, proteins in these fractions were quantified using the mass spectroscopy technique, multiple reaction monitoring (MRM). Briefly, after trypsin, samples were submitted for LC/MS/MS identification and quantification using peptide signatures for biomarkers proteins. The Web-based Maspectras database was used to store raw, processed and final proteomic data for analysis and protein profiling.

Brain Injury Protein Identification.

Using the NCBI's list of brain-specific proteins based on EST tags in Unigene (NCBI), 104 brain proteins circulating in children with SCI were identified. See Table 2. These peptide identifications have an expectation value of <0.9.

TABLE 2

Brain Injury Protein Biomarkers

| Gene Name | Protein Full Name |
| --- | --- |
| 5HT1A | 5-hydroxytryptamine receptor 1A |
| ACCN4 | Isoform 1 of Amiloride-sensitive cation channel 4 |
| AIFM3 | Isoform 1 of Apoptosis-inducing factor 3 |
| ANO3 | Anoctamin-3 |
| ATP1A3 | Sodium/potassium-transporting ATPase subunit alpha-3 |
| B3KXG7 | cDNA FU45381 fis, clone BRHIP3021019, highly similar to Homo sapiens protein tyrosine phosphatase, non-re< |
| BAI3 | Brain-specific angiogenesis inhibitor 3 |
| BAIAP3 | Isoform 1 of BAII-associated protein 3 |
| BCAN | Isoform 1 of Brevican core protein |
| CAMK1G | Isoform 1 of Calcium/calmodulin-dependent protein kinase type 1G |
| CAMKV | CaM kinase-like vesicle-associated protein |
| CDH20 | Cadherin-20 |
| CHD5 | Chromodomain-helicase-DNA-binding protein 5 |
| CHIN | N-chimaerin |
| CLDND1 | Isoform 1 of Claudin domain-containing protein 1 |
| CNDP1 | Beta-Ala-His dipeptidase |
| COKA1 | Collagen alpha-1(XX) chain |
| CTNND2 | Isoform 1 of Catenin delta-2 |
| DNAJC18 | DnaJ homolog subfamily C member 18 |
| DNM3 | Isoform 1 of Dynamin-3 |
| D0CK3 | Dedicator of cytokinesis protein 3 |
| DYNC1I1 | Isoform 1 of Cytoplasmic dynein 1 intermediate chain 1 |
| ERMN | Ermin |
| ETBR2 | Endothelin B receptor-like protein 2 |
| FAM171A1 | Protein FAM171A1 |
| FAM5B | Isoform 1 of Protein FAM5B |
| FAM5C | Protein FAM5C |
| FGF1 | Isoform 1 of Heparin-binding growth factor 1 |
| FU45872 | cDNA FU45872 fis, clone OCBBF3005843 |
| FSTL5 | Follistatin-related protein 5 |
| GABBR1 | Isoform 1A of Gamma-aminobutyric acid type B receptor subunit 1 |
| GABRA4 | Gamma-aminobutyric acid receptor subunit alpha-4 |
| GBRA6 | Gamma-aminobutyric acid receptor subunit alpha-6 |
| GFAP | Isoform 1 of Glial fibrillary acidic protein |
| GNAO | Guanine nucleotide-binding protein G(o) subunit alpha |
| GPR37 | Probable G-protein coupled receptor 37 |
| GPRASP2 | G-protein coupled receptor-associated sorting protein 2 |
| GRIN2B | Glutamate [NMDA] receptor subunit epsilon-2 |
| GRM2 | Metabotropic glutamate receptor 2 |
| GRM3 | Metabotropic glutamate receptor 3 |
| GUCY1B3 | Isoform HSGC-1 of Guanylate cyclase soluble subunit beta-1 |
| HEPACAM | Isoform 1 of Hepatocyte cell adhesion molecule |
| KBTBD11 | Kelch repeat and BTB domain-containing protein 11 |
| KCNA1 | Potassium voltage-gated channel subfamily A member 1 |
| KCNS1 | Potassium voltage-gated channel subfamily S member 1 |
| KCNV1 | Potassium voltage-gated channel subfamily V member 1 |
| KIF19 | Isoform 1 of Kinesin-like protein KIF19 |

TABLE 2-continued

Brain Injury Protein Biomarkers

| Gene Name | Protein Full Name |
|---|---|
| KIF5A | Kinesin heavy chain isoform 5A |
| KIF5C | Isoform 1 of Kinesin heavy chain isoform 5C |
| KLH32 | Kelch-like protein 32 |
| KLHL1 | Kelch-like protein 1 |
| LGI1 | Isoform 1 of Leucine-rich glioma-inactivated protein 1 |
| LRFN2 | Leucine-rich repeat and fibronectin type-III domain-containing protein 2 |
| MAGE2 | Melanoma-associated antigen E2 |
| MAP2 | Isoform 1 of Microtubule-associated protein 2 |
| MAP7D2 | Isoform 1 of MAP7 domain-containing protein 2 |
| MLC1 | Membrane protein MLC1 |
| MOG | Myelin oligodendrocyte glycoprotein, isoform CRA_d |
| NAP1L3 | Nucleosome assembly protein 1-like 3 |
| NCAM1 | Isoform 1 of Neural cell adhesion molecule 1 |
| NDF2 | Neurogenic differentiation factor 2 |
| NEUG | Neurogranin |
| NMDE2 | Glutamate [NMDA] receptor subunit epsilon-2 |
| NRG3 | Isoform 1 of Pro-neuregulin-3, membrane-bound isoform |
| NRG3 | Pro-neuregulin-3, membrane-bound isoform |
| NRGN | Neurogranin |
| OMGP | Oligodendrocyte-myelin glycoprotein |
| PAQR6 | Progestin and adipoQ receptor family member 6 |
| PAX7 | Isoform Long of Paired box protein Pax-7 |
| PCDHA9 | Isoform 1 of Protocadherin alpha-9 |
| PCDHB10 | Protocadherin beta-10 |
| PDE1B | Calcium/calmodulin-dependent 3',5'-cyclic nucleotide phosphodiesterase IB |
| PHYHIP | Phytanoyl-CoA hydroxylase-interacting protein |
| PLXNA4 | Isoform 1 of Plexin-A4 |
| PNMA3 | Isoform 1 of Paraneoplastic antigen Ma3 |
| PRMT8 | Protein arginine N-methyltransferase 8 |
| PTN5 | Tyrosine-protein phosphatase non-receptor type 5 |
| PTPRN | Receptor-type tyrosine-protein phosphatase-like N |
| Q59GK5 | Glutamate receptor, metabotropic 4 variant |
| Q75MI7 | Putative uncharacterized protein DPP6 |
| RFPL1 | Ret finger protein-like 1 |
| RIMS1 | Isoform 1 of Regulating synaptic membrane exocytosis protein 1 |
| RP3A | Rabphilin-3A |
| RTN3 | Isoform 1 of Reticulon-3 |
| S39AC | Zinc transporter ZIP12 |
| SC6A7 | Sodium-dependent proline transporter |
| SCN8A | Isoform 1 of Sodium channel protein type 8 subunit alpha |
| SCN8A | Sodium channel protein type 8 subunit alpha |
| SERPINI1 | Neuroserpin |
| SH3GL2 | Endophilin-A1 |
| SLC1A2 | Excitatory amino acid transporter 2 |
| SLC32A1 | Vesicular inhibitory amino acid transporter |
| SLCO1A2 | Isoform OATP1a of Solute carrier organic anion transporter family member 1A2 |
| SLIK3 | SLIT and NTRK-like protein 3 |
| SNAP91 | Isoform 1 of Clathrin coat assembly protein AP180 |
| SNX32 | Sorting nexin-32 |
| STXBP1 | Isoform 1 of Syntaxin-binding protein 1 |
| SV2B | Synaptic vesicle glycoprotein 2B |
| TNR | Isoform 1 of Tenascin-R |
| VA0E2 | V-type proton ATPase subunit e 2 |
| WASF1 | Wiskott-Aldrich syndrome protein family member 1 |
| WFIKKN2 | WAP, kazal, immunoglobulin, kunitz and NTR domain-containing protein 2 |
| WNT16 | Isoform Wnt-16b of Protein Wnt-16 |
| WSCD2 | Isoform 1 of WSC domain-containing protein 2 |

Example 3: Biomarker Panel for Diagnosis of Subclinical Brain Injury

Further analysis of the data described herein, as well as data from a cohort of adults having heart surgery, resulted in the following panel of biomarkers that can be used individually, or in combination to diagnose/assess subclinical brain injury.

TABLE 3

Biomarker Panel for Subclinical Brain Injury

| Protein Symbol | Protein Name |
| --- | --- |
| ASTN1 | Astrotactin1 |
| BAI3 | Brain angiogenesis inhibitor 3 |
| CNDP1 | Carnosine dipeptidase 1 |
| ERMIN | ERMIN |
| GFAP | Glial fibrillary acidic protein |
| GRM3 | Glutamate receptor, metabotropic 3 |
| KLH32 | Kelch-like protein 32 |
| MAGE2 | Melanoma antigen family E, 2 |
| NRG3 | Neuregulin 3 |
| NRGN | Neurogranin |
| OMG | Oligodendrocyte myelin glycoprotein |
| SLC39A12 | Solute carrier family 39 (zinc transporter), member 12 |
| RTN | Reticulon 1 |
| MT3 | Metallothionein 3 |

Example 4: Proteomic Identification of Glial Fibrillary Acidic Protein as a Plasma Biomarker of Brain Injury in Children with Sickle Cell Disease Sickle cell disease (SCD) is a chronic hemolytic anemia that is characterized by injury to multiple organs. Stroke is the most prominent injury that can occur to the brain in SCD. Stroke risk has been reduced significantly in children by identifying those patients with elevated transcranial Doppler velocities and implementing chronic red cell transfusion. Adams et al., 339 N. ENG. J. MED. 5-11 (1998). It is currently under study whether risk for brain injury, as ascertained by presence of silent cerebral infarct (SCI) on MRI, can be mitigated by chronic red blood cell transfusion. King et al., 50 PEDIATR. BLOOD CANCER 599-602 (2008). Clearly, biomarkers of stroke risk have transformed care in sickle cell disease.

In children, SCI is an independent risk factor for lower IQ, poorer school performance, and overt stroke. Miller et al., 139 J. PEDIATR. 385-90 (2001); and Bernaudin et al., 15 J. CHILD NERUOL. 333-43 (2000). MRI is the only method to identify those patients with SCI. MRI is not an ideal technique to track disease risk because it is expensive, it has limitations on how frequently it can be used, and for some pediatric patients it requires anesthesia, which carries increased risk in SCD, including death. See Vicinsky et al., 333 N. ENGL. J. MED. 206-13 (1995). A blood biomarker of SCI would fill a clinical void because blood is easy to obtain and measure, a biomarker may determine risk of or progression of neurologic injury to overt stroke, and a biomarker could benchmark current and new therapies for SCI.

In adults with overt stroke, plasma levels of neuronal and glial proteins are thought to reflect continuous cellular leak from areas of infarction. Biomarkers in this group can be very specific for brain injury. This approach of using brain specific proteins has been taken by investigators to identify biomarkers of overt stroke in adults, with several candidate proteins identified for study. See Allard et al., 51 CLIN. CHEM. 2043-51 (2005); Allard et al., 4 PROTEOMICS 2242-51 (2004) However, the identification of SCI from brain-specific proteins leaked into the plasma of SCD patients has not been described.

Using a non-biased proteomics approach, glial fibrillary acidic protein (GFAP) was identified in the plasma of SCD patients with SCI who were screened by MRI and proteomic analysis. GFAP is a highly brain-specific intermediate filament protein that is a known biomarker of acute stroke and head trauma in adults. Vos et al., 62 NEUROLOGY 1303-10 (2004); Herrmann et al., 31 STROKE 2670-77 (2000); and Lewis et al., 81 PROC. NATL. ACAD. SCI. U.S.A. 2743-46 (1984). It has been shown to correlate with prognosis and lesion density in these conditions. Nylen et al., 240 J. NEUROL. SCI. 85-91 (2006); Wunderlich et al., 13 EUR. J. NEUROL. 1118-23 (2006). Given the identification of GFAP in the proteomics screen and the available literature describing it, it is therefore hypothesized that GFAP concentrations could serve as a biomarker of brain injury in sickle cell disease.

Methods

Patients.

A cross-sectional sample of children 5-14 years old with sickle cell disease (HbSS and HbSβ$^0$) who were screened for the Silent Infarct Transfusion Trial (SIT Trial, ClinicalTrials.gov NCT00072761) were studied (n=259). The SIT Trial is a multi-center, randomized, controlled trial of a three year-transfusion program in children with sickle cell disease and SCI. The primary endpoint includes the occurrence of overt stroke or new or progressive SCI. All patients signed informed consent. SCI is defined by a normal neurologic exam and MRI signal abnormality visible on two views on T2 weighted images. The signal abnormality must measure at least 3 mm in one dimension. SCI status is adjudicated by a panel of neuroradiologists and neurologists. See Vendt et al., 22(3) J. DIGIT. IMAGING 326-43 (2009). Positive and negative control patients were selected from Johns Hopkins Hospital clinics and inpatient units. Positive control plasma samples were obtained from hospitalized children and adults admitted for overt stroke or brain surgery. Negative controls were selected from children 5-16 years old from the Harriet Lane Pediatrics Clinic at Johns Hopkins Hospital. Clinic notes were reviewed to exclude patients with any acute illness, neurologic disorder, or chronic illness other than asthma, obesity, and behavior/mood disorders. De-identified blood samples and clinical data on these controls were obtained through an IRB approved study.

Plasma Preparation and Mass Spectroscopic Analysis.

Blood was collected into ACD or EDTA tubes and spun at 1500 g for 8 minutes per the SIT Trial protocol and stored at −70° C. in the Biologic Repository for the SIT Trial at Johns Hopkins University until analysis. Five hundred microliters of plasma was depleted of 12 abundant plasma proteins using an LC10 IgY column (Beckman Coulter, Fullerton, Calif.) on a ProteomeLab Protein Partitioning System (PPS, Beckman). IgY column flow through was separated into 39 fractions by reverse phase HPLC over a C18 column (Jupiter, Phenomenex) using a continuous acetonitrile gradient (PPS, Beckman). Fractions were dried (SpeedVac, Thermo Scientific, Waltham, Mass.) and trypsin digested (Promega, Madison, Wis.) at 37° C. overnight. Spectra on each sample were obtained by LC/MS/MS (LTQ-Orbitrap, Thermo Scientific). Spectra were searched for protein identifications using SEQUEST (Sorcerer, SageN, Pennington, N.J.) and a human IPI database version 3.4. Post search analysis was performed using Protein Center with a confidence level of <0.9 as a protein identification cut off.

GFAP Measurements.

GFAP was measured in undiluted duplicate plasma samples using an electrochemiluminescent sandwich immunoassay (MesoScale Discovery, Gaithersburg, Md.). The monoclonal anti-GFAP blend SMI-26 (Covance, Princeton, N.J.) at 100 ng in 30 μL PBS per well was incubated overnight in standard bind MSD plates for capture. Polyclonal anti-GFAP (Dako, Carpinteria, Calif.) that was directly conjugated with Sulfo-Tag (MesoScale Discovery) was used for detection at 1 μg/ml in PBS. Standard curves were made with 4-fold dilutions of purified GFAP (Calbiochem, La Jolla, Calif.) in 1% bovine serum albumin (SeraCare Life Sciences, Milford, Mass.). To minimize analytical variability, control and sickle cell patient samples were assayed on the same plate whenever possible. Assays were analyzed on a Sector Imager 2400 (MesoScale Discovery) according to the manufacturer's protocol.

Statistics.

Student's t test was used to compare GFAP concentrations between groups. Natural log-transformed values of GFAP approximated a normal distribution and were used for parametric analyses. Tests of proportion were performed using Fisher's exact test. Analysis was conducted using Stata v10.1 (Stata Corporation, College Station, Tex.)

Results

Mass Spec Identification of GFAP in Plasma.

Figure 2:
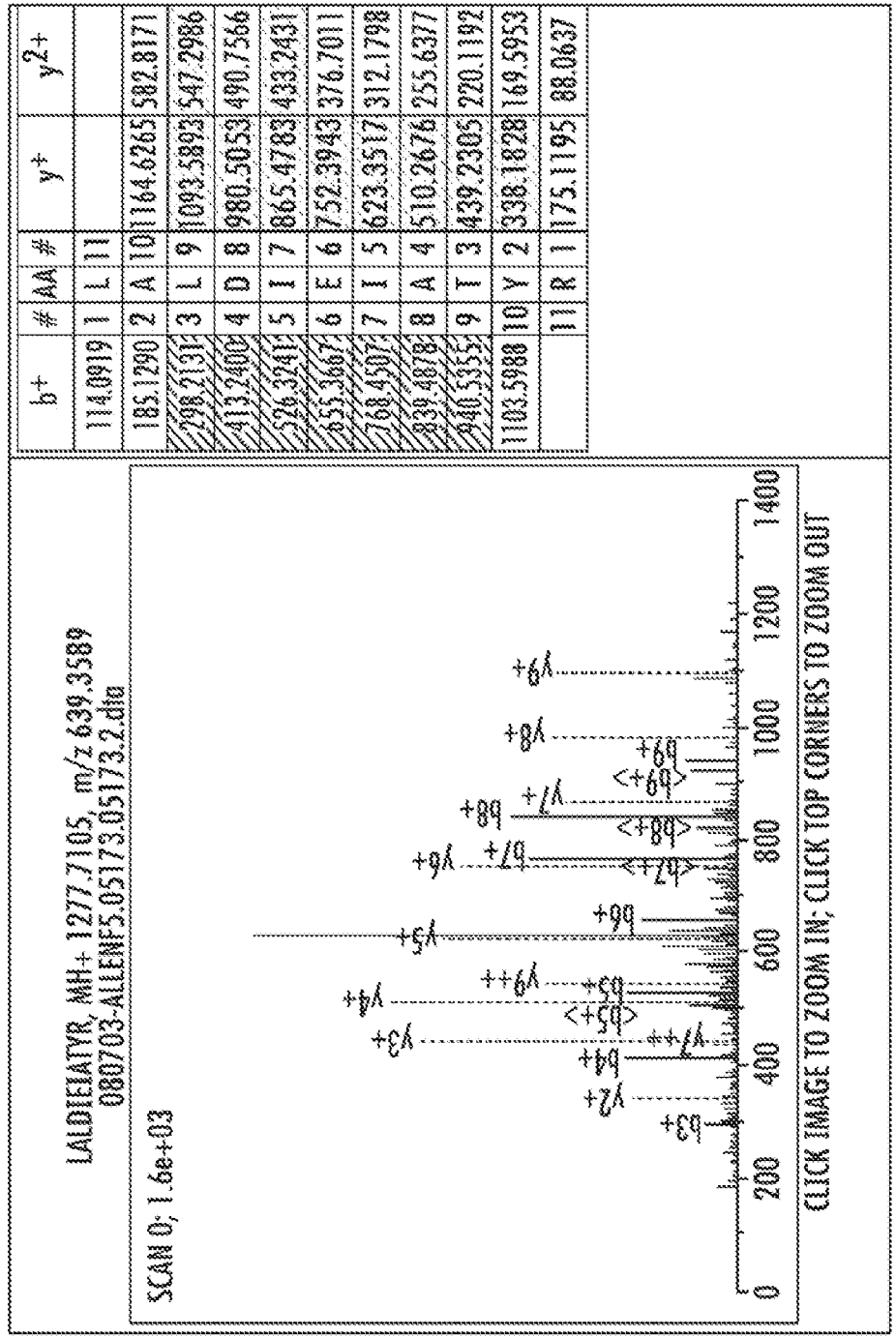
FIG. 2 shows the spectra ion table for GFAP peptide. The pepP probability was 0.7598 and the XCORR 4.016. This peptide was found in 4 of 6 SCI patients.

A GFAP peptide was identified by SEQUEST searches in 4 of 6 plasma samples from SIT Trial subjects with SCI. See FIG. 2.

Performance and Validation of GFAP Electrochemiluminescent Immunoassay.

The GFAP assay was developed using the antibody reagents described by Petzold and adapted to the MSD platform. See Petzold et al., 287 J. IMMNOL. METHODS 169-77 (2004). Validation of this method was performed. After experiments to determine the optimal antibody concentrations, plate type, and blocking material, the final assay as used for all the GFAP values reported herein had a lower limit of detection of 0.011 ng/ml as defined by 2 SD above the background of blank wells (n=19 experiments). The signal to noise ratio was 1.17 at 0.01 ng/ml (n=19 experiments). The lower limit of quantitation, defined as the lowest dilution with a calculated concentration+/−20% of a known concentration, was 0.026 ng/ml (n=3 experiments). Interassay precision was 2.4% at 10 ng/ml and 3.4% at 0.156 ng/ml (n=21 experiments). Plasma spiked with GFAP shows 49.8%+/−22.9% recovery at 10 ng/ml, when compared to a standard curve generated in BSA. Whether GFAP was stable in plasma at room temperature was determined for at least 48 hours to confirm that assay values were not an artifact of in vitro proteolysis. Serial measurements from the same aliquot at t=0, 6, 24, and 48 hours show a CV of 2.5% at 2 ng/ml and 12.1% at 0.2 ng/ml demonstrating the stability of GFAP in plasma.

Plasma GFAP in Sickle Cell Disease and Controls.

Figure 3:
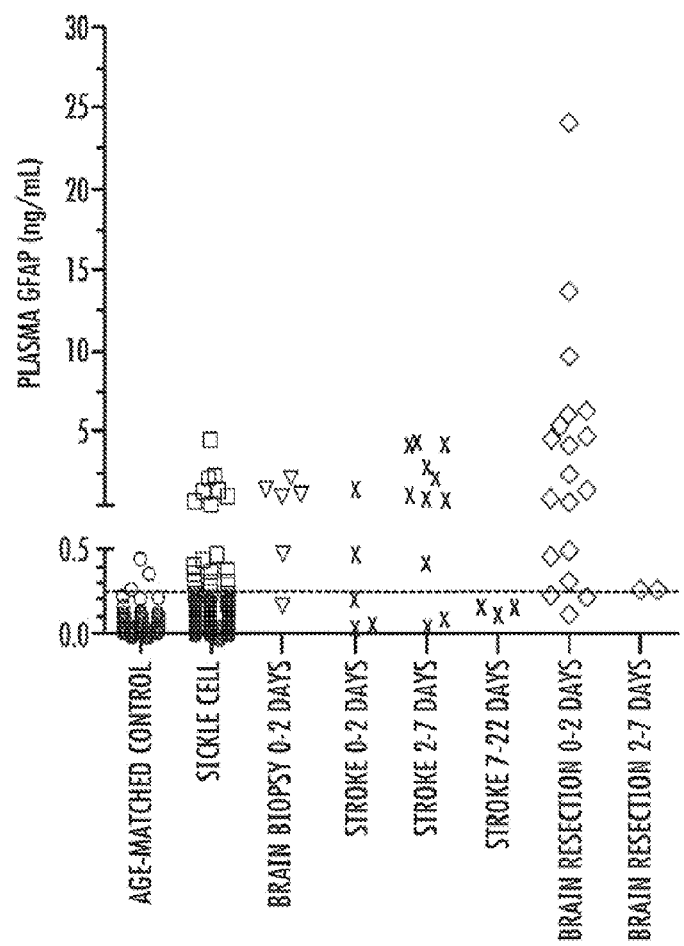
FIG. 3 displays Plasma GFAP concentrations in steady-state sickle cell disease (n=259, HbSS and HbSβ⁰, 5-14 years old), healthy children (n=47), and non-sickle cell in patients who had acute stroke (20 samples from 12 patients), brain biopsy (6 samples from 3 patients), or partial brain resection (22 samples from 13 patients). The dashed line marks the 95$^{th}$ percentile value among 47 healthy controls age-matched to the SITT cohort.

To validate that the GFAP assay detected elevated plasma GFAP in the context of brain injury, a positive control population composed of plasma samples from children and adults 0-5 days after acute stroke, brain biopsy, or partial brain resection patients was assayed. FIG. 3 shows GFAP levels for stroke (median 0.446 ng/ml, range 0.029-4.29 ng/ml), brain biopsy (median 0.96 ng/ml, range 0.162-1.93 ng/ml), and brain resection (median 1.29 ng/ml, range 0.122-24.1 ng/ml). As the plasma concentration of GFAP in children is unknown, the normal range was established using age-matched controls (5-16 years) from a general pediatric outpatient clinic. Healthy control subjects had blood drawn for screening purposes and were free of acute illness. Of the healthy controls, 46/47 were of African descent. The $95^{th}$ percentile for GFAP in normal age matched controls was 0.244 ng/ml. Among positive controls, 74% had GFAP concentrations higher than the $95^{th}$ percentile of normal controls (p<0.0001).

Comparing the population of SITT participants to healthy controls shows that the two groups have comparable mean concentrations of plasma GFAP (p=0.12). The median GFAP among SITT participants is 0.065 ng/ml ($10^{th}$ percentile 0.026, $90^{th}$ percentile 0.225), and among healthy controls the median is 0.055 ng/ml ($10^{th}$ percentile 0.025, $90^{th}$ percentile 0.207); however, several sickle cell subjects have plasma GFAP concentrations much higher than the highest age-matched control value. Using the $95^{th}$ percentile cutoff of age-matched, healthy controls, 8.9% of the SITT screening samples were elevated (p=0.29). Ten of the SITT screening samples (3.9%) had GFAP levels above the highest healthy, age-matched control level of 0.44 ng/ml (median GFAP of elevated SITT subjects: 1.3 ng/ml, range 0.47-4.41 ng/ml) that was comparable to the positive control groups with overt brain injury (brain biopsy, resection or stroke).

Plasma GFAP and SCI.

Figure 4:
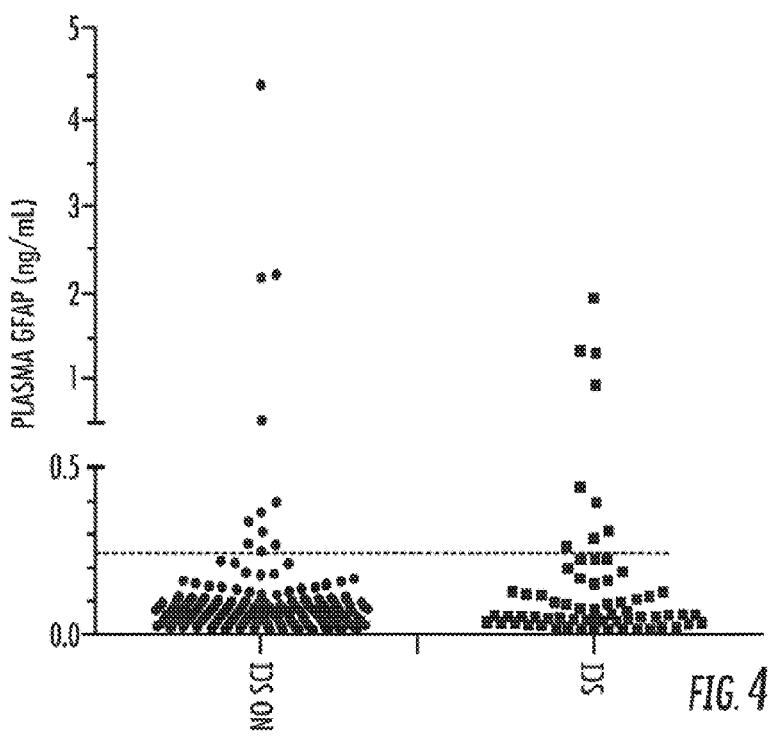
FIG. 4 displays plasma concentrations of GFAP in steady-state sickle cell disease, according to SCI status (n=66 SCI positive, n=145 SCI negative). The dashed line marks the 95th percentile value among 47 healthy, age-matched controls.

Several studies have evaluated GFAP as a marker of acute brain injury. SCI and stroke are CNS events that are well documented to occur in sickle cell disease. As shown in FIG. 4, children in both the SCI and non-SCI groups had elevated GFAP concentrations. There was no statistical difference in GFAP concentrations between SCI positive and SCI negative patients (p=0.69). The proportion of SCI patients with elevated GFAP above the $95^{th}$ percentile for age-matched, healthy controls was higher than the proportion of non-SCI patients with GFAP, but this difference is not statistically significant (13.4% vs. 7.6%, p=0.14).

Plasma GFAP in Acute Stroke in SCD.

Figure 5:
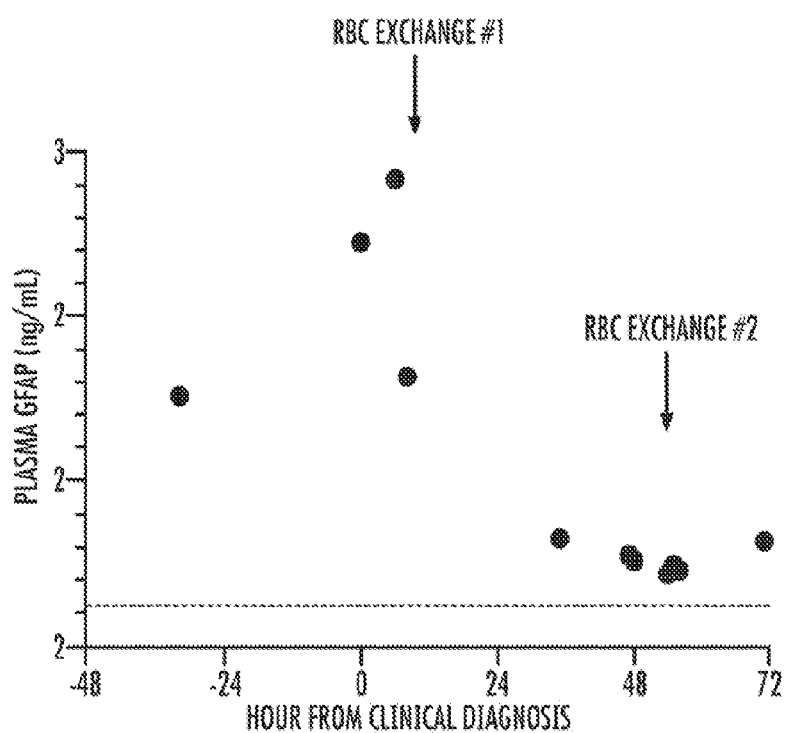
FIG. 5 shows serial plasma GFAP levels in an 11 year-old patient with HbSS and acute stroke. A red cell exchange transfusion was performed 5 hours after clinical diagnosis, and again 47 hours later for new neurologic deficits. The patient's plasma GFAP remained elevated at 0.50 ng/ml 11 days after diagnosis and returned to a normal value of 0.074 ng/ml 26 days later, immediately prior to the first scheduled red cell transfusion. The dashed line marks the 95$^{th}$ percentile value among 47 healthy, age-matched controls.
Figure 6:
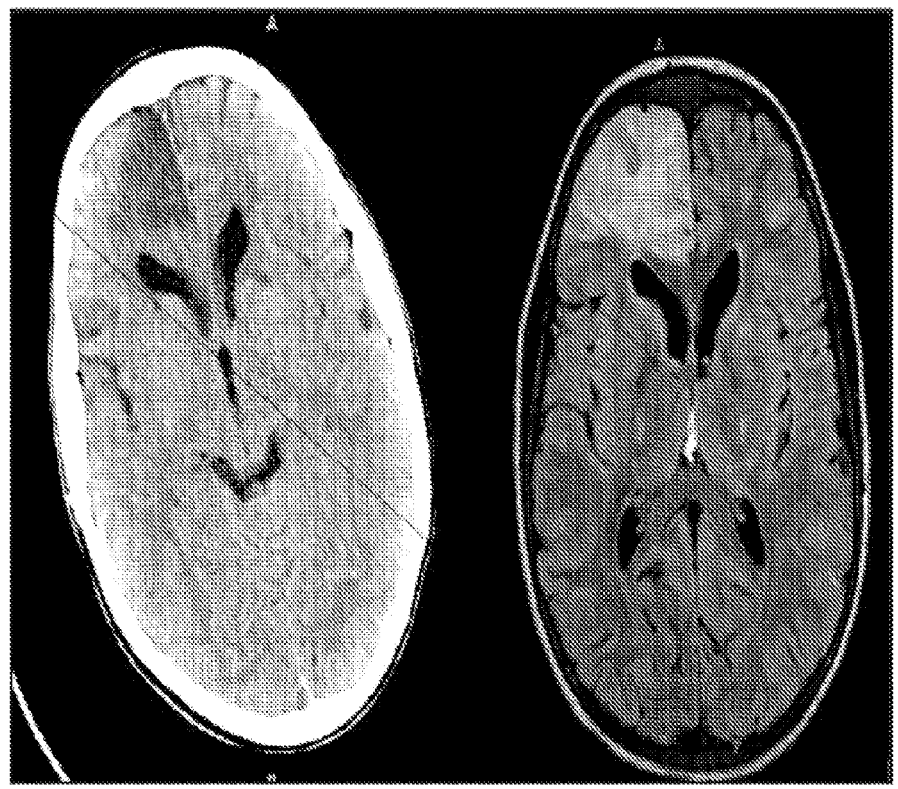
FIG. 6 displays neuroimaging of acute stroke in an HbSS patient who had plasma GFAP followed serially. Left: Non-contrast head CT immediately after clinical diagnosis of stroke showing a wedge of hypoattenuation in the right frontal lobe. Right: FLAIR MRI image 29 hours after diagnosis of stroke showing evolving right anterior cerebral artery infarct.

Although the SITT plasma samples are a unique and valuable resource, for validation purposes they pose a particular problem, in that there is no predictable temporal relationship between the plasma sample at entry into the study and development the SCI brain lesion. To further validate GFAP in the childhood SCD population as a marker of subclinical and overt stroke, FIG. 5 shows serial plasma GFAP concentrations from an 11 year-old homozygous sickle cell patient (not a SITT participant) who had an acute stroke during a febrile illness that was clinically suspicious for meningitis. CSF examination was negative for infection and hemorrhage (6 WBC/μL, 2 RBC/μL). The initial GFAP concentration (1.5 ng/ml, 6 times higher than the $95^{th}$ percentile for normal children) was measured in plasma obtained 32 hours prior to the clinical diagnosis of stroke. The GFAP level in the CSF 25 hours after the clinical diagnosis of stroke was 44.6 ng/ml. For reference, a study of GFAP in the CSF of pediatric all patients <17 years old showed CSF GFAP levels to be 0.1-0.5 ng/ml in the absence of acute injury. Osterlundh et al., 50 PEDIATR. BLOOD CANCER 793-98 (2008). MRI performed 29 hours after the clinical diagnosis of stroke showed right anterior cerebral artery infarct. See FIG. 6. This patient also demonstrates that GFAP is likely to be a marker of only acute brain injury, as GFAP levels continued to decrease after red blood cell exchange. One week after the stroke, the patient's sister, an 8 year old also with homozygous sickle cell disease, also developed a febrile illness, during which her plasma GFAP concentration was 0.088 ng/ml.

Plasma GFAP in Other Sickle Cell Morbidities.

To further explore the specificity of GFAP for brain injury in sickle cell disease, 17 in patients with HbSS had serial plasma samples (n=40) tested for GFAP. Reasons for admission were acute chest syndrome, pain crisis, influenza, fever, aplastic crisis (parvovirus B19 PCR confirmed), and priapism. GFAP was not found to be routinely elevated in sick children with SCD, with concentrations in the normal range for 39/40 samples (range 0.01-0.24 ng/ml). The highest value (0.44 ng/ml) was observed in a 4 year-old patient admitted for fever. This value is above the $95^{th}$ percentile of the normal range, but equivalent to the highest normal control value.

Discussion

Using an unbiased screen of the plasma proteome in sickle cell disease, GFAP, a known marker of brain injury, was identified. The discovery of a highly brain specific protein from the plasma in sickle cell patients validates the experimental approach to biomarker discovery used in the present example.

The present example demonstrates that GFAP is a biomarker of cerebral infarct in sickle cell disease, although not a precise biomarker of SCI, as diagnosed by MRI in a cross sectional study of SIT Trial participants, where the timing of SCI is not known. In a cross-sectional population of children 5-14 years old with steady-state sickle cell disease, 3.9% had extreme elevations of GFAP without apparent neurologic injury. It is hypothesized that these children with markedly elevated GFAP levels have subclinical brain injury. By history and neurologic exam, there were no apparent deficits.

SCI is a morbidity defined by either MRI or autopsy. Moser et al., 17 AM. J. NEURORADIOL. 965-72 (1996); and Rothman et al., 20 ANN. NEUROL. 684-90 (1986). SCI in sickle cell disease has been associated with poorer neurocognitive performance than sickle cell disease patients without SCI, but many children with sickle cell disease have poor neurocognitive function, despite normal brain MRIs. Schatz et al., 56 NEUROLOGY 1109-11 (2001); and Armstrong et al., 97 PEDIATRICS 864-70 (1996). Detection of brain injury by plasma levels of proteins highly specific for brain may be a more sensitive means for detecting injury.

SCI is an episodic event resulting from either acute or chronic vascular insult. Plasma GFAP is not elevated in most patients with SCI, and when GFAP is elevated, it is evenly distributed between SCI positive and negative patients. Using cross sectional data, linking an episodic event to a transiently elevated plasma biomarker would be a chance event; therefore, the present inventors conclude that, if GFAP is elevated in the setting of SCI, it is a transient elevation. The sickle cell patient with stroke described herein had an elevated plasma GFAP level for at least 13 days, and perhaps the elevation is shorter in SCI. Other candidate biomarkers may reflect chronic brain and vascular injury that predisposes those with sickle cell disease to SCI and overt stroke.

The pre-diagnosis elevation of plasma GFAP in the HbSS patient before diagnosis of overt stroke raises the possibility that GFAP could be used as screening test in ill patients with sickle cell disease. The cerebral infarct was at least a day old at diagnosis, because it could be visualized on non-contrast head CT. Awareness that this child had such a high GFAP level on admission to the hospital might have triggered more rapid evaluation and treatment for evolving brain injury. As plasma GFAP was not elevated in 17 other sickle cell patients admitted for non-neurologic acute problems, a prospective study of the utility of plasma GFAP to aid in the early diagnosis of stroke seems feasible, much as phospholipase A2 is being studied as a predictor of acute chest syndrome. Styles et al., 136 BR. J. HAEMATOL. 343-44 (2007). Approximately 19% of strokes in pediatric sickle cell patients are associated with antecedent medical events (Scothorn et al., 140 J. PEDIATR. 348-54 (2002)), and screening on a selected inpatient population may be useful for earlier intervention of evolving stroke.

Plasma is a unique source for biomarker discovery. Advantages are that it contains large quantities of protein, is widely available for study, and it may contain combinations of organ-specific sub-proteomes, with plasma analysis providing information about the state of these tissues. A major challenge to plasma biomarker study in plasma is the high concentration of several proteins that obscure discovery of less abundant candidate proteins. Plasma depletion of abundant proteins has enabled the discovery candidate proteins present in concentrations less than 1 ng/ml.

A challenge particular to pediatric proteomic research is the lack of an age-specific reference database. One of the initiatives of the Human Proteome Organisation (HUPO) is the Human Plasma Proteome Project (http://www.hupo.org/research/hppp/). The reference list of 9,504 proteins identified by at least one peptide is the benchmark for all plasma biomarker discovery. However, the application of these data to children is unclear. In the present example, a repository of age-matched controls was assembled for validation. A future goal is to identify the plasma proteomes of age-matched controls to aid in biomarker discovery for this and all other pediatric proteomic research.

In summary, the results of this study validate the non-biased strategy for identifying potential biomarkers of brain injury in patients with sickle cell disease by identifying GFAP, a known marker of CNS injury in other populations. The identification of GFAP in the plasma of a significant proportion of patients with sickle cell disease with no overt evidence of clinical problems, while not explained by the present study, raises interesting questions about the nature of brain injury in these individuals with SCD. Further proteomic studies of brain-specific proteins in SCD promise to be of great interest to our understanding, detection and treatment of CNS injury in SCD.

Example 5: Plasma Glial Fibrillary Acidic Protein as a Marker of Brain Injury and Predictor of Neurologic Outcomes after Extracorporeal Membrane Oxygenation The present example was conducted to determine whether plasma GFAP levels are associated with acute neurologic injury in children undergoing ECMO. This was a prospective observational cohort study of children who underwent ECMO in the Johns Hopkins 26-bed PICU from April 2008 to August 2009. All children age 1 day to <18 years who required ECMO for any indication and who received a continuous unfractionated heparin infusion during the ECMO course were eligible for this study. Twenty two patients were enrolled for GFAP analysis. The median age was 10 days (range 1 day-16 years), 12 (54.5%) patients were males and 12 (54.5%) were African-American. The main illness category was medical non-cardiac 14 (64%) and indications for ECMO were respiratory failure 12 (54.5%), cardiac failure 6 (27.3%), ECPR 3 (13.6%) and sepsis 1 (4.6%).

Figure 7:
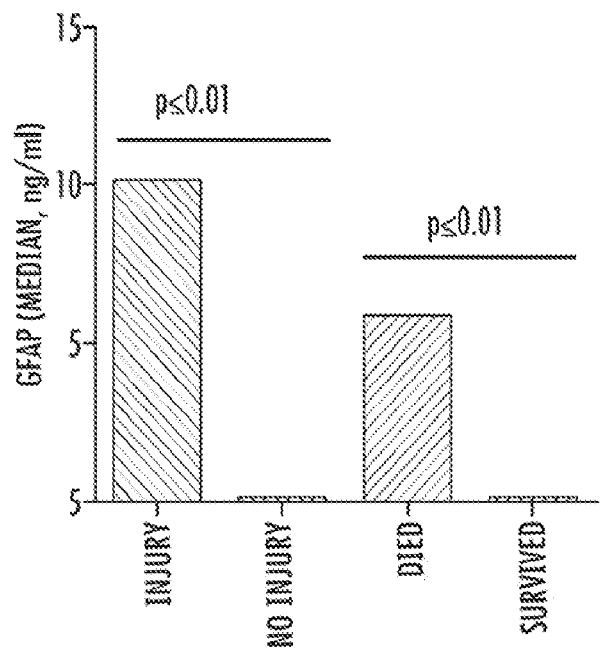
FIG. 7 shows median GFAP levels in patients on extracorporeal membrane oxygenation (ECMO) (n=22).

Median peak GFAP levels (FIG. 7) were higher in children with brain injury than those without (10.2 vs. 0.09 ng/ml, p<0.01) and in non-survivors compared to survivors at PICU discharge (5.9 vs. 0.09 ng/ml, p=0.01). Using data from all serial samples from each patient, the odds ratio (OR) for brain injury for each 1 ng/ml increase in GFAP was 1.5 (95% CI, 1.01-2.16; p=0.046). Abnormal GFAP levels (i.e., >95$^{th}$ percentile) were seen 1-2 days preceding the imaging diagnosis of 2/4 patients with severe neurologic injury or brain death. Plasma GFAP levels remained normal in three patients classified as having an acute neurologic injury based on our a priori definition, as follows: a patient with a right cerebellar hemorrhage diagnosed by head ultrasound who expired on ECMO due to non-neurologic causes, and two patients with small extra-axial hemorrhages: a patient with a small subdural hematoma who survived with good neurologic function and a patient with a grade I intraventricular hemorrhage who also survived with good neurologic function. This initial cohort of ECMO patients included three patients who underwent ECPR: one survived with good neurologic outcome and had normal GFAP levels throughout the ECMO course (median: 0.07 ng/ml, IQR: 0.05-0.09 ng/ml); one suffered a hypoxic pulseless electrical activity cardiac arrest due to status asthmaticus, evolved to brain death and showed high plasma GFAP levels (median: 27.2 ng/ml, IQR: 9.5-44.9 ng/ml) and one patient developed severe cerebral edema, eventually had withdrawal of support due to multisystem organ failure and also showed high plasma GFAP levels (median: 5.8 ng/ml, IQR: 2.8-10.5 ng/ml).

Four out of seven patients with acute neurologic injury had plasma GFAP above the 95$^{th}$ percentile for age-matched controls and 13/15 patients without acute neurologic injury diagnosed during the ECMO course had normal GFAP levels. The two patients without a diagnosis of acute neurologic injury diagnosed during ECMO but with plasma GFAP>95$^{th}$ percentile were infants with normal daily transfontanellar sonograms throughout the ECMO course. However, at 2 weeks and 6 weeks after ECMO decannulation, respectively, one patient was found to have unilateral unilobar focal enchephalomalacia consistent with a prior ischemic event and the other patient had findings of a small, old intraventricular hemorrhage and intraparenchymal hemorrhagic foci. Although exploratory, this analysis yields a receiver operating characteristic (ROC) area in acceptable range for acute neurologic injury on ECMO (0.75, 95% CI: 0.52-0.98).

The results of the present example indicate that GFAP could fill an important clinical gap as a useful diagnostic tool for acute neurologic injury on ECMO and as a predictor of outcome in this high risk group.

Example 6: GFAP as a Marker of Neurologic Injury in Neonates

Hypoxic-ischemic encephalopathy (HIE) is a subset of neonatal stroke occurring in 2.5/1000 term live births. Unfortunately intrapartum fetal monitoring and postpartum brain imaging cannot rapidly identify infants with perinatal brain injury. Importantly, neonates with moderate to severe HIE who receive head cooling within 6 hours of birth may have improved survival with diminished neurodevelopmental disability. Although therapies are being developed to treat the neonate at risk for HIE, no biomarkers are known to acutely identify specific brain injury, follow HIE therapy efficacy or to evaluate new therapies in the child at risk. A rapid test that could be done at the time of birth would be of great clinical benefit in identifying the infant at risk for HIE in order to benefit from these investigational treatments, identify therapeutic efficacy, and provide early prognostic information. Preliminary analysis of 103 prospective admissions to the neonatal intensive care unit over the past 12 months that were chromosomally normal and without major congenital malformations was conducted. Neonates with neurologic injury which included hypoxi-ischemic encephalopathy (HIE), periventricular leukomalacia, seizures, and cranial bleeding (n=27) to the non-neurologically injured neonates (n=76) were compared. These neurologically injured and non-injured neonates did not differ by gestational age (33.7±5.7 weeks injured, 33.2±4.5 weeks non-injured, p=0.67) or birth weight (2264±1129 grams injured, 1961±966 grams non-injured, p=0.18). See Table 4 below.

TABLE 4

Patient Characteristics

| | Neurologically Injured N = 27 | Non-injured N = 76 | P value |
|---|---|---|---|
| Gestational Age (weeks) | 33.7 ± 5.7 | 33.2 ± 4.5 | 0.67 |
| Birth Weight (grams) | 2264 ± 1129 | 1961 ± 966 | 0.18 |
| Cesarean Delivery (%) | 59.3 | 50.0 | 0.41 |
| Umbilical artery pH | 7.12 ± 0.18 | 7.23 ± 0.13 | 0.007* |
| Umbilical artery Base Excess (mM) | −9.7 ± 7.6 | −4.7 ± 4.8 | 0.001* |
| Cord pH<7.0 or Base Excess >−12 mM (%) | 50 | 12.1 | <0.001* |
| GFAP on day of life 1 (ng/ml) | 0.17 ± 0.19 | 0.09 ± 0.18 | 0.03* |
| GFAP on day of life 2 | 0.12 ± 0.21 | 0.15 ± 0.69 | 0.86 |

Figure 8:
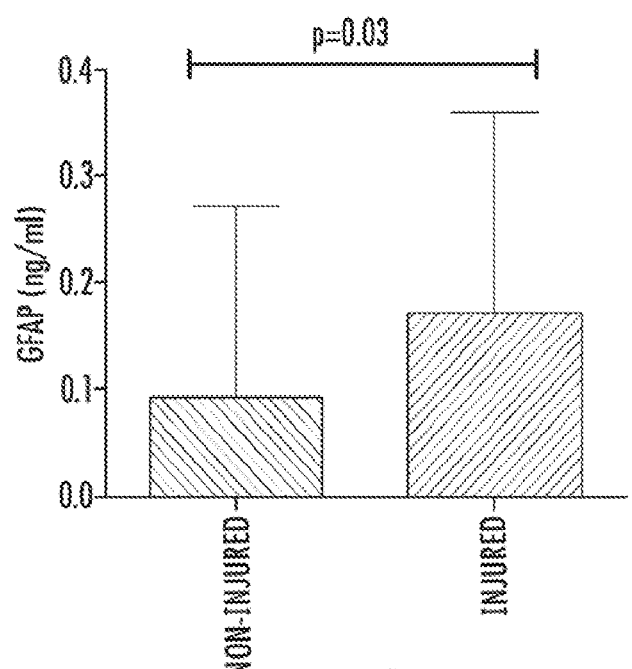
FIG. 8 shows GFAP levels on post-natal day 1 in neonates with (n=27) and without (n=76) neurologic birth injury. Values are mean±SD.
Figure 9:
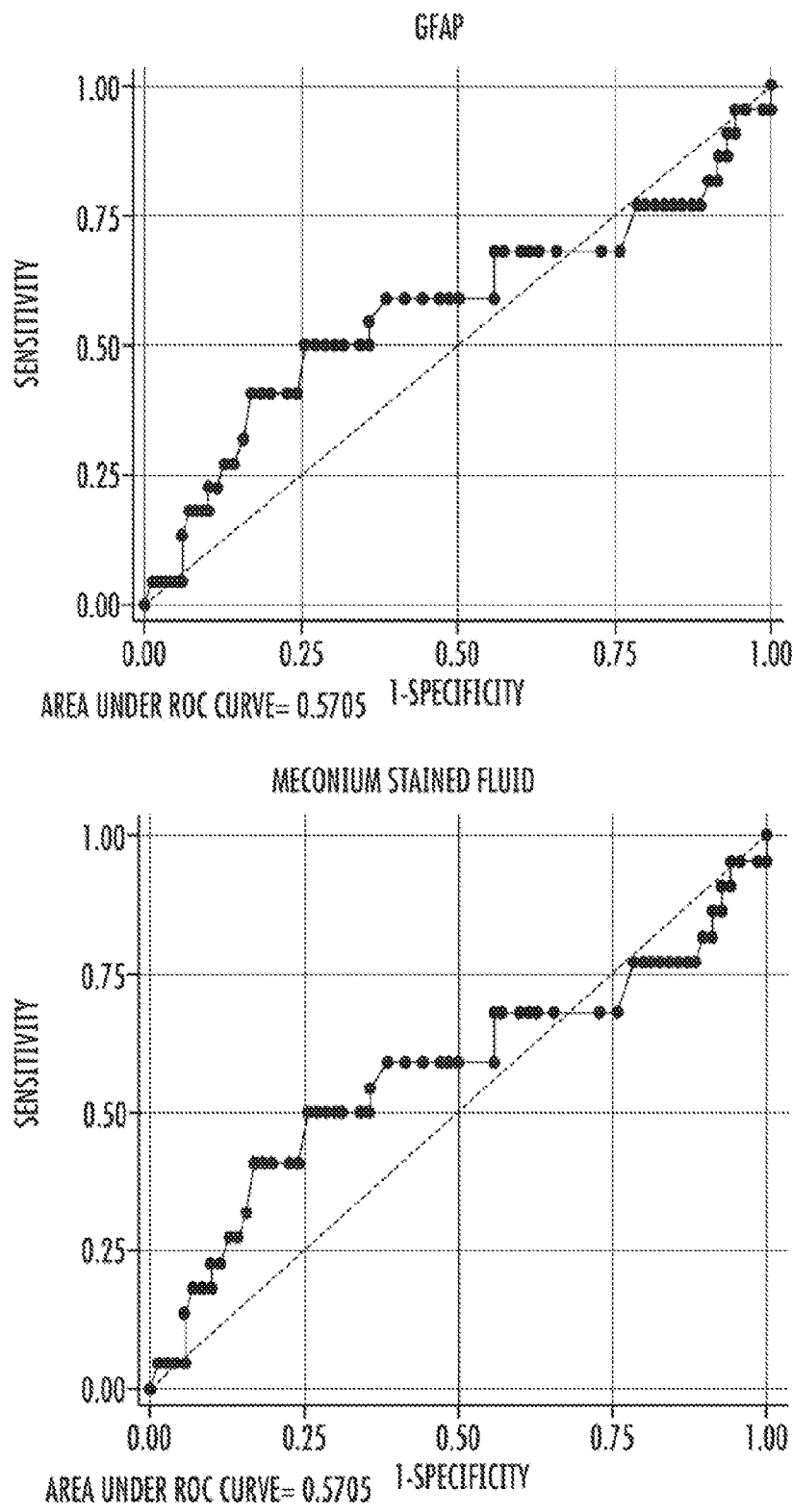
FIG. 9 presents ROC curves of GFAP vs. meconium aspiration as predictors of birth neurologic injury. Top: Logistic regression of neurologic injury related to GFAP>0.08 ng/ml within 1 day of birth matched for gestational age. Bottom: Meconium stained fluid as a predictor of neurologic injury.

Neonates with neurologic injury had significantly higher GFAP levels on the first day of life (0.17±0.19 ng/ml injured, 0.09±0.18 ng/ml non-injured, p=0.03). See Table 4 and FIG. 8. This difference in GFAP levels on the first day of life did not persist on the 2$^{nd}$ day of life (0.12±0.21 injured, 0.15±0.69 non-injured, p=0.86) likely reflecting the neurologic injury as finite and not ongoing, which is very useful information to the clinician. Receiver operator characteristic (ROC) curves (FIG. 9) were constructed to determine the optimal cutoff point of GFAP levels within 24 hours of birth to identify neurologic injury. Among neonates with GFAP levels >0.08 ng/ml the incidence of neurologic injury was 66.7% versus 36.0% among neonates with GFAP levels below this cutoff. A GFAP level >0.08 ng/ml had a higher area under the ROC curve in identifying neonatal neurologic injury than other commonly used markers for the presence of intrauterine hypoxia-ischemia such as meconium stained fluid, 5 min APGAR<7, or an umbilical arterial gas at the time of birth indicating metabolic acidosis (pH<7.0 and Base Excess <−12 mM). For example, the ROC curve for meconium stained fluid is shown in FIG. 9. Coupled with the sensitive GFAP assay, GFAP can be correlated to functional and structural neurologic injury as a consequence of birth injury. Importantly, the present example validates GFAP as a circulating marker of birth related neurologic injury.

Example 7: Glial Fibrillary Acidic Protein (GFAP) Serves as a Biomarker for Neonatal Neurologic Injury GFAP is the principal intermediate filament of the human astrocyte and is a marker specific to the central nervous system. Its appearance in a patient's serum has been found to predict neurological outcome in patients after traumatic brain injury and stroke. Brain edema following ischemia causes disruption of the blood-brain barrier, and GFAP is markedly upregulated in astrocytes in the ischemic process. The present objective was to determine if serum levels of GFAP obtained within 24 hours of birth can be used to identify neonates with neurologic injury.

A high sensitivity electrochemiluminescent assay was used to measure GFAP levels in umbilical venous blood at the time of birth and in neonatal blood on day 1 of life for neonates admitted to the neonatal intensive care unit without congenital or chromosomal abnormalities. Receiver operator characteristic (ROC) curves were constructed to determine the optimal cut-off point of GFAP levels on the first day of life to identify a composite variable of neurologic injury that included cranial bleeding and hypoxic-ischemic encephalopathy in order to determine if GFAP levels correlated with neonatal neurologic injury.

Figure 10:
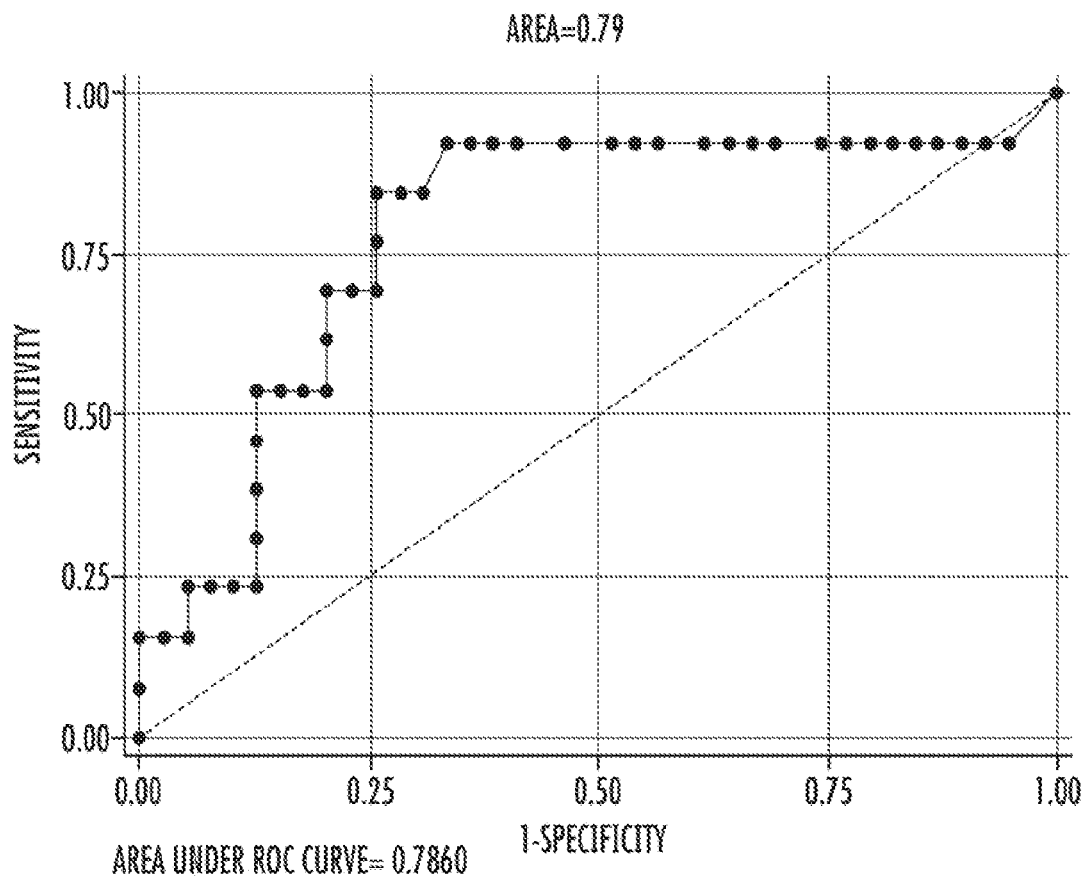
FIG. 10 shows the logistic regression of neonatal serum GFAP at admission to the NICU (Day 0).

Of the 61 neonates that met inclusion criteria, 15 had neurologic injury including 1 case of subarachnoid hemorrhage, 2 cases of subgaleal hemorrhage, 6 cases of intraventricular hemorrhage, and 6 cases of hypoxic-ischemic encephalopathy. Neonates with neurologic injury did not significantly differ in gestational age (33.2±6.2 weeks injured, 33.5±3.4 weeks non-injured), birth weight (2326±1379 grams, 2031±918 grams) or incidence of cesarean delivery (41.2%, 54.5%). GFAP levels at birth in cord blood were 0.16±0.23 ng/ml injured, 0.09±0.11 ng/ml non-injured, p=0.26; and on day 1 of life were 0.12±0.06 ng/ml injured, 0.09±0.12 ng/ml non-injured, p=0.40. Seventeen patients had elevated GFAP levels above the optimal cutoff point of 0.08 ng/ml which had an area under the ROC curve of 0.81 (p<0.001) in the identification of neurologic injury. Neurologic injury was significantly more common in the elevated GFAP group (68.8%) than in those with normal GFAP levels (10.0%, p=0.02). See FIG. 10.

Further validation of the finding of elevated serum GFAP levels, alone or in aggregate with other clinical markers, at the time of birth or early during the neonatal period, may help identify infants at risk for neurologic injury for appropriate triaging of patients for early therapies and entry into therapeutic trials for these at risk infants.

Example 8: Ability of GFAP to Detect Neurologic Injury in Pediatric Patients with Cardiac Disease on ECMO Children undergoing cardiopulmonary bypass (CPB) experience neurologic injury in 30-70% of cases. See McQuillen et al., 38 STROKE 736-41 (2007); and Mahle et al., 106 CIRCULATION I-109-I-114 (2002). Extracorporeal membrane oxygenation (ECMO) represents a similar support modality with a risk of neurologic injury in 10-60% of cases. See Cengiz et al., 33(12) CRIT. CARE MED. 2817-24 (2005); and Ibrahim et al., 69(1) ANN. THORAC. SURG. 186-92 (2000). It is hypothesized that a brain specific protein, glial fibrillary acidic protein, (GFAP), could serve as a plasma biomarker for neurologic injury in these vulnerable patients while on ECMO.

As part of a prospective study of pediatric patients on ECMO, only those patients with history of critical cardiac disease and ECMO were included in this evaluation. Demographic information such as age, diagnosis, duration of ECMO and outcome at time of PICU discharge was recorded. Serial blood samples during the ECMO course were evaluated for GFAP using an electroluminescent assay developed at our institution.

A total of 7 children with critical cardiac disease were enrolled. Median duration of ECMO support was 5.2 days (range: 1 to 12 days). The 2 children who underwent ECMO post-CPB had GFAP levels similar to other children who underwent ECMO only. One patient who experienced acute neurologic injury had plasma GFAP levels that were 100-fold greater than those without neurologic injury; the increase in plasma GFAP coincided with detection of neurologic injury by imaging. The plasma GFAP levels during the ECMO course for each patient are shown in Table 5 below.

| Diagnosis | pt | GFAP Measurements | | | | | | CPB XC | Neuro Injury | Survival |
|---|---|---|---|---|---|---|---|---|---|---|
| | | 1 | 2 | 3 | 4 | 5 | 6 | | | |
| Heart transplant for DCM s/p bivad, inabilty to separate from CPB | A | 0.074 | 0.43 | 11.3 | 20.5 | | | 400 min 69 min | Stroke, ICH | No |
| Dilated Cardiomyopathy | B | 0.052 | <0.04 | 0.053 | | | | | None | Yes |
| Dilated Cardiomyopathy | C | 0.162 | <0.04 | <0.04 | | | | | None | Yes |
| AS, M S | D | <0.04 | <0.04 | | 0.06 | 0.07 | 0.19 | | None | Yes |
| PPHN D-TGA, POD #1 s/p BAS | E | <0.04 | <0.04 | 0.083 | 0.16 | | | | None | Yes |
| Cardiogenic shock s/p PA stenting, h/o TOF, RV-PA conduit | F | 0.068 | 0.09 | 0.054 | | | | | None | Yes |
| POD #3 RV-PA Conduit for TA, hypoxemia | G | <0.04 | <0.04 | | | | | 201 min 130 min | None | Yes |

Abbreviations:
pt—patient,
XC—cross clamp,
Neuro—neurologic,
DCM—dilated cardiomyo-pathy,
bivad—biventricular assist device,
min—minutes,
ICH—intracranial hemorrhage,
AS—aortic stenosis,
MS—mitral stenosis,
PPHN—persistent pulmonary hypertension of the newborn,
D-TGA—dextro-transposition of the great arteries,
POD—post-operative day,
BAS—balloon atrial septostomy,
PA—pulmonary artery,
TOF—tetralogy of fallot,
RV—right ventricle,
TA—truncus arteriosus.

Plasma GFAP appears to correlate with neurologic injury in this series of patients with critical heart disease on ECMO. This may aid in detection of neurologic injury in patients on ECMO and during CPB.

Example 9: GFAP is Elevated During Cardiopulmonary Bypass for Repair of Congenital Heart Disease Brain injury, manifested as stroke, abnormalities on brain MRI, and neurodevelopmental deficits occur in 30% to 70% of infants after surgical correction of congenital heart defects (CHD). See Andropoulos et al., 139 J. THORAC. CARDIOVASC. SURG. 543-56 (2010); and McQuillen et al., 38 STROKE 736-41 (2007). A study of neonatal repairs of one and two ventricle CHD (n=62) reported 39% of patients had injury preoperatively (predominately stroke) and 35% had new lesions post-operatively. See McQuillen et al., 38 STROKE 736-41 (2007). The present inventors have examined whether GFAP could serve as diagnostic/prognostic biomarker of brain injury during cardiopulmonary bypass for surgical repair of congenital heart disease. Cardiopulmonary bypass serum samples were obtained before, during (every 30 minutes) and after from 20 consecutive infants (2 days-3 months) undergoing cardiopulmonary bypass for surgical repair of congenital heart disease.

Figure 11:
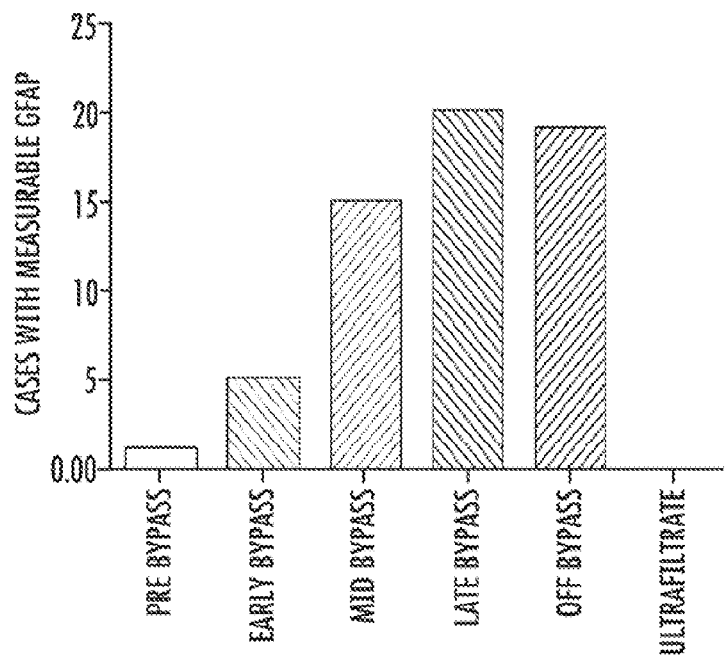
FIG. 11 is a graph displaying serum GFAP levels during cardiopulmonary bypass for repair of congenital heart disease, n=20.
Figure 12:
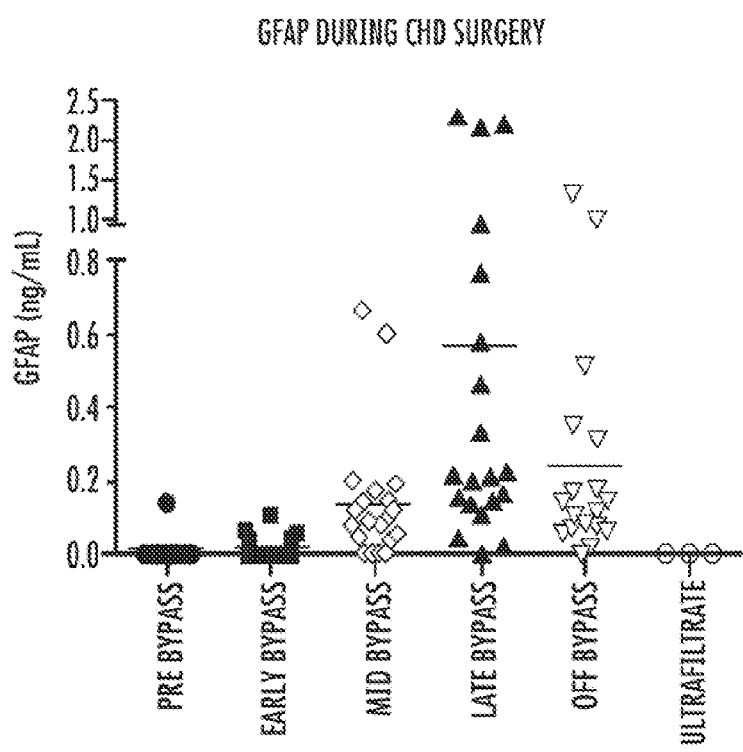
FIG. 12 is a graph displaying serial serum GFAP levels during cardiopulmonary bypass for repair of congenital heart disease, n=20.

As shown in FIG. 11, the number of cases with quantifiable GFAP levels increase as bypass progresses, beginning in the first hour of bypass (Early Bypass) and peaking at the end of bypass (Late Bypass). Only one case had a quantifiable GFAP level prior to bypass with all 20 cases having measurable values at the end of bypass. As shown in FIG. 12, levels of GFAP are significantly increased in the Mid, Late and Off bypass periods ($p<0.05$, $p<0.001$ and $p<0.001$, respectively when compared to pre- and early bypass levels). The magnitude of elevation in 4 of the cases is equivalent to levels seen with overt stroke (0.5-2.5 ng/ml). Two of these 4 infants had a post-operative brain MRI and were confirmed to have an acute stroke. See also FIG. 13.

This data provides further evidence for GFAP as a sensitive blood biomarker of brain injury in infants. In addition, it demonstrates that body cooling to 18° C. does not prevent significant GFAP release into the circulation. Like neonates cooled for HIE, GFAP levels peak with re-warming (late bypass period), implying that re-warming is a time of increased vulnerability to injury.

Example 10: GFAP as a Brain Injury Biomarker in Children Undergoing Extracorporeal Membrane Oxygenation The objective of this study was to determine whether, in children, plasma glial fibrillary acidic protein is associated with brain injury during extracorporeal membrane oxygenation and with mortality. Prospective patients age 1 day to 18 yrs who required extracorporeal membrane oxygenation from April 2008 to August 2009 were studied. Glial fibrillary acidic protein was measured using an electrochemiluminescent immunoassay developed at Johns Hopkins Control samples were collected from 99 healthy children (0.5-16 yrs) and 59 neonatal intensive care unit infants without neurologic injury. In controls, the median glial fibrillary acidic protein concentration was 0.055 ng/ml (interquartile range, 0-0.092 ng/ml) and the 95th percentile of glial fibrillary acidic protein was 0.436 ng/ml. In patients on extracorporeal membrane oxygenation, plasma glial fibrillary acidic protein was measured at 6, 12, and every 24 hrs after cannulation. Twenty-two children who underwent extracorporeal membrane oxygenation were enrolled. Median age was 7 days (interquartile range, 2 days to 9 yrs), and primary extracorporeal membrane oxygenation indication was: cardiac failure, six of 22 (27.3%); respiratory failure, 12 of 22 (54.5%); extracorporeal cardiopulmonary resuscitation, three of 22 (13.6%); and sepsis, one of 22 (4.6%). Seven of 22 (32%) patients developed acute neurologic injury (intracranial hemorrhage, brain death, or cerebral edema diagnosed by imaging). Fifteen of 22 (68%) survived to hospital discharge. In the extracorporeal membrane oxygenation group, peak glial fibrillary acidic protein levels were higher in children with brain injury than those without (median, 5.9 vs. 0.09 ng/ml, $p=0.04$) and in non-survivors compared with survivors to discharge (median, 5.9 vs. 0.09 ng/ml, $p=0.04$). The odds ratio for brain injury for glial fibrillary acidic protein >0.436 ng/ml vs. normal was 11.5 (95% confidence interval, 1.3-98.3) and the odds ratio for mortality was 13.6 (95% confidence interval, 1.7-108.5).

High glial fibrillary acidic protein during extracorporeal membrane oxygenation is significantly associated with acute brain injury and death. Brain injury biomarkers may aid in outcome prediction and neurologic monitoring of patients on extracorporeal membrane oxygenation to improve outcomes and benchmark new therapies.

Materials and Methods

Study Design.

This study was a prospective observational cohort study of children who underwent ECMO in a 26-bed pediatric intensive care unit of a single tertiary care, academic pediatric center from April 2008 to August 2009. Patients <18 yrs who required ECMO for any indication were eligible for this study. This cohort was initiated for the study of coagulation-related risk factors for neurologic injury during ECMO with a secondary aim to investigate brain injury biomarkers in this population. Exclusion criteria were history of heparin-induced thrombocytopenia and use of direct thrombin inhibitors for anticoagulation during ECMO. Parents or legal guardians were approached for consent after patient stabilization, within the first 6 hrs after ECMO cannulation, only when present in the pediatric intensive care unit. No consent was conducted over the phone. Demographic, clinical, laboratory, imaging, and survival data were collected for each enrolled subject. The ECMO circuit consisted of: custom-packed one-fourth- or three-eighths-inch flexible polyvinylchloride tubing (Medtronic, Minneapolis, Minn.) with a silicone reservoir, a bladder box (Johns Hopkins Hospital, Baltimore, Md.), a 0.8-$m^2$ to 4.5-$m^2$ membrane oxygenator (Medtronic), a heat exchanger (Medtronic), and a roller pump (Sorin Cardiovascular USA, Arvada, Colo.). This study was approved by the Johns Hopkins Institutional Review Board.

Biomarker Sampling and Analysis.

Venous blood samples (5 ml in sodium citrate 3.2%) were collected at 6, 12, and 24 hrs after initiation of ECMO and then daily until ECMO discontinuation. After separation by centrifugation within 1 hr, platelet-poor plasma was stored at −80° C. Fifty microliters were used for GFAP measurements in undiluted duplicate plasma samples using an electrochemiluminescent sandwich immunoassay developed on the MesoScale Discovery platform (MesoScale Discovery, Gaithersburg, Md.) at Johns Hopkins University and based on the assay of Petzold et al., 287 J. IMMUNOL. METHODS 169-77 (2004). The monoclonal anti-GFAP blend SMI-26 (Covance, Princeton, N.J.) was used at 100 ng per well as capture antibody in standard bind plates (MesoScale Discovery) coated either by the manufacturer or in the laboratory with overnight incubation in phosphate-buffered saline. Polyclonal anti-GFAP (Dako, Carpinteria, Calif.) that was directly conjugated with Sulfo-Tag (MesoScale Discovery) was used for detection at 1 µg/ml in phosphate-buffered saline. Plates were read with a Sector Imager 2400 (MesoScale Discovery). Standard curves were constructed with purified GFAP (Calbiochem, La Jolla, Calif.) in 1% bovine serum albumin (SeraCare Life Sciences, Milford, Mass.). After experiments to determine the optimal antibody concentrations, plate type, and blocking material, the final assay for GFAP values had a standard curve with a linear range of quantification from 0.040-40.0 ng/ml. The present GFAP assay had a lower limit of detection of 0.011 ng/ml as defined by two SDs above the background of blank wells (n=19 experiments). Values <0.040 ng/ml were reported as zero. The signal-to-noise ratio was 1.17 at 0.01 ng/ml (n=19 experiments). The lower limit of quantification, defined as the lowest dilution with a calculated concentration±20% of a known concentration, was 0.040 ng/ml (n=3 experiments). Interassay precision was 2.4% at 10 ng/ml and 3.4% at 0.156 ng/ml (n=21 experiments). Plasma spiked with GFAP shows 49.8%±22.9% recovery at 10 ng/ml when compared with a standard curve generated in bovine serum albumin. Validation of the GFAP assay was conducted using discarded diagnostic specimens from normal and positive controls. This GFAP assay validation study was approved in a separate application by the Johns Hopkins Institutional Review Board with a waiver of consent.

Outcome Measures.

The primary independent variable was plasma GFAP elevation above the 95th percentile of normal values in children. The primary outcome was development of acute neurologic injury during ECMO, defined as intracranial hemorrhage, brain infarction, or cerebral edema diagnosed by brain imaging and/or neurologic examination by a pediatric neurologist consistent with brain death while the patient was on ECMO support. It is institutional protocol to obtain daily head ultrasounds for newborns and infants with open fontanelles; older children had brain computed tomography or magnetic resonance imaging studies obtained at the discretion of their physicians. All imaging studies were reviewed by pediatric radiologists as part of routine clinical care. The secondary outcomes were neurologic outcome and survival to discharge from the hospital. Neurologic outcome was measured using the pediatric cerebral performance category (PCPC). See Fiser et al., 28 CRIT. CARE MED. 2616-20 (2000); and Fiser et al., 121 J. PEDIATR. 68-74 (1992). The PCPC is a 6-point scale developed from the Glasgow Outcome Scale to assess changes in cognitive abilities in pediatric intensive care. The six PCPC categories are 1) normal, age-appropriate neurodevelopmental functioning; 2) mild cerebral disability, 3) moderate cerebral disability; 4) severe cerebral disability; 5) coma or vegetative state, and 6) brain death. See Fiser et al., 28 CRIT. CARE MED. 2616-20 (2000); and Fiser et al., 121 J. PEDIATR. 68-74 (1992). A trained pediatric critical care physician assigned PCPC retrospectively by conducting a chart review of the patient's condition at admission to the hospital and at discharge from the hospital. Good neurologic outcome was defined a priori as PCPC of 1 or 2 at discharge from the hospital or no change from PCPC at hospital admission.

Statistical Analysis.

Exploratory descriptive data analysis was conducted to examine patient and ECMO course characteristics, to describe the distribution of GFAP values among subjects, and to determine the proportion of subjects in whom GFAP levels were above the 95th percentile. The Kruskal-Wallis test was used to compare GFAP concentrations across age categories in normal controls. Patients were divided into two categories for each outcome: those with and without acute neurologic injury, good vs. poor neurologic outcomes at hospital discharge, and survivors vs. non-survivors at hospital discharge. The Mann-Whitney U test was used to compare the median peak GFAP between these groups. Fisher's exact test was used to compare percent of cases above and below 95th percentile of peak GFAP between the groups. Logistic regression with clustering by patient was used to estimate odds of brain injury and death using all serial GFAP data points. For the clustered analysis, subjects were coded as having no acute neurologic injury until brain injury by imaging or a first neurologic examination consistent with brain death was observed. Subsequent observations were coded as having acute neurologic injury. The odds ratio (OR) and 95% confidence intervals (CIs) are provided. A p value of 0.05 was considered significant. Statistical analysis was conducted using STATA 10.0 (StataCorp, College Station, Tex.).

Results

Patient Characteristics.

Twenty-two of 46 eligible patients were enrolled; 18 patients' parents were not present in the pediatric intensive care unit or it was not possible to conduct a full consent discussion during the 6-hr consent window, five parents declined consent, and one patient had no samples available for testing. Demographic and clinical characteristics of the 22 evaluated patients are presented in FIG. 14.

Individual patient characteristics and outcomes are presented in FIG. 15. Seven of 22 patients (31.8%) had an acute neurologic injury during ECMO based on an a priori definition. Using baseline and discharge PCPC, 14 of 22 (63.6%) patients had a good neurologic outcome and eight of 22 (36.4%) patients had a poor neurologic outcome; one had a PCPC>2 and seven died. Causes of death included brain death (one patient), large intracranial hemorrhage (two patients), and withdrawal of mechanical support for medical futility in the face of irreversible multisystem organ failure (four patients).

The median duration of ECMO was 12 days (interquartile range [IQR], 5-17 days). The median number of GFAP measurements per patient was 4.5 (range, 1-16). Seventeen patients had three or more measurements, three patients had two measurements, and two patients had only one measurement.

GFAP Results: Controls.

In normal pediatric controls with no known neurologic injury, GFAP levels had a median of 0.055 ng/ml (IQR, 0-0.092 ng/ml). GFAP levels were similar across age categories (newborns: median 0.041 ng/ml [IQR, 0-0.096 ng/ml], 6 months to 4 yrs: median 0.046 ng/ml [IQR, 0-0.117 ng/ml], 5-16 yrs: median 0.057 ng/ml [IQR, 0-0.088 ng/ml], p=0.7). A 95th percentile cutoff for normal values in children (plasma GFAP≤0.436 ng/ml) was determined using samples from 158 infants and children: 59 newborns <4 days of life in the neonatal intensive care unit without known genetic disorders or intracranial pathology and 99 healthy children 6 months to 16 yrs of age who presented to the Johns Hopkins pediatric outpatient clinic for well-child visits. The assay was further validated for the detection of neurologic injury in patients with brain tumor resection (n=13), brain biopsy (n=3), and stroke (n=12). GFAP levels in positive controls samples were overall one- to 55-fold higher than for normal controls.

GFAP Results: Patients on ECMO.

The median initial GFAP level within 12 hrs after starting ECMO was 0.07 ng/ml (IQR, 0-0.155 ng/ml). There were three of 22 patients with abnormal GFAP concentrations in the first 24 hrs after cannulation; two were patients who sustained cardiac arrest and underwent ECPR with venoarterial cannulation of right neck vessels and one was a patient without known neurologic injury who was placed on venovenous ECMO through a double-lumen right jugular vein cannula. All other 19 of 22 patients had low GFAP levels in the first 24 hrs after cannulation. The median GFAP level on the last ECMO day for those children with three or more samples was 0.07 ng/ml (IQR, 0.053-0.795 ng/ml; n=17). Peak GFAP concentrations were similar comparing newborns with children and infants >30 days (0.155 ng/ml vs. 0.162 ng/ml, respectively, p=0.48).

Figure 16:
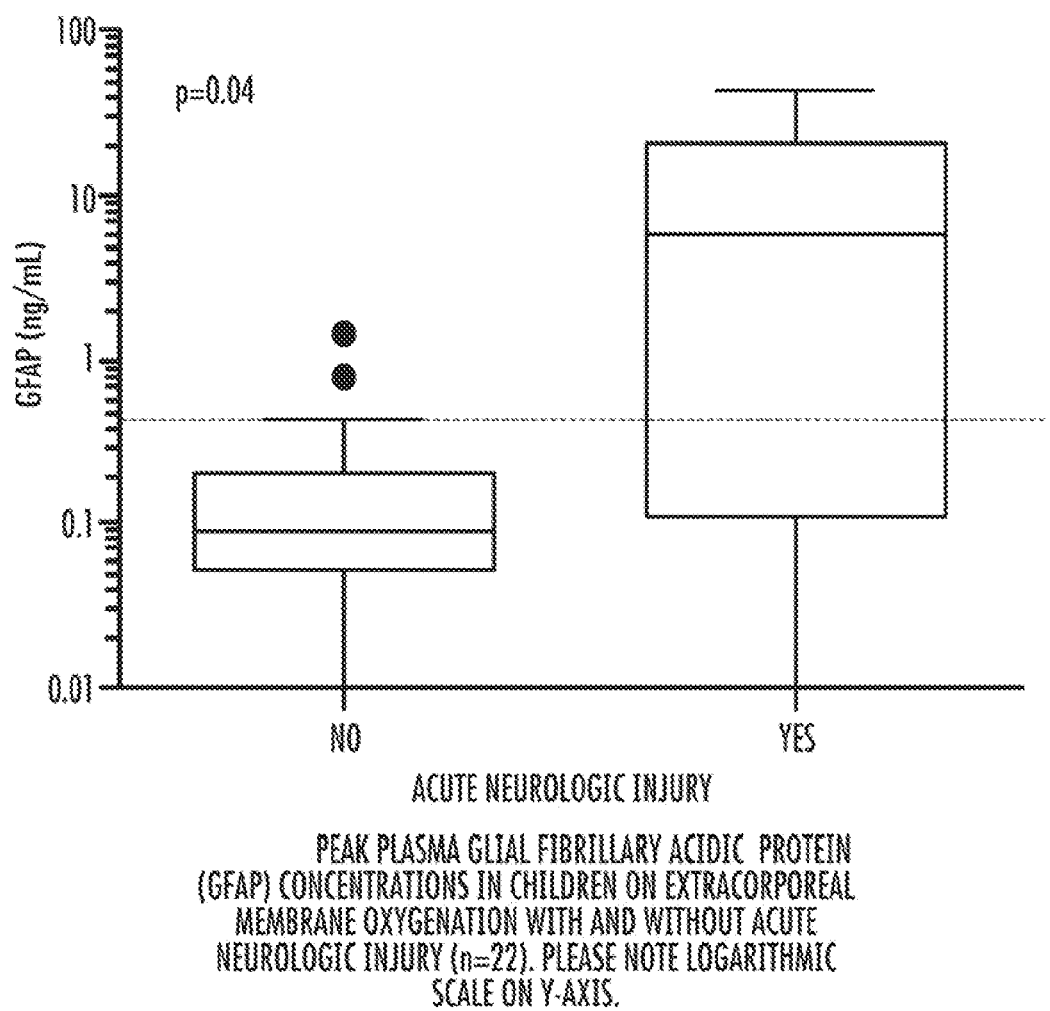
FIG. 16 shows peak plasma GFAP concentrations in children on ECMO with and without acute neurologic injury (n=22). Note logarithmic scale on y-axis.

Median peak GFAP levels were significantly higher in children with acute neurologic injury diagnosed during the ECMO course than those without (5.9 vs. 0.09 ng/ml, p=0.04) (FIG. 16), in children with poor vs. good neurologic outcome (3.6 ng/ml vs. 0.09 ng/ml, p=0.01), and in non-survivors compared with survivors to hospital discharge (5.9 ng/ml vs. 0.09 ng/ml, p=0.04). Serial GFAP concentrations in patients with and without acute neurologic injury are displayed in FIG. 17.

Peak plasma GFAP concentrations >95th percentile for normal controls (i.e., >0.436 ng/ml) were noted in six of 22 (27.3%) patients. The proportion of patients with acute neurologic injury was higher in patients with peak GFAP>0.436 ng/ml than in those with peak GFAP≤0.436 ng/ml (four of six [66.7%] vs. three of 16 [18.8%]; p=0.054). Poor neurologic outcome was seen more frequently in patients with peak GFAP>0.436 ng/ml than in those with normal GFAP measurements (five of six [83.3%] vs. three of 16 [18.8%]; p=0.01). Similarly, hospital mortality was higher in patients with peak GFAP>0.436 ng/ml than in those with normal GFAP measurements (four of six [66.7%] vs. three of 16 [18.8%], p=0.054).

To account for repeated measures per patient, the association of all 126 serial GFAP levels with the outcomes was evaluated using logistic regression clustered by patient. The odds of acute neurologic injury given elevated GFAP (>0.436 ng/ml) were 11.5 (95% CI, 1.3-98.3). Similar statistically significant results were found for poor neurologic outcome (OR, 25.7; 95% CI, 2.2-298.5) and hospital mortality (OR, 13.6; 95% CI, 1.7-108.5).

After adjusting for neonatal status (≤30 days), the odds of acute neurologic injury remained significantly higher in patients with abnormally elevated plasma GFAP compared with patients with normal GFAP (adjusted OR, 15.7; 95% CI, 1.8-139.9). In the subgroup of 17 newborns and infants who had daily head ultrasounds performed throughout the duration of ECMO, the unadjusted OR for acute neurologic injury was 22.3 (95% CI, 2.0-245.9).

Although exploratory, this analysis yields an area under receiver operating characteristic curve in an acceptable range for acute neurologic injury (area under receiver operating characteristic curve, 0.72; 95% CI, 0.50-0.94), poor neurologic outcome (area under receiver operating characteristic curve, 0.78; 95% CI, 0.58-0.97), and death (area under receiver operating characteristic curve, 0.72; 95% CI, 0.50-0.94).

Figure 17A:
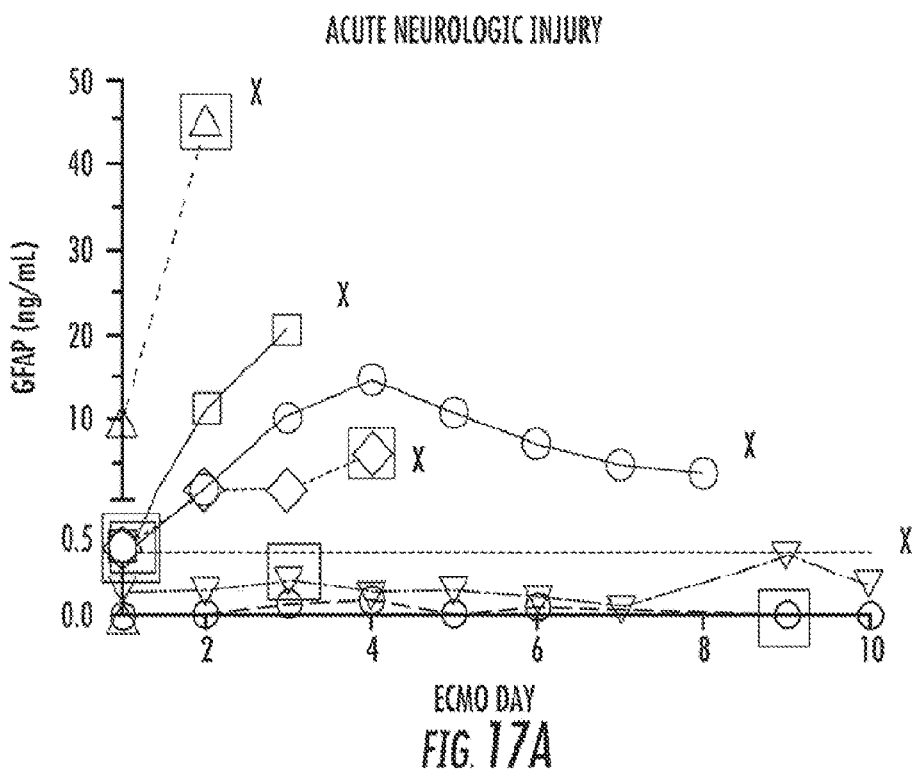
FIG. 17A shows serial plasma GFAP concentrations in children on ECMO with acute neurologic injury (n=7). X represents death in the pediatric intensive care unit; open squares represent the time of diagnosis of acute neurologic injury closest in time (within 24 hrs) to the last GFAP measurement; dashed line marks the 95th percentile of normal controls. Note only six open squares; one patient had a diagnostic head ultrasound 48 hrs after the only GFAP measurement (GFAP measurement 24 hrs before diagnosis is missing).
Figure 17B:
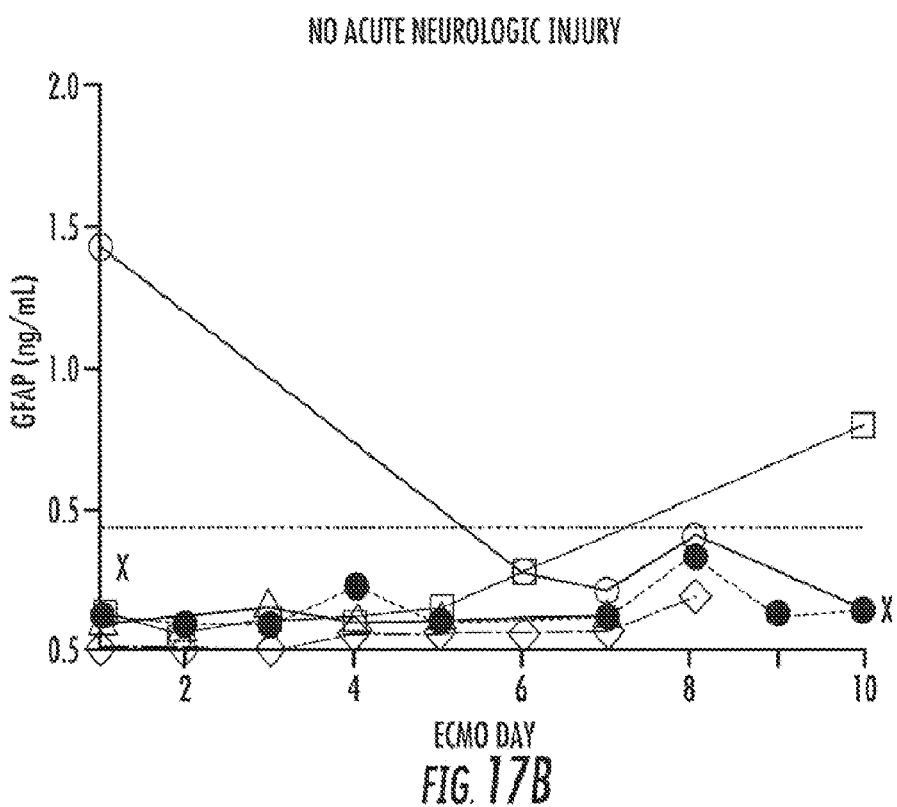
FIG. 17B shows serial plasma GFAP concentrations in children on ECMO without acute neurologic injury (n=15). X represents death in the pediatric intensive care unit; dashed line marks the 95$^{th}$ percentile of normal controls. Note the different scales in A and B.

Elevations in GFAP correlated temporally with the imaging diagnosis of brain injury during ECMO. Abnormal GFAP levels (>0.436 ng/ml) were observed 1-2 days before the imaging diagnosis of severe acute neurologic injury or brain death in two of four patients. GFAP levels remained normal in three patients with acute neurologic injury diagnosed by head ultrasound during ECMO, including a patient with a small subdural hematoma and good neurologic function at discharge (PCPC=1), a patient with grade I intraventricular hemorrhage and good neurologic function at discharge (PCPC=1), and a patient with a small right cerebellar hemorrhage who developed multisystem organ failure and ultimately died (FIG. 17). Although it can be speculated that in the first two patients no elevations in GFAP were found because the lesions were minor and extraparenchymal in location, no good explanation exists for a lack in GFAP "response" to a cerebellar intraparenchymal hemorrhage in the third patient. Of note, cause of death in this latter patient was not related to neurologic injury but rather to multisystem organ failure and withdrawal of support resulting from medical futility.

There were two patients without a diagnosis of acute neurologic injury during ECMO but with peak GFAP>95th percentile on the first and the tenth day of ECMO, respectively (FIG. 17). These were newborns with normal daily head ultrasounds throughout the ECMO course. However, at 6 wks and 2 wks after ECMO decannulation, respectively, one patient was found to have small old intraventricular and intraparenchymal hemorrhagic foci and the other had findings of unilateral unilobar focal encephalomalacia consistent with a prior ischemic event on brain magnetic resonance imaging.

This initial cohort of ECMO patients included three patients who underwent ECPR; one survived with a good neurologic outcome and had normal GFAP levels throughout the ECMO course (median GFAP, 0.07 ng/ml; IQR, 0.05-0.09 ng/ml); two patients had poor outcomes: one sustained a hypoxic pulseless electrical activity cardiac arrest as a result of status asthmaticus and evolved to brain death (median GFAP, 27.2 ng/ml; IQR, 9.5-44.9 ng/ml) and one patient developed severe cerebral edema, was successfully decannulated from ECMO, but eventually support was withdrawn for multisystem organ failure and medical futility (median GFAP, 5.8 ng/ml; IQR, 2.8-10.5 ng/ml).

Discussion

ECMO is a procedure with high risk for brain injury, including intracranial hemorrhage, brain infarction, and brain death. Cengiz et al., 33 CRIT. CARE MED. 2817-24 (2005); Conrad et al., 51 ASAIO J. 4-10 (2004); and Cilley et al., 78 PEDIATRICS 699-704 (1986). The means for timely assessment of such injuries in patients on ECMO are often lacking. Although acute neurologic insult is of great concern in critically ill patients, no brain injury biomarker is available yet for routine clinical practice, although many coordinated efforts are ongoing. See Kaneko et al., 80 RESUSCITATION 790-94 (2009); and Laskowitz et al., 40 STROKE 77-85 (2009). The plasma GFAP biomarker used in this study has many advantages such as high specificity to brain, easy to obtain samples for small blood volumes, fast processing, precise quantification, low cost, and minimal technical expertise required for the assay. Serial GFAP measurements could thus be used to monitor neurologic status and response to potential neuroprotective interventions, aid in the prompt diagnosis of acute brain injury, and predict outcomes.

This study demonstrates that plasma concentrations of GFAP are associated with brain injury in children on ECMO. Serial GFAP concentrations appeared stable over time in the absence of neurologic insults and were significantly elevated in patients who were diagnosed with brain injury during ECMO. The majority of patients (19 of 22) had normal GFAP levels in the first 24 hrs after ECMO cannulation, suggesting that cannulation of the right jugular vein±the right carotid artery is not accompanied by injury leading to reactive gliosis and GFAP elevations. GFAP concentrations were elevated in four patients before a diagnosis of brain injury; two patients were diagnosed with acute neurologic injury while on ECMO and two patients had imaging evidence of prior brain ischemia or hemorrhage after ECMO decannulation. This may be particularly important for infants with intraparenchymal lesions that cannot be detected by transfontanellar sonography, thus providing false reassurance to clinicians.

Acute neurologic injury is found more frequently in patients undergoing ECPR compared with ECMO for other indications. See Barrett et al., 10 PEDIATR. CRIT. CARE MED. 445-51 (2009); and Conrad et al., 51 ASAIO J. 4-10 (2004). Recent studies report 73% survival to hospital discharge in pediatric patients undergoing ECPR with 75-78% of survivors having favorable neurologic outcomes. See Barrett et al., 10 PEDIATR. CRIT. CARE MED. 445-51 (2009); and Prodhan et al., 80 RESUSCITATION 1124-29 (2009). Acute neurologic injury occurs in 22% of pediatric patients undergoing ECPR; of these, 89% die before hospital discharge. Barrett et al., 10 PEDIATR. CRIT. CARE MED. 445-51 (2009). In the present study, normal serial GFAP levels were found in one patient who underwent ECPR and survived with good neurologic outcome. In contrast, two children who underwent ECPR and subsequently developed severe hypoxic brain injury had plasma GFAP levels 20-100 times higher than the 95th percentile for normal children. To the present inventors' knowledge, this is the first report of plasma GFAP as a potential predictive biomarker for ECPR; two prior studies of GFAP after cardiac arrest excluded patients who underwent ECPR. See Hayashida et al., 12(2) NEUROCRIT. CARE 252-57 (2010); and Kaneko et al., 80 RESUSCITATION 790-94 (2009). However, these data are very preliminary and no further inferences can be made at this time.

Example 11: GFAP as a Biomarker for Neonatal Hypoxic-Ischemic Encephalopathy Treated with Whole-Body Cooling Subjects.

This is an institutional review board-approved prospective cohort study that examined neonates admitted to the neonatal intensive care unit (NICU) at a single tertiary university hospital. Subjects were live-born, non-anomalous, non-syndromic infants born at 36-41 weeks' gestation. This study included neonates born at Johns Hopkins as well as those born within the state of Maryland and transported to the NICU within 6 hours of birth.

Records were reviewed to abstract clinical information available at the time of maternal and neonatal discharge. Preeclampsia was defined as proteinuria and new-onset hypertension. Administration of intravenous magnesium sulfate to the mother prior to delivery was recorded because this therapy has been linked with a reduced risk of neonatal brain injury. Rouse et al., 359 N. ENGL. J. MED. 895-905 (2008). Intrauterine growth restriction was defined as an estimated fetal weight less than the 10th percentile for gestational age. Hadlock et al., 181 RADIOLOGY 129-33 (1991). Non-reassuring fetal heart rate tracings were those significant enough to prompt operative vaginal or cesarean delivery. Sepsis was considered present only for neonates with positive blood and/or cerebrospinal fluid cultures.

Neonates with moderate to severe encephalopathy that met criteria for whole body cooling were compared with neonates without neurologic injury admitted to the NICU matched by gestational age within 1 week in a 1:1 fashion. Shankaran et al., 353 N. ENGL. J. MED. 1574-84 (2005); and Sarnat et al., 33 ARCH. NERUOL. 696-705 (1976). Neonates of 36 weeks' gestation or longer that qualify are cooled using a conductive water-based hypothermia system and hypothermia blankets within 6 hours of birth and are kept at a rectal temperature of 33.5° C. for 72 hours.

Routinely all neonates with HIE treated with whole-body cooling have a standard neonatal imaging brain MRI prior to discharge from the NICU. For this study, these images were reviewed by an experienced pediatric neuroradiologist (T.A.G.M.H.) blinded to the GFAP results.

Neonates with an abnormal brain MRI were compared with those whose brain MRI was normal. The images were reviewed for focal or diffuse lesions related to hypoxic ischemic injury. MRI brain abnormalities were defined as brain swelling; cortical highlighting; focal or global loss of gray-white matter differentiation; abnormal signal intensity in the basal ganglia and thalami; loss of normal signal intensity in the posterior limb of the internal capsule; acute and subacute parenchymal, intraventricular, or extracerebral hemorrhage; and acutely evolving focal infarction in an arterial territory or in a parasagittal or watershed distribution. See Cowan et al., 361 LANCET 736-42 (2003).

Specimens.

Specimens collected for measurement of GFAP included umbilical cord blood and neonatal serum. For the umbilical cord blood, a small aliquot was taken from the umbilical cord venous blood sample routinely collected at delivery. For neonatal samples, the remaining fraction of serum from daily laboratory tests was collected after clinically indicated testing was completed. Neonatal serum specimens were collected at the time of admission to the NICU (within 6 hours of birth) and then daily for the first 4 days of life for the non-neurologically injured controls and daily for 7 days for neonates with HIE that underwent whole-body cooling.

GFAP Assay.

Using the Mesoscale platform (MesoScale Discovery, Gaithersburg, Md.), an electrochemiluminescent sandwich immunoassay was developed for GFAP. See Pelinka et al., 57 J. TRAUMA 1006-12 (2004). This was developed after the method of Petzold et al. using a trio of mouse monoclonal antibodies for capture and a rabbit polyclonal for detection. See Bembea et al., 11 PEDIATR. CRIT. CARE MED. 723-30 (2010); and Petzold et al., 287 J. IMMUNOL. METHODS 169-77 (2004). Serum samples were assayed in duplicate, and the mean concentration was used for analysis. The lower limit of quantitation was 0.04 ng/ml; values below this were reported as zero.

Statistical Analysis.

Comparisons were made using a $\chi^2$ or Fisher's exact test for categorical variables and unpaired Student t test for continuous variables. GFAP levels were compared using the Wilcoxon rank-sum test for nonparametric data. Significance was set at $P<0.05$. Linear regression was used to determine the effect of gestational age on GFAP level in the non-neurologically injured control population.

Receiver-operator characteristic (ROC) curves were constructed to determine the optimal cutoff (as determined by maximal area under the curve) of serum GFAP level at NICU admission to identify HIE qualifying for whole-body cooling and to identify neonates with brain abnormalities on MRI. The area under the ROC curve was used to compare the ability of admission GFAP to identify neonates with abnormalities on brain MRI scans compared with other currently used tests to identify these infants: non-reassuring fetal heart rate tracing, meconium, 5 minute Apgar less than 7, and umbilical arterial pH less than 7.0 or base deficit greater than 12 mM. Statistical analyses were performed with Stata 10 (StataCorp, College Station, Tex.).

Results

Study Population and Clinical Characteristics.

During the period from Apr. 28, 2009, to Jul. 11, 2010, there were 652 admissions to NICU of which 23 consecutive neonates were diagnosed with clinical moderate/severe HIE that qualified for whole-body cooling. These 23 neonates were matched 1:1 by gestational age at birth within 1 week to neonates admitted to the NICU for non-neurological indications. The mean (SD) gestational age for cooled neonates was 38.7 (1.5) weeks and 39 (1.4) weeks for the controls.

Maternal and neonatal characteristics are summarized in FIG. 18. Maternal demographics and incidence of cesarean delivery were not different. The most likely reason for admission for the controls was respiratory distress and to rule out sepsis. The subjects weighed 291 g less at birth, which was statistically, but not clinically, significant and were significantly more likely to have had a placental abruption, metabolic acidosis, a 5 minute Apgar less than 7 and had a longer length of stay in the NICU.

GFAP as a Biomarker of HIE.

Figure 19:
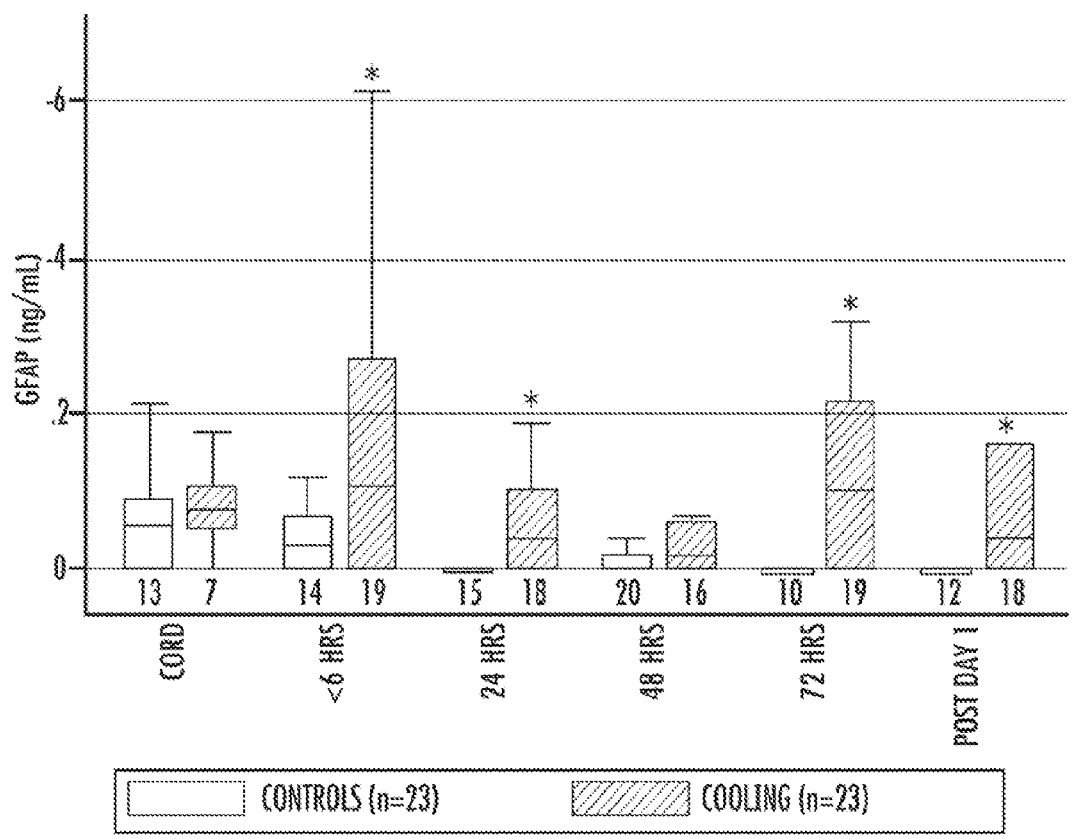
FIG. 19 displays box plots of GFAP levels (ng/ml) for control vs. cooled neonates. The number under each box is the number of samples available for analysis. * indicates P<0.05 compared with controls.

For the controls, a GFAP level at 54 of 138 of the desired time points (39.1%) could not be obtained, and for the cooled subjects 50 of 207 (24.2%) because of an insufficient amount of serum, no blood drawn on that day or an inability to obtain cord blood because the birth occurred at an outside hospital. When neonates with clinical moderate to severe HIE treated with whole-body cooling were compared with controls, mean GFAP levels were significantly elevated in neonatal serum upon admission to the NICU within 6 hours of birth and on days 1, 3, and 4 of life, with P=0.032, P=0.013, P=0.013, and P=0.003, respectively. See FIG. 19.

Persistence of serum GFAP was much greater in the HIE group with 6 of 23 controls (26%) and 17 of 23 HIE neonates (74%) having quantifiable GFAP in the serum from day 1 to 4 of life (P=0.001). GFAP levels on admission to the NICU in the control neonates did not significantly change with gestational age (r=0.22, P=0.22). Combining all the GFAP values from birth through day 4 of life for the controls showed that the median was 0 ng/ml and the 95th percentile was 0.20 ng/ml. None of the controls had a GFAP value above the 95th percentile vs. 10 of 23 cooled neonates (43.4%) (P<0.001). Of the 23 cooling subjects, 4 (17.4%) had abrupt elevations of GFAP the day after the 72 hour cooling regimen was completed. See FIG. 19.

To test GFAP levels upon NICU admission as a screening test for moderate to severe HIE requiring treatment with whole-body cooling, ROC curves were generated for various thresholds of GFAP level. The NICU admission GFAP of 0.08 ng/ml or greater was the optimal cutoff point to distinguish the groups and produced an area under the ROC curve of 0.709.

Correlation of GFAP with MRI Evidence of Brain Injury and Functional Outcome at Discharge.

All 23 neonates that underwent whole body cooling had a clinical brain MRI during their NICU hospitalization. There was no difference in the time after birth that these MRI scans were performed with a mean (SD) of 7.4 (3.7) days of life in the abnormal MRI group and 7.4 (3.9) days in the normal MRI group (P=0.49). Findings suggestive of HIE were seen in 8 of 23 brain MRI scans (35%). Although those with an abnormal brain MRI were significantly more likely to have been delivered after placental abruption, none of the clinical markers of HIE were associated with an abnormal MRI. See FIG. 20.

Figure 21:
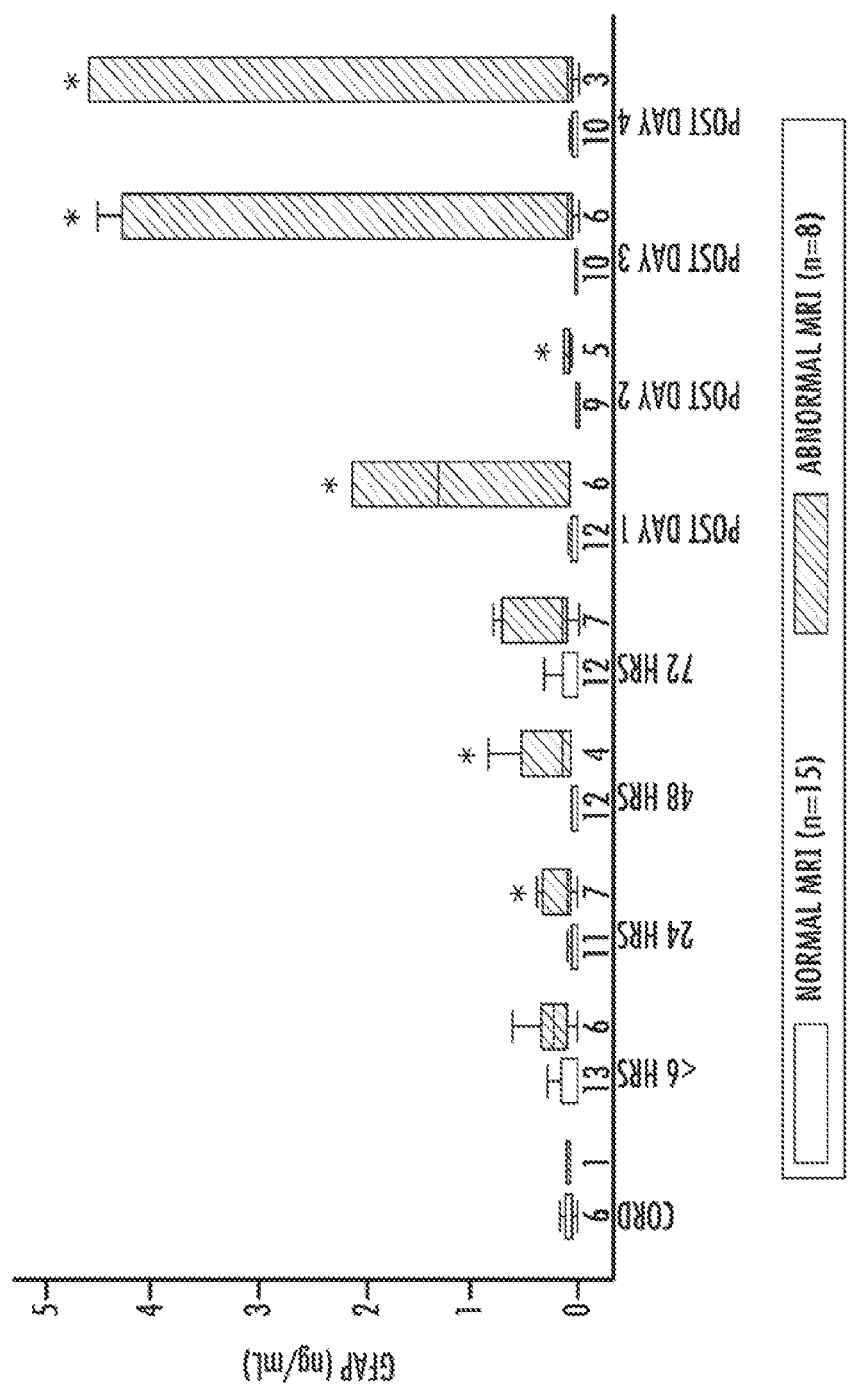
FIG. 21 displays box plots of GFAP levels (ng/ml) for cooled neonates compared by results of brain MRI. The number under each box is the number of samples available for analysis. * indicates P<0.05 compared with neonates with normal MRI.

Serum GFAP levels were consistently elevated in neonates treated with whole body cooling that had abnormal brain MRI scans. See FIG. 21. These comparisons were statistically significant on days 1-2 and 4-7 of life, with P=0.02, P=0.007, P=0.001, P=0.001 and P=0.007, respectively. In 4 of 8 neonates with an abnormal MRI (50%), a significant increase in GFAP levels the day after cooling ended was observed.

Using ROC analysis, a GFAP of 0.15 ng/ml or greater upon NICU admission was the optimal cutoff to identify neonates with abnormal brain MRI scans among all neonates that underwent whole body cooling (area under ROC curve 0.718). This was superior to indicators currently used to identify intrapartum HIE such as non-reassuring fetal heart rate tracing (area under ROC curve 0.613), meconium (0.508), 5 minute Apgar less than 7 (0.500), and umbilical arterial pH less than 7.0 or base deficit greater than 12 mM (0.500).

To relate GFAP levels to functional outcome, time to oral feeding was used. See FIG. 22. For the 15 neonates that underwent whole-body cooling whose MRI was normal, the time to full oral feeds was a mean (SD) of 9.1 (5.4) days. For the 8 neonates with abnormal MRI scans, 1 died at day of life 7, 5 required a gastric tube at a mean (SD) of 114 (81) days of life, and 2 were on full oral feeds at mean (SD) of 17 (9) days of life. Serum GFAP levels on NICU admission were 0.61 ng/ml for the neonate who died, a mean (SD) of 0.26 (0.10) ng/ml for the neonates discharged with gastric feeding assistance (both of which are above the 95th percentile of GFAP level among non-neurologically injured neonates), and a mean (SD) of 0.04 (0.06) ng/ml for the neonates discharged on full oral feeds (P=0.03).

Among all neonates treated with cooling for moderate to severe HIE, serum GFAP level at NICU admission had an area under the ROC curve of 0.731 in predicting an abnormal brain MRI with sensitivity of 50.0%, specificity of 84.6%, positive predictive value of 60.0%, and negative predictive value of 78.6%.

Discussion

The present example describes the first use of a brain-specific protein, GFAP, as a serum biomarker correlating with clinical moderate to severe HIE, development of MRI evidence of brain injury, and functional outcome. Although HIE occurs in 2.5 per 1000 live births at term and 14.5% of all cases of cerebral palsy are associated with intrapartum hypoxia-ischemia, the timing, duration, and outcomes of these injuries are poorly defined. See Graham et al., 199 AM. J. OBSTET. GYNECOL. 587-95 (2008).

Biomarkers serve as surrogates of disease injury, evolution, and outcome. Authors of a systematic review of 110 publications in newborns (longer than 36 weeks) that had HIE strictly defined concluded that without biomarkers, the timing, duration, and effectiveness of therapies are ascertained in a relatively blind fashion. See Ramaswamy et al., 40 PEDIATR. NEUROL. 215-26 (2009); and American College of Obstetricians and Gynecologists, American Academy of Pediatricians. Chapter 8. Criteria required to define an acute intrapartum hypoxic event as sufficient to cause cerebral palsy. In: Neonatal encephalopathy and cerebral palsy.

Washington, D.C.: ACOG; 2003:73-80. They also concluded that prospective studies should focus on determining which biomarkers best identify neonates who will benefit from intervention.

One study assayed cerebrospinal fluid GFAP levels and found them predictive of neonatal death only, not of abnormal outcomes in survivors; however, blood levels of GFAP were not explored. Blennow et al., 90 ACTA. PAEDIATR. 1171-75 (2001). In the present study, using a new sensitive assay for GFAP, GFAP was found to be an early biomarker of HIE. The control group for this study did not include normal neonates but was representative of the general NICU population of non-premature ill neonates; therefore, the conclusions regarding GFAP as a diagnostic biomarker of HIE may be conservative and highlight the specificity of GFAP for neonatal brain injury in the context of potentially confounding failure of other organ systems.

Several postnatal biomarkers in blood, cerebrospinal fluid, and urine have been studied to detect HIE, but most have limitations. The urine lactate/creatinine ratio requires specialized nuclear magnetic resonance technology (Oh et al., 153 J. PEDIATR. 375-8 (2008)), cerebrospinal fluid is not amenable to serial sampling (Ramaswamy et al., 40 PEDIATR. NEUROL. 215-26 (2009); and Blennow et al., 90 ACTA. PAEDIATR. 1171-75 (2001)), and other protein biomarkers (e.g., neuron-specific enolase and S100B) have limitations in tissue specificity. See Ramaswamy et al., 40 PEDIATR. NEUROL. 215-26 (2009).

Mild hypothermia immediately after hypoxic-ischemic brain injury preserves cerebral energy metabolism, reduces cytotoxic edema, and improves histological and functional outcome. Thoresen et al., 5 SEMIN. NEONATOL. 61-73 (2000). A study of term infants with HIE treated with selective head cooling1 or whole-body cooling (Inder et al., 145 J. PEDIATR. 835-7 (2004)) found that both modes were associated with a decrease in basal ganglia and thalamic lesions, which are predictive of abnormal outcome, and a decrease in severe cortical lesions was seen with selective head cooling. See Rutherford et al., 116 PEDIATRICS 1001-6 (2005).

Although cooling in infants with clinical HIE is associated with a reduction in death and neurological impairment (Edwards et al., 340 BMJ c363 (2010)), it is used as a one-size-fits-all therapy because there are no means of monitoring efficacy while it is being delivered. Hypothermia therapy has been shown not to alter serum GFAP levels after severe traumatic brain injury in children. See Fraser et al., 12 PEDIATR. CRIT. CARE MED. 319-24 (2011).

As described above, elevated serum GFAP during cooling is significantly associated with evidence of brain injury by MRI. The ability to monitor the level of GFAP during cooling may allow triage of neonates to an escalation of therapy with cooling plus other therapies such as erythropoietin (Kim et al., 23 J. KOREAN MED. SCI. 484-91 (2008)), antiepileptic drugs (Glass et al., 9 CURR. TREAT. OPTIONS NEUROL. 414-23 (2007)), and xenon. See Hobbs et al., 39 STROKE 1307-13 (2008). Fifty percent of neonates with brain injury on MRI in this study had a marked increase in levels of GFAP after completion of the 72 hour cooling protocol. These were also the only neonates that had daily increasing levels of GFAP during cooling, making this pattern 100% predictive of an abnormal MRI. This increase after cooling could result from continued brain injury that was suppressed by cooling or could be evidence of rewarming injury.

The dramatic increase in GFAP levels seen at the conclusion of the 72 hour cooling period also raises the question as to what is the optimal duration. At this point, there are no surrogate markers of therapeutic success, and there are no benchmarks to compare new treatments as they are developed. It is possible that circulating brain protein biomarkers such as GFAP will fill this gap.

Although the use of imaging has greatly improved diagnostic accuracy in brain injury, these tests are limited in the early hours after hypoxic-ischemic injury and are difficult to perform in critically ill neonates. Consequently, there are settings in which a rapid blood test for brain injury would be invaluable.

MRI is the most common clinical test used for evaluation of neonates with HIE and is associated with outcomes. Barnett et al., 33 NEUROPEDIATRICS 242-8 (2002). The present example demonstrates that levels of GFAP upon NICU admission and during cooling are predictive of an abnormal MRI.

In summary, GFAP may serve as a biomarker to identify and monitor neonates with clinical HIE receiving cooling therapy. Its predictive ability to identify neonates with brain abnormalities because of HIE is better than currently used clinical indicators. Based on the results of this study, GFAP could be used to more specifically and sensitively diagnose brain injury at birth, to facilitate triage of infants into HIE treatment protocols with hypothermia plus adjuvant treatments, serve as an intermediate outcome to benchmark evolving HIE therapies, and give prognostic information to the parents of these at risk children.

Example 12: Proteomic Identification of Thrombospondin-1 and L-Selectin as Plasma Biomarkers of Subclinical Brain Injury in Children with Sickle Cell Disease Biomarkers of brain injury have the ability to transform the care of sickle cell disease, as exemplified by transcranial Doppler. It was hypothesized that an unbiased proteomics screen of plasma from sickle cell disease (SCD) patients would yield biomarkers of subclinical brain injury. After depleting plasma of the 12 most abundant proteins, a mass spectrometry-based screen of plasma obtained as part of the Silent Infarct Transfusion (SIT) Trial yielded thrombospondin-1 (TSP-1) and soluble L-selectin (SELL). Using a commercial ELISA, TSP-1 and SELL were not different between normal age matched controls (n=23) and SCD patients (n=123). However SCD subjects 5-14 years-old screened for the SIT Trial, a random sampling of SCI (n=62) and non-SCI (n=51) patients demonstrated that TSP-1 and SELL were significantly increased (p=0.013 and p=0.021 respectively). These data validate the experimental approach to biomarker discovery of brain injury in sickle cell disease and describe the first circulating biomarkers of SCI.

Introduction

Sickle cell disease (SCD) is a chronic hemolytic anemia that is characterized by injury to multiple organs. Stroke is the most prominent injury that can occur to the brain in SCD. Stroke risk has been reduced significantly in children by identifying those patients with elevated transcranial Doppler velocities and implementing chronic red cell transfusion. See King et al., 50 PEDIATR. BLOOD CANCER 599-602 (2008); and Adams et al., 339 N. ENGL. J. MED. 5-11 (1998). It is currently under study whether risk for brain injury, as ascertained by presence of silent cerebral infarct (SCI) on MRI, can be mitigated by chronic red blood cell transfusion. King et al., 50 PEDIATR. BLOOD CANCER 599-602 (2008). Clearly, biomarkers of stroke risk have transformed care in sickle cell disease.

In children, SCI is an independent risk factor for lower IQ, poorer school performance, and overt stroke. See Miller et al., 139 J. PEDIATR. 385-90 (2001); AND MERNAUDIN ET AL., 15 J. CHILD NEUROL. 333-43 (2000). MRI is the only method to identify those patients with SCI. MRI is not an ideal technique to track disease risk because it is expensive, it has limitations on how frequently it can be used, and for some pediatric patients it requires anesthesia, which carries increased risk in SCD, including death. A blood biomarker of SCI would fill a clinical void because blood is easy to obtain and measure, a biomarker may determine risk of or progression of neurologic injury to overt stroke, and a biomarker could benchmark current and new therapies for SCI.

Using a non-biased mass spectrometry based proteomics approach, trombospondin-1 (TSP-1) and soluble L-selectin (SELL) were identified in the plasma of SCD patients with SCI who were screened by MRI and proteomic analysis. Both TSP-1 and SELL have been studied in SCD with the roles poorly defined, and in acute brain injury with evidence as important factors for brain recovery (TSP-1) (Lin et al., 34(1) STROKE 177-86 (2003)) or as predictive biomarker (SELL) (Lo et al., 26(9) J. NEUROTRAMA 1479-87 (2009). Given the identification of TSP-1 and SELL in the proteomics screen and the available literature, it is hypothesized that TSP-1 and SELL concentrations could serve as a biomarker of brain injury in sickle cell disease.

Methods

Patients.

A cross-sectional sample of children 5-14 years old with sickle cell disease (HbSS and HbS$\beta^0$) who were screened for the Silent Infarct Transfusion Trial (SIT Trial, ClinicalTrials.gov NCT00072761) were studied (n=259). The SIT Trial is a multi-center, randomized, controlled trial of a three year-transfusion program in children with sickle cell disease and SCI. The primary endpoint includes the occurrence of overt stroke or new or progressive SCI. All patients signed informed consent. SCI is defined by a normal neurologic exam and MRI signal abnormality visible on two views on T2 weighted images. The signal abnormality must measure at least 3 mm in one dimension. SCI status is adjudicated by a panel of neuroradiologists and neurologists. Positive and negative control patients were selected from Johns Hopkins Hospital clinics and inpatient units. Positive control plasma samples were obtained from hospitalized children and adults admitted for overt stroke or brain surgery. Negative controls were selected from children 5-16 years old from the Harriet Lane Pediatrics Clinic at Johns Hopkins Hospital. Clinic notes were reviewed to exclude patients with any acute illness, neurologic disorder, or chronic illness other than asthma, obesity, and behavior/mood disorders. De-identified blood samples and clinical data on these controls were obtained through an IRB approved study.

Plasma Preparation and Mass Spectroscopic Analysis.

Blood was collected into ACD or EDTA tubes and spun at 1500 g for 8 minutes per the SIT Trial protocol and stored at −70° C. in the Biologic Repository for the SIT Trial at Johns Hopkins University until analysis. Five hundred microliters of plasma from 15 patients (discovery cohort, n=7 non-SCI and 8 SCI) was depleted of 12 abundant plasma proteins using an LC10 IgY column (Beckman Coulter, Fullerton, Calif.) on a ProteomeLab Protein Partitioning System (PPS, Beckman). IgY column flow through was separated into 39 fractions by reverse phase HPLC over a C18 column (Jupiter, Phenomenex) using a continuous acetonitrile gradient (PPS, Beckman). Fractions were dried (SpeedVac, Thermo Scientific, Waltham, Mass.) and trypsin digested (Promega, Madison, Wis.) at 37° C. overnight. Spectra on each sample were obtained by LC/MS/MS (LTQ-Orbitrap, Thermo Scientific). Spectra were searched for protein identifications using Xtandem! and a human IPI database version 3.4. Post search analysis was performed using PASS (Integrated Analysis Inc., Bethesda, Md.) with a confidence level of <0.9 as a protein identification cut off.

TSP-1 and SELL Quantitative Measurements.

TSP-1 and SELL were measured in diluted duplicate plasma samples using a sandwich ELISA (R&D Systems) according to the manufacturer's protocol. SCI and non-SCI patient samples were picked randomly.

Statistics.

Student's t test was used to compare plasma concentrations between groups.

Results

Mass Spec Identification of TSP-1 and SELL in SCD Plasma.

Figure 23:
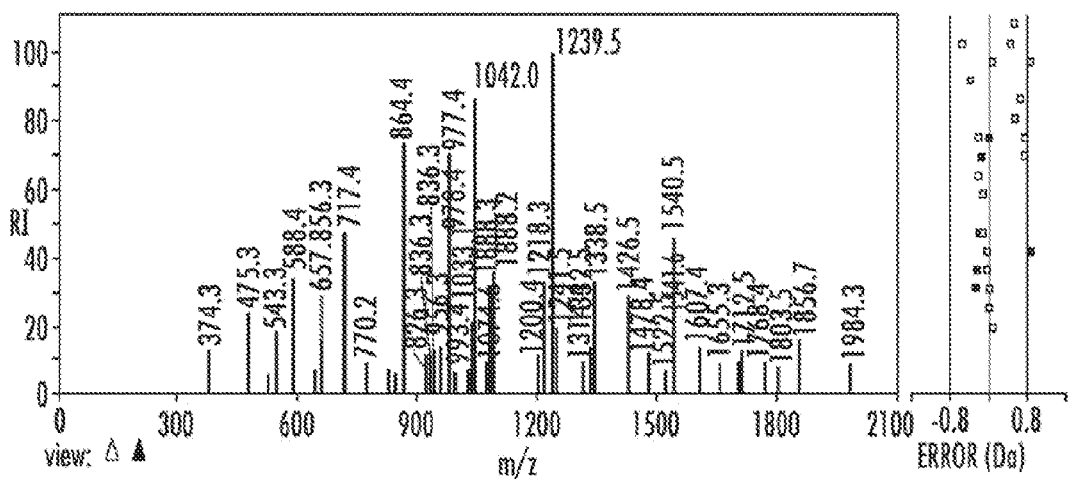
FIG. 23 shows the spectra ion table for one of 16 unique TSP-1 peptides identified. The Log(e) probability was $10^{-8.6}$. This peptide was found in 10 of 15 SITT patients.
Figure 24:
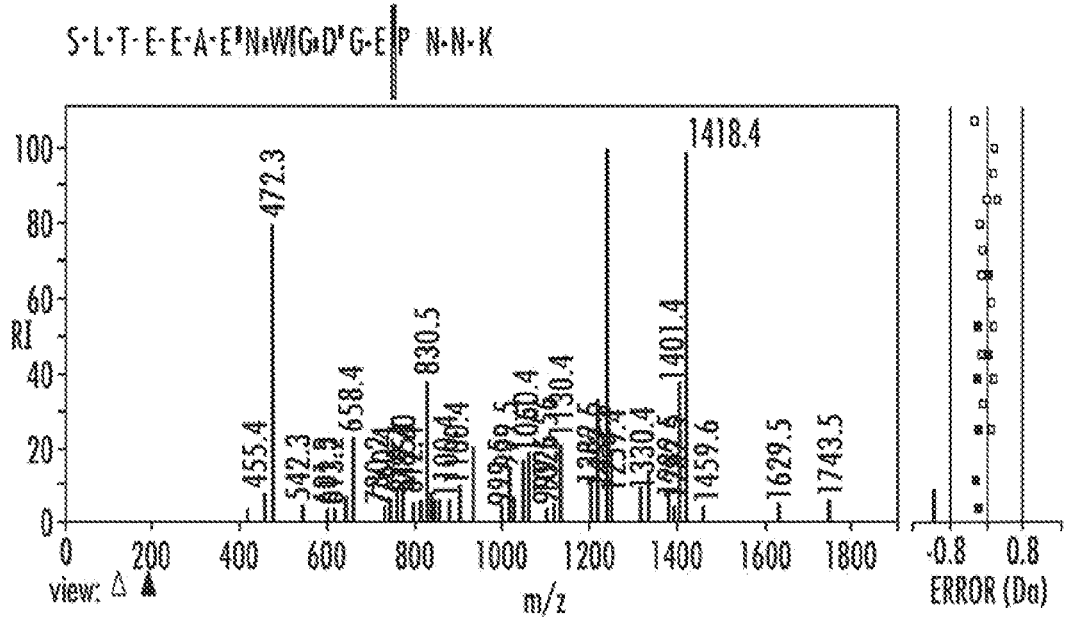
FIG. 24 shows the spectra ion table for one of 3 unique SELL peptides identified. The Log(e) probability was $10^{-4.3}$. This peptide was found in 13 of 15 SITT patients.

As TSP-1 and SELL function as leukocyte adhesion molecules whose role is poorly understood in SCD (Ugochukwu et al., 30(4) INT. J. LAB. HEMATOL. 312-16 (2008); and Brittain et al., 97(7) BLOOD 2159-64 (2001)), but circulating SELL has been shown to be a sensitive and specific biomarker of pediatric brain trauma. Using Xtandem! to search the discovery cohort (n=15 patients) spectra, 14 unique peptides for TSP-1 and 3 peptides for SELL in 10 and 13 patients respectively. Xtandem! Log(e) scores ranged from −1.1 to −10.1. Representative spectra for a peptide each for TSP-1 (FIG. 23) and for SELL (FIG. 24) are shown.

Plasma TSP-1 and SCI.

Figure 25:
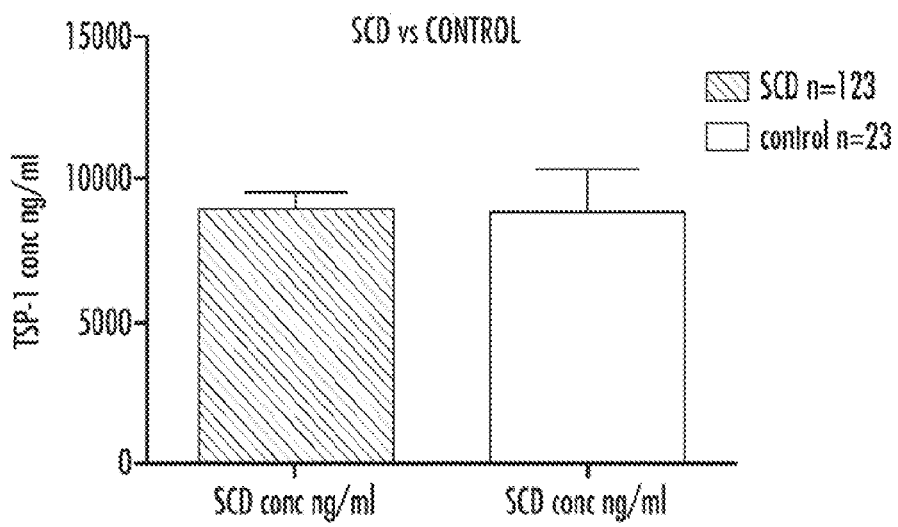
FIG. 25 presents TSP-1 concentrations in age-matched (5-14 year old) normal and SCD children.
Figure 26:
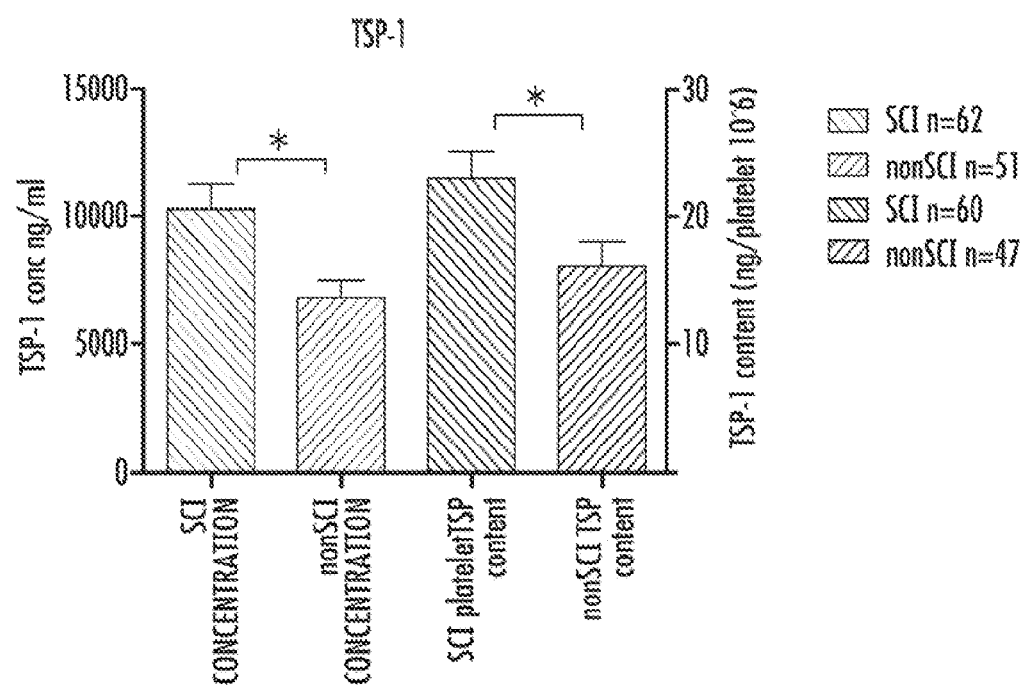
FIG. 26 shows plasma TSP-1 concentrations in steady-state sickle cell disease (5-14 years old). TSP-1 content is TSP-1 concentration/$1 \times 10^6$ platelets. *=P<0.013 or 0.039 SCI vs. non-SCI.

Several studies have demonstrated that TSP-1 in situ in the brain is important for recovery of brain injury and that TSP-1 can also play a role increasing the adherence of SCD red cells to endothelial cells. As shown in Table 6 and FIG. 25, TSP-1 levels when compared between normal age matched children and with SCD have no significant difference in concentration (p=0.49). However, as shown in Table 7 and FIG. 26, there was a statistically significant increase in TSP-1 concentrations between SCI positive and SCI negative patients (p=0.013).

TABLE 6

TSP-1 Levels Control vs. SCD

| | SCD, n = 123 | Control, n = 23 | P |
|---|---|---|---|
| Mean TSP-1 ng/ml (range) | 8928 (724-36500) | 6926 (889-26120) | 0.49 |

TABLE 7

TSP-1 Concentrations in SCI and Non-SCI Children

| | SCI, n = 62 | Non-SCI, n = 51 | P |
|---|---|---|---|
| Mean TSP-1 ng/ml (range) | 10370 (845-36500) | 6926 (724-20770) | .013 |
| Mean TSp content ng/million plts (range) | 22.95 (3-66) | 16.23 (1-56) | .039 |
| Mean plt count | 483,000 | 432,600 | .463 |

Plasma SELL in SCI.

SELL is a leukocyte adhesion molecule whose role is poorly understood in SCD, but circulating SELL has been shown to be a sensitive and specific biomarker of pediatric brain trauma. Lo et al., 26(9) J. NEUROTRAUMA 1479-87 (2009). Because SELL was observed in 13/15 of the SITT discovery cohort, SELL was validated as being present in SCD plasma and significance for SCI. SELL mean levels are not significantly different between race and age matched controls and SCD patients. However when SCI and non-SCI groups were compared (FIG. 27), SELL mean levels were significantly elevated in the SCI group (p=0.021).

Discussion

Using an unbiased screen of the plasma proteome in sickle cell disease, two circulating proteins, TSP-1 and SELL, were identified as significantly associated with SCI in children with SCD. The discovery of such specific proteins from the plasma in sickle cell patients validates the experimental approach to biomarker discovery used in the present example.

The present inventors have demonstrated that TSP-1 and SELL are biomarkers of silent cerebral infarction in sickle cell disease, as diagnosed by MRI in a cross sectional study of SIT Trial participants, where the timing of SCI is not known. In a cross-sectional population of children 5-14 years old with steady-state sickle cell disease, 30% of SCI and 4% of non-SCI had extreme elevations of TSP-1. TSP-1 is a marker known to play a significant role in brain injury repair and angiogenesis. These children with markedly elevated TSP-1 levels have subclinical brain injury by definition as by history and neurologic exam, there were no apparent deficits.

SCI is a morbidity defined by either MRI or autopsy. See Moser et al., 17 AM. J. NEURORADIOL. 965-72 (1996); and Rothman et al., 20 ANN. NEUROL. 684-90 (1986). SCI in sickle cell disease has been associated with poorer neurocognitive performance than sickle cell disease patients without SCI (Schatz et al., 56 NEUROLOGY 1109-11 (2001); Armstrong et al., 97 PEDIATRICS 864-70 (1996)), but many children with sickle cell disease have poor neurocognitive function, despite normal brain MRIs. Detection of brain injury by plasma levels of proteins highly specific for brain may be a more sensitive means for detecting injury.

In summary, the results of the present example validate the non-biased strategy for identifying potential biomarkers of brain injury in patients with sickle cell disease by identifying TSP-1, a known marker of CNS injury repair in other populations. The identification of TSP-1 in the plasma of a significant proportion of patients with sickle cell disease and SCI implicate TSP-1 as a biomarker potentially of SCI risk and/or is involved in SCI repair or part of the injury pathway. Further proteomic studies of brain-specific proteins in SCD promise to be of great interest to our understanding, detection and treatment of CNS injury in SCD.

Example 13: Development of Neurogranin Assay the Identification of Human NRGN Specific Aptamers Systematic Evolution of Ligands by EXponential enrichment (SELEX) procedure was used to identify the Human NRGN specific aptamers. Briefly, the specific aptamer was selected from a pool of single strand RNA by filter immobilization. The RNA-NRGN target complex can bind to nitrocellulose filter, and free RNA went through filtration. The specific aptamer was recovered from the filter and PCR amplified. After several round of selection, the specific aptamer with highest affinity with NRGN was enriched and sequencing identified.

Prepare the Library for Selection.

Single strand DNA oligo pool was chemically synthesized. The DNA oligo has 40mer random central core, which flanked by 2 constant sequences, and the library can be amplified by a pair of primers which target the 5' and 3' conserve ends of the library. The sequence of the library is:

5'-TCT CGG ATC CTC AGC GAG TCG TCT G (N40) C CGC ATC GTC CTC CCT A-3' (SEQ ID NO:1)

Generating RNA Library.

The single strand DNA library first was annealed with Sel2 5' primer, the sequence is 5'-GGG GGA ATT CTA ATA CGA CTC ACT ATA GGG AGG ACG ATG CGG-3' (SEQ ID NO:2), which contains a T7 promoter for in vitro transcription. The gap was filled in by Klenow reaction, which was performed at 37° C. for 1.5 hours. The reaction was purified by phenol: chloroform:isoamyl (25:24:1) and chloroform:isoamyl (24:1) extraction once each and further concentrated with Centricon 30 at 4° C. TE buffer, pH7.4 was used to wash the reaction twice while concentration process. The final OD260 was measured and concentration was determined.

The above annealed oligo pool was used to generate RNA library for SELEX by in vitro transcription, using the DuraScribe® T7 Transcription Kits (Epicentre, DS010910), following the manufacture's reaction condition. 2'-Fluorine-CTP (2'-F-dCTP) and 2'-Fluorine-UTP (2'-F-dUTP) were used to replace CTP and UTP in the transcription reaction, the final DuraScript® RNA (2'-fluorine-modified RNA) is completely resistant to RNase A. After in vitro transcription, DNase I was used to treat the reaction and the RNA was extracted with phenol: chloroform:isoamyl (25:24:1) and chloroform once each, followed by concentrate and desalt with Centricon 30 at 4° C.

The RNA was further purified by denatured PAGE (12%, 7M Urea) gel purification. The RNA band was cut from the PAGE gel, RNA was eluted in 2 ml TE buffer overnight at 4° C. The pure RNA was concentrate again using Centricon 30, and concentration of RNA was determined using conventional method.

Nitrocellulose Filter Pre-Clear.

A 13 mm Swin-Lok Filter holder (Whatman) (13-mm diameter), 0.45 um pore size HAWP nitrocellulose disk filters (Millipore) was assembled. The filter was pre-wet with 1 ml washing buffer, which contains 20 mM Hepes pH7.4, 50 mM NaCl and 2 mM $CaCl_2$. 500 pmol RNA was diluted in 100 ul 1× binding buffer (the formula is the same as washing buffer except 0.1% BSA was added), and applied into the reservoir of the filter holder. The filter holder was sealed into a 50 ml conical tube and incubated at 37° C. for 30 minutes. After incubation, the RNA was recovered by pass through the filter unite using 1 ml syringe, and 100 μA of 1× binding buffer was used to wash once. The RNA passed through the filter was collected; total pre-cleared RNA was about 180 μl.

Binding Reaction.

The binding reaction was assembled by adding 50 pmol human NRGN protein into the pre-cleared RNA, the molecular ratio of RNA:protein was about 10:1. The total volume was brought to 200 μl in 1× binding buffer. The reaction was incubated at 37° C. for 15 minutes. A new filter holder was assembled and prewet as above, the binding reaction to the filter was applied, a 5 ml syringe was used to push the binding sample through, and the filter was washed with 5 ml wash buffer.

Recover the Selected RNA.

The filter holder was disassembled, and the filter was transferred into a 1.5 ml centrifuge tube which contained 600 ul phenol: chloroform:isoamyl (25:24:1). The tube was vortexed vigorously for approximately 1 min, then incubated at RT for 30 minutes. Two hundred microliters of H₂O was added and vortexed again, then spun at 14,000 rpm for 10 minutes. The supernatant, which contained the recovered RNA, was extracted with 400 ul chloroform once, then precipitated by adding 500 µl ethanol, 20 µl 3M NaAcetate (pH 5.2) and 3 µl Glycogen blue (Ambion, 5 mg/ml), and then incubated at −80° C. overnight. The RNA was recovered by centrifugation at 14000 rpm for 20 minutes at 4° C., then washed with 1 ml 75% ethanol once, followed by centrifugation and air drying of the RNA. The dried RNA pellet was dissolved into 20 µl H₂O.

Amplify the Selected RNA by RT-PCR.

Five microliters of recovered RNA was used to synthesize the first strand of DNA. Two micromolar of primer Sel2 3' was added into the reaction. The sequence of Sel2 3' primer is: 5'-TCT CGG ATC CTC AGC GAG TCG TC-3' (SEQ ID NO:3). Reverse Transcriptase from Roche (Cat #: 10 109 118 001) was used in the reaction, the conditions were as recommended by the manufacture.

The PCR reaction was assembled as follows: 5 µl first stand DNA (from above step), 3 µl of each 10 µM primers (Sel2 3' from above step and Sel2 5' from above step), 39 µl H2O and 50 µl 2× TopTaq Master Mix (Qiagen). A total of 8 reactions (800 ul) were performed. The PCR cycle condition was as follow: 94° C./5'-->(94° C./30"-->55° C./30"-->72° C./30")×20 cycles-->4° C. The PCR product was confirmed by 3% agarose gel electrophoresis, and the rest of PCR product were desalted and concentrated using a Centricon 30 at 4° C. The concentration of PCR product was determined by measuring OD/260 nm.

Repeat the Selection.

One microgram of concentrated PCR product was used to generate RNA for the next round selection, the protocols for in vitro transcription were followed as described above. A total of 10 rounds of selection was performed.

After 10 rounds of selection, another 3 rounds of selection were performed using high-salt binding buffer to increase the selection stringency. The formula for 1× binding buffer F and washing buffer F is the same as the buffers described above, except that the concentration of NaCl was increased to 150 mM. The other detailed procedure is the same as that described above.

The final PCR product after 13 rounds of selection was cloned into pGEM-T Easy vector (Promega), the enriched aptamers were identified by DNA sequencing. The clones containing the full primers and 40mer insert were aligned using ClustalW2 at EMBL-EBI website.

The Identified Human NRGN Specific Aptamers.

Six clones were chosen for sequencing and all the sequences' quality were very high. After the DNA alignment analysis, 5 out of the 6 clones were almost identical, except that NRGN-A4 had one nucleotide difference (underlined). The less similar one, NRGN-A6, comparing with the other well aligned 5 clones, showed that all of them have 2 T-rich motifs, which are separated by CC/CA (boxed). NRGN-A1 and NRGN-A6 were selected as targets for validation. The following showed the alignment of the aptamers:

```
NRGN-A1  TCTAACGCCTCCCGTATGTTTTCCT---TTTT-CCATTG---CGGAT  40  (SEQ ID NO: 4)

NRGN-A2  TCTAACGCCTCCCGTATGTTTTCCT---TTTT-CCATTG---CGGAT  40  (SEQ ID NO: 4)

NRGN-A3  TCTAACGCCTCCCGTATGTTTTCCT---TTTT-CCATTG---CGGAT  40  (SEQ ID NO: 4)

NRGN-A5  TCTAACGCCTCCCGTATGTTTTCCT---TTTT-CCATTG---CGGAT  40  (SEQ ID NO: 4)

NRGN-A4  TCTAACGCCTCCCGCATGTTTTCCT---TTTT-CCATTG---CGGAT  40  (SEQ ID NO: 5)

NRGN-A6  -TTTTCATTTTC---ATTTTTTTCCAAATCGATCCGCCGGACCTTAT  43  (SEQ ID NO: 6)
```

Validation of the Aptamer-NRGN Interaction.

NRGN-A1 and NRGN-A6 RNA were chemically synthesized based on the sequences identified; adding a biotin linker to the RNA 3' end. Two different strategies were used to test NRGN aptamer and NRGN recombinant protein interaction. The details are as described below.

Using Dot Blot to Detect the RNA Protein Complex on Nitrocellulose.

Based on the same mechanism that was used in SELEX procedure, RNA-protein complex can be retained on nitrocellulose membrane, a dot blot was used to detect the biotin labeled RNA aptamer. First, a 2-fold series dilution of His-NRGN recombinant protein was made, the amount of protein range from 10 pmol to 0; and then each sample was mixed with 1 pmol of NRGN aptamer RNA. The volume of final binding reaction was kept at 20 µl in 1× binding buffer F, the reactions were incubated at 37° C. for 15 min.

Meanwhile, the dot blot apparatus (Bio-Rad, #170-6545) was setup. The nitrocellulose membrane was cut and shaken in 1× washing buffer F for 30 min prior to use. The nitrocellulose membrane was put on top of pre-wet Whatman paper and placed on the bottom of the apparatus, then the vacuum was assembled and hooked up. The membrane was washed with 100 ul 1× washing buffer F per well once, then the binding reaction was applied. After the reactions were passed through, the membrane was washed with 200 ul 1× washing buffer F once, and then drained by vacuuming. The membrane was then UV-crosslinked (Bio-Rad, #165-5031).

The Chemiluminescent Nucleic Acid Detection Module (Pierce, #89880) was used to detect the Biotin labeled RNA aptamer retained on nitrocellulose, following the manufacturer's instruction. Briefly, the membrane was incubated with streptavidin-HRP conjugate, and detected with the chemiluminescent substrate of HRP.

Figure 28:
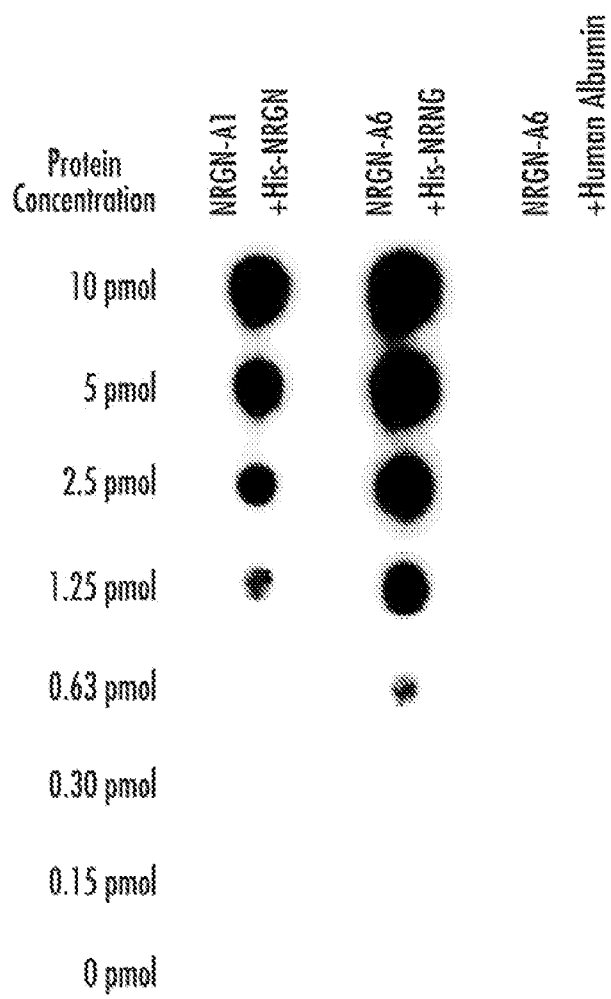
FIG. 28 is a gel showing the minimum amount of neurogranin aptamers needed to for detection of neurogranin protein.

As a result, both NRGN aptamers NRGN-A1 and A6 bound to NRGN protein, the minimum amount of protein needed for detection using this method was 1.25 pmol and 0.63 pmol respectfully. When the same molar of human albumin was used as control, no signal could be detected, despite the amount of albumin used. This result indicated that both of these 2 aptamers bind to His-NRGN protein specifically. See FIG. 28.

Pull-Down Assay.

Biotin labeled aptamers were immobilized on streptavidin particles and a pull-down assay was performed. Aptamers were diluted to 1 pmol/μl in TEN100 buffer (10 mM Tris-HCl, pH7.5, 1 mM EDTA, 100 mM NaCl), heated at 65° C. for 5', then left at RT for 20 minutes to let the RNA fold into its natural conformation. Streptavidin magnetic particles (Roche, 11641778001) were washed 3 times with twice volume of TEN100 buffer, then the aptamer samples were added and incubated at RT for 30 minute with rotation.

After incubation, the particles were washed with TEN100 buffer 3 times, and then equilibrated with 1× binding buffer F once. Different amounts of NRGN protein (0-2 nmol) were diluted in 1× binding buffer and added into the aptamer immobilized magnetic particles, then incubated at 37° C. for 15 minutes.

Figure 29:
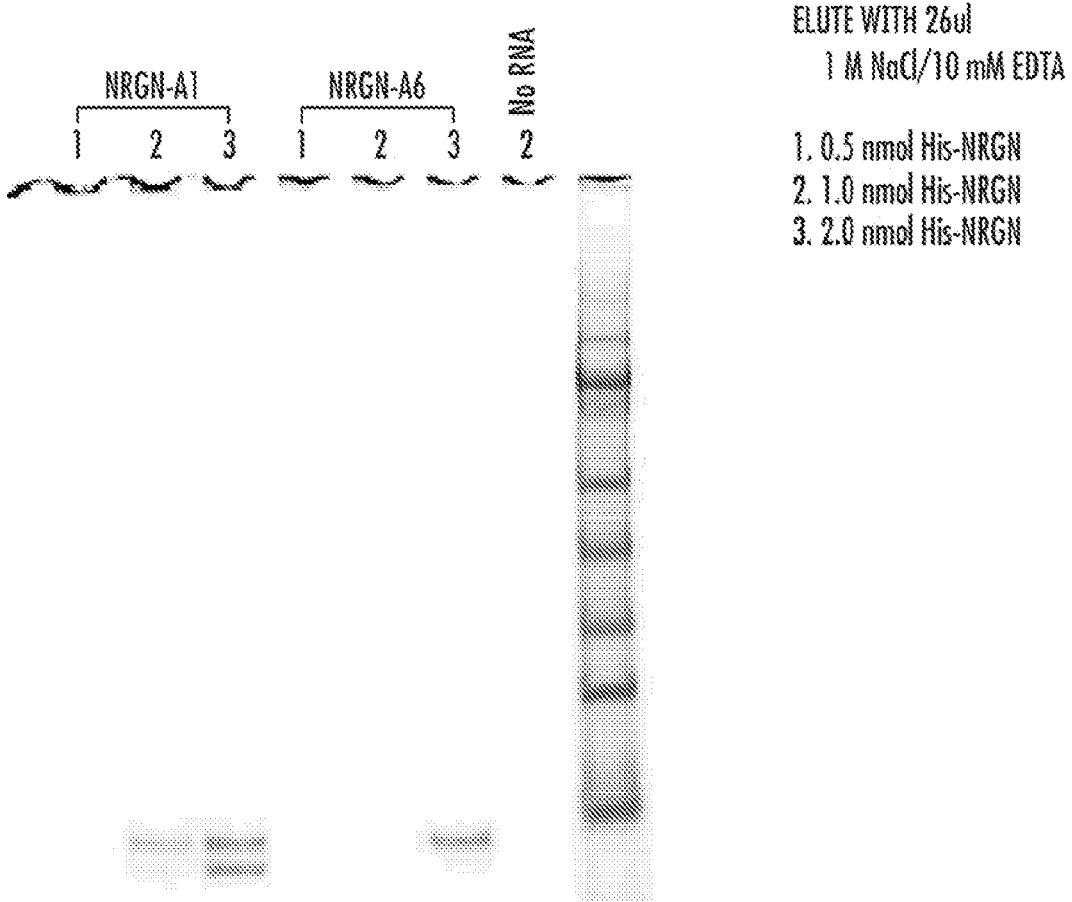
FIG. 29 shows the results of a pull-down assay using the neurogranin aptamers.

After binding incubation, the particles were washed twice with TEN100 buffer. The aptamers protein complex was dissociated by incubating in 26 μl elution buffer (1M NaCl, 10 mM EDTA) at room temperature for 10 min. The eluted protein was subjected to SDS-PAGE, and the protein bands were visualized by coomassie staining. The human albumin protein was used as negative control. A typical stained gel is shown in FIG. 29.

Both of the dot blot and pull-down assays showed that the aptamers specifically bind to human NRGN recombinant protein.

Development of a Neurogranin Multiple Reaction Monitoring (MRM) Assay.

A neurogranin signature peptide was developed for a mass spectroscopy quantitative MRM assay. The peptide sequence and transitions are shown in the table below. Labeled GPGPGGPGGAGVAR (SEQ ID NO:7) was spiked in the samples to make standard curve to measure the concentration of signature peptide GPGPGGPGGAGVAR (SEQ ID NO:7). Peptide KGPGPGGPGGAGVAR (SEQ ID NO:8) is also monitored to make sure there is no miscleavage in tryptic digestion.

TABLE 8

Neurogranin Peptide Sequences

| Precursor Q1 | Transitions Q3 | Peptide ID |
|---|---|---|
| 553.79 | 366.18 | GPGPGGPGGAGVAR (SEQ ID NO: 7) |
| 553.79 | 423.2 | GPGPGGPGGAGVAR (SEQ ID NO: 7) |
| 553.79 | 684.38 | GPGPGGPGGAGVAR (SEQ ID NO: 7) |
| 553.79 | 741.4 | GPGPGGPGGAGVAR (SEQ ID NO: 7) |
| 553.79 | 798.42 | GPGPGGPGGAGVAR (SEQ ID NO: 7) |
| 553.79 | 895.47 | GPGPGGPGGAGVAR (SEQ ID NO: 7) |
| 553.79 | 952.49 | GPGPGGPGGAGVAR (SEQ ID NO: 7) |
| 558.792 | 366.18 | Labeled GPGPGGPGGAGVAR (SEQ ID NO: 7) |
| 558.792 | 423.2 | Labeled GPGPGGPGGAGVAR (SEQ ID NO: 7) |
| 558.792 | 694.39 | Labeled GPGPGGPGGAGVAR (SEQ ID NO: 7) |
| 558.792 | 751.41 | Labeled GPGPGGPGGAGVAR (SEQ ID NO: 7) |
| 558.792 | 808.43 | Labeled GPGPGGPGGAGVAR (SEQ ID NO: 7) |
| 558.792 | 905.48 | Labeled GPGPGGPGGAGVAR (SEQ ID NO: 7) |
| 617.846 | 684.38 | KGPGPGGPGGAGVAR (SEQ ID NO: 8) |
| 617.846 | 741.4 | KGPGPGGPGGAGVAR (SEQ ID NO: 8) |
| 617.846 | 798.42 | KGPGPGGPGGAGVAR (SEQ ID NO: 8) |
| 617.846 | 950.5 | KGPGPGGPGGAGVAR (SEQ ID NO: 8) |
| 617.846 | 962.5 | KGPGPGGPGGAGVAR (SEQ ID NO: 8) |

Figure 30:
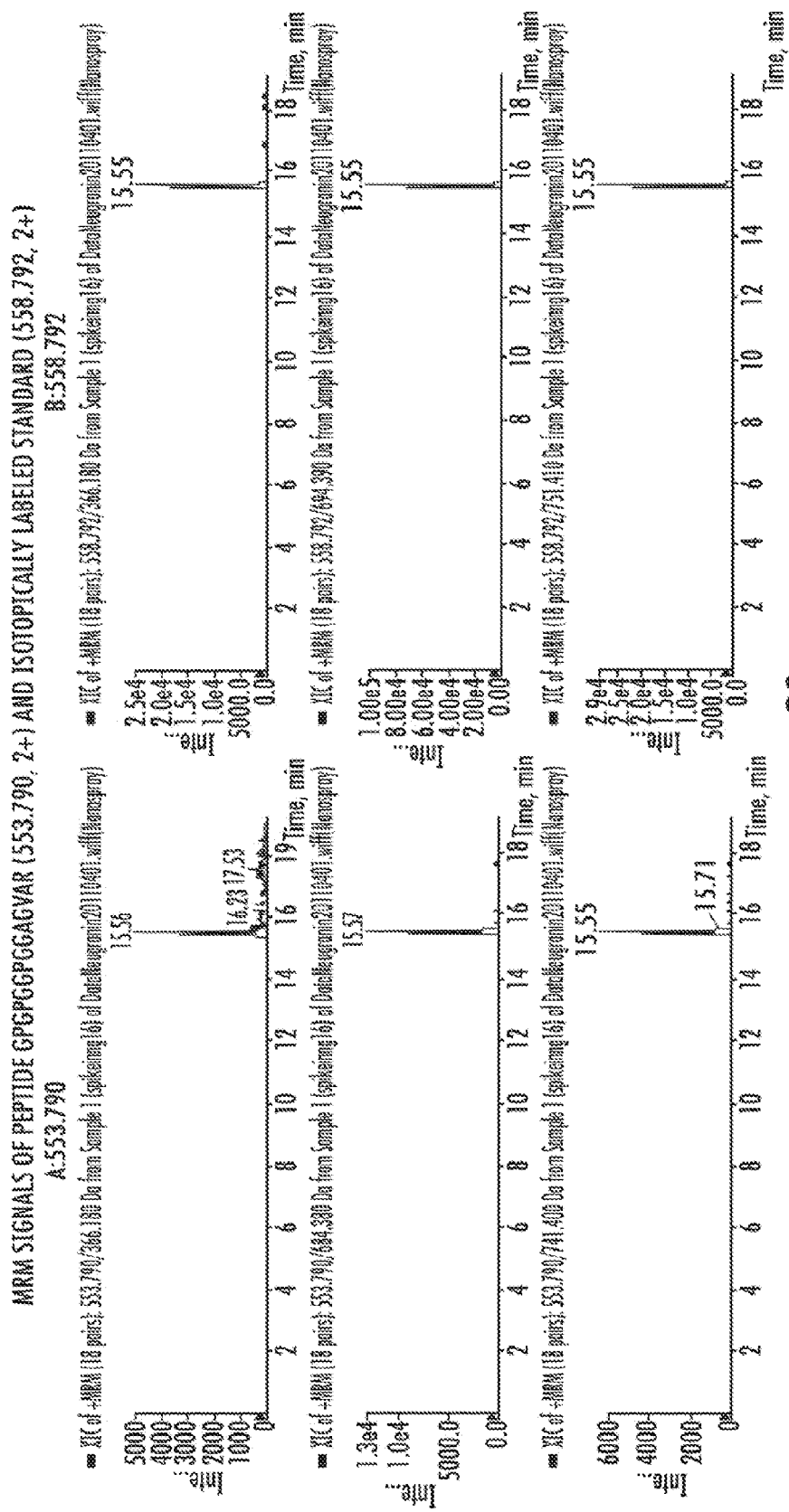
FIG. 30 displays the signals of neurogranin signature peptide and labeled standard peptide using an ABI Sciex Qtrap 4000 triple quadrapole mass spectrometer.

The signals of neurogranin signature peptide and labeled standard peptide using a ABI Sciex Qtrap 4000 triple quadrapole mass spectrometer are shown in FIG. 30.

His-NRGN Recombinant Protein Production.

Figure 31:
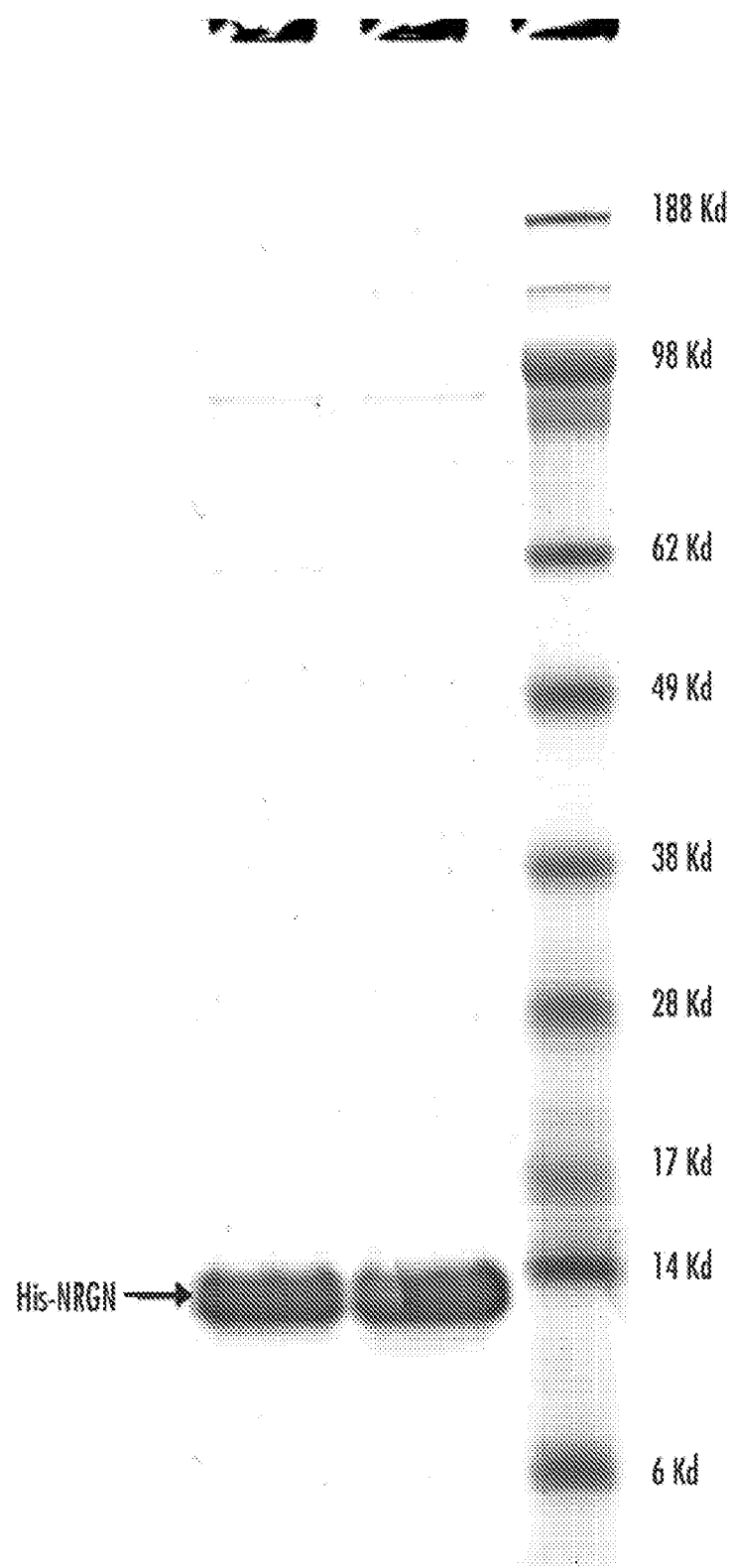
FIG. 31 shows His-NRGN on PAGE gel after coomassie staining. The predicted molecular weight of His-NRGN is 8.5 Kd.

Human NRGN cDNA clone was purchased from Origene (Cat #: RC201209). The coding sequence was cloned into destination vector (Origene, pEX-N-His, Cat # PS 100030) by restriction enzymes (Sgf I+Mlu I) fragment swapping to generate pEX-N-His-NRGN expression plasmid. The coding sequence and reading frame were confirmed by DNA sequencing.

pEX-N-His-NRGN plasmid was transformed into Rosetta 2 (DE3) competent cells (Novagen #71397) according to manufacturer's instruction. The bacteria were cultured in the Overnight Express Instant TB Medium (Novagen #71491) at 37° C. for 16-18 hours, then harvested and suspended in TEN buffer (50 mM Tris, pH8.0, 0.5 mM EDTA and 0.5 M NaCl). The bacteria were lysated by adding 1% NP-40, 25 mg lysozyme and complete proteinase inhibitors (Roche), sitting on ice for 30 minutes, then freeze-thaw one time. The lysate was cleared by centrifugation, then Ni-NTA agarose beads (Qiagen) were added into the supernatant, and rotated at 4° C. for 1 hour. The beads were washed 3 times with washing buffer (20 mM Imidazole, 20 mM KCl and 0.5 M NaCl). The recombinant protein was eluted off the beads by rotating the beads in the elution buffer (100 mM Imidazole, 20 mM $K_3PO_4$ and 167 mM NaCl) at 4° C. for 10 minutes. The eluted protein was dialyzed against 3 L PBS overnight, the protein concentration was determined by conventional protein assay. FIG. 31 shows the typical His-NRGN on PAGE gel after coomassie staining; the predicted molecular weight of His-NRGN is 8.5 Kd.

Development of a Neurogranin Monoclonal.

Figure 32:
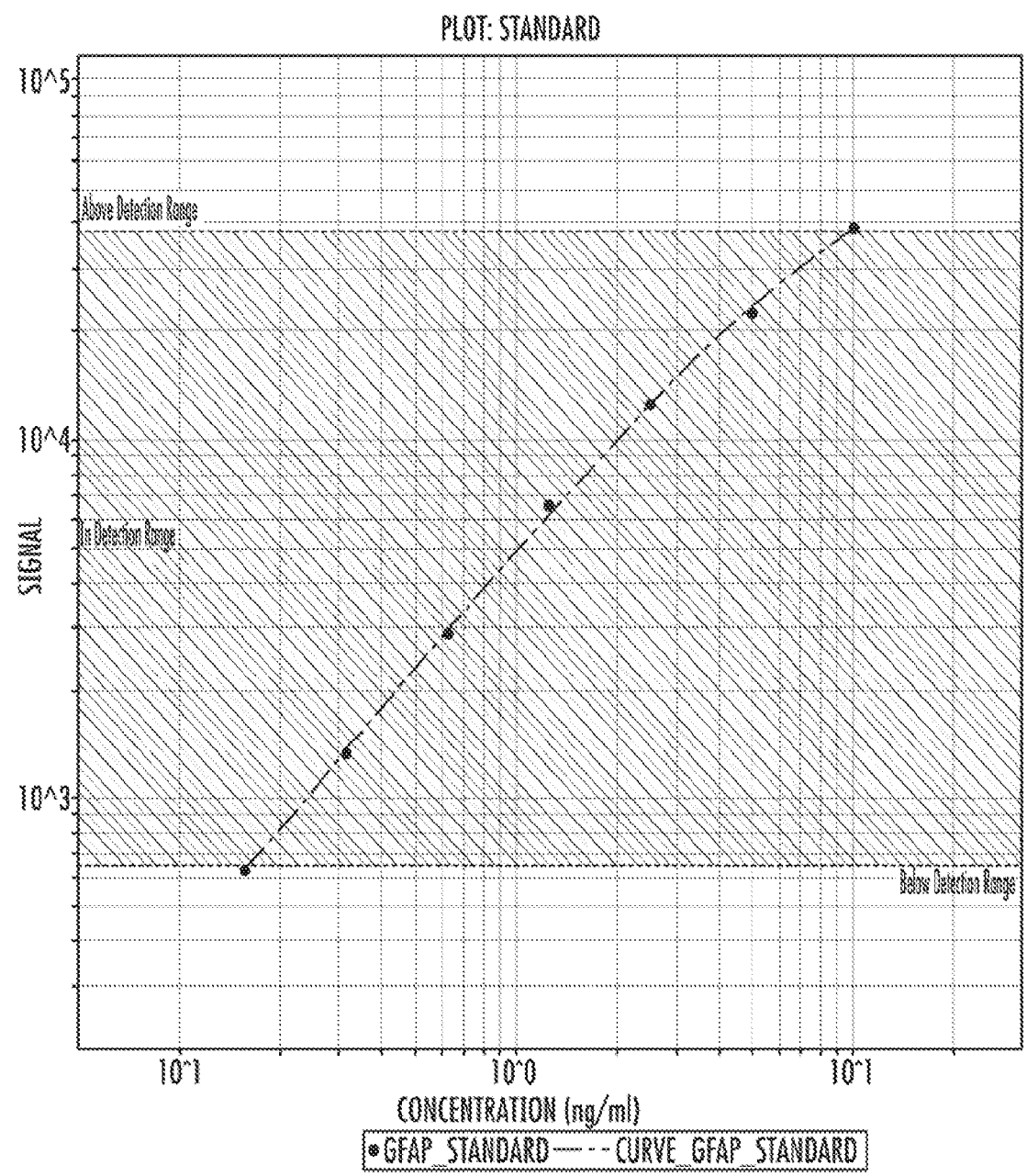
FIG. 32 shows the standard curve of the direct ELISA for recombinant NRGN using mouse monoclonal antibody 30.5.2. The concentration range is 0.002-10 ng/ml.

Recombinant neurogranin described above was used to immunize mice for monoclonal antibody production at Johns Hopkins Thirty clones were screened and clone 30.5.2 was identified that bound neurogranin at high dilution in a direct ELISA shown in FIG. 32.

Development of a Sandwich ELISA for Neurogranin.

Figure 33:
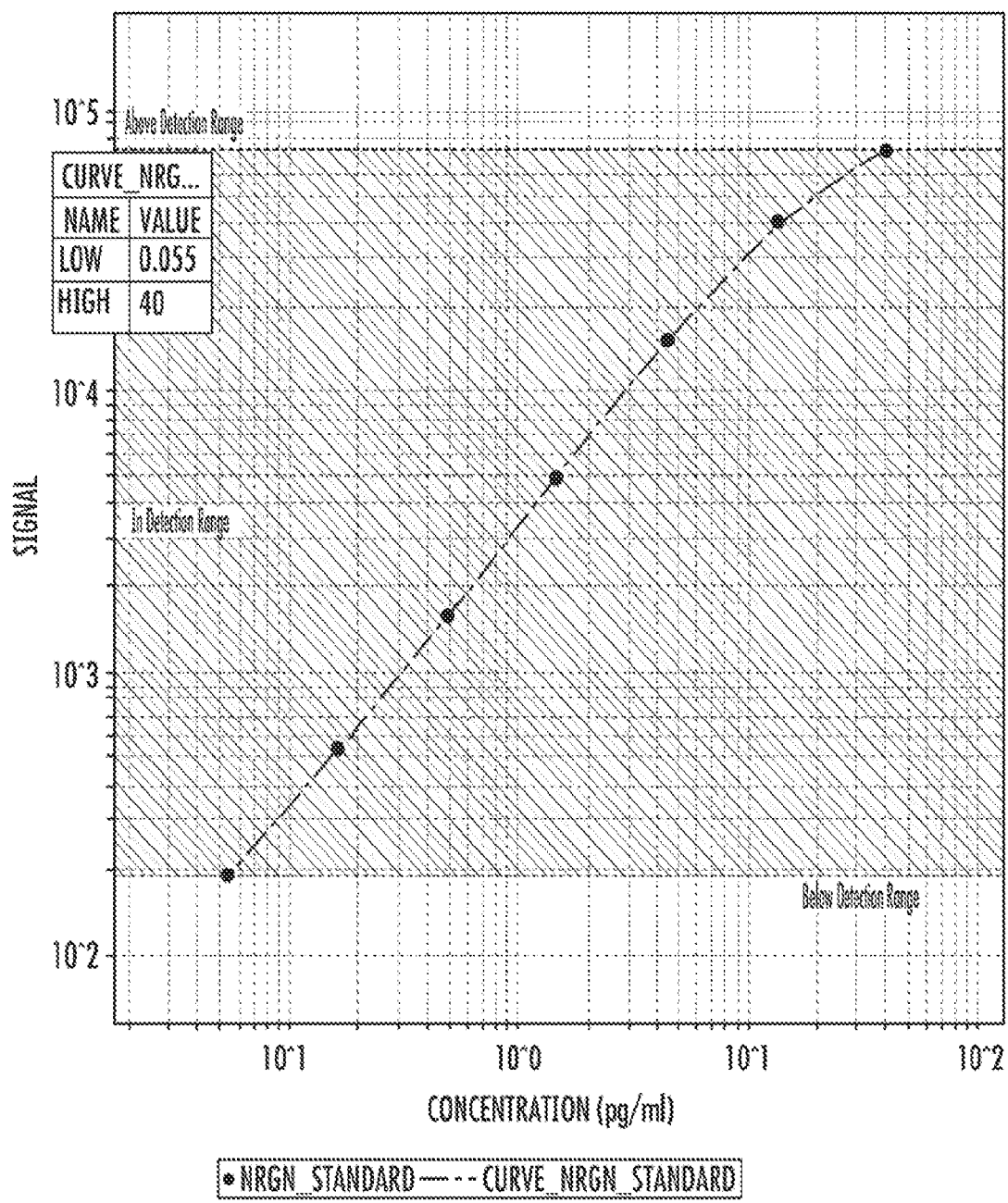
FIG. 33 shows the standard curve of the direct ELISA for recombinant NRGN using an anti-human monoclonal antibody to neurogranin. The concentration range is 75 ng/ml.

A Neurogranin anti-Human monoclonal antibody (Johns Hopkins) at concentration of 75 ng/well was used as a capture antibody and a rabbit polyclonal to neurogranin (Johns Hopkins) at a concentration of 0.5 µg/ml was used as detection. SULFO-TAG anti rabbit antibody (MSD Cat#R32AB-1) at a concentration of 1 µg/ml was used as a labeled reporter at a concentration of 1 µg/ml. GST_NRGN recombinant protein (Johns Hopkins) was used as a standard at a starting concentration of 20 ng/ml then at 1:2 for 7 dilutions in PBS/1% BSA. PBS/1% BSA was used as blank. The standard curve for this assay is shown in FIG. 33.

Neurogranin is Biomarker of Acute Brain Injury.

Figure 34:
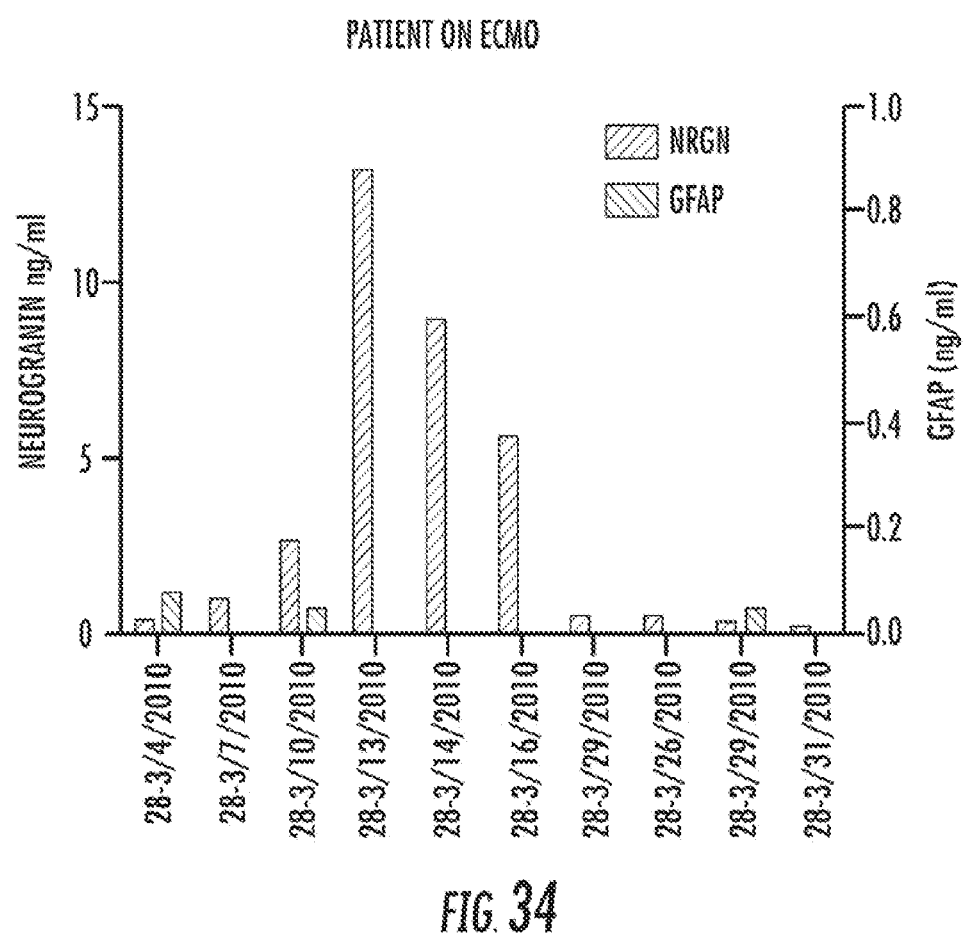
FIG. 34 shows neurogranin and GFAP levels from patients undergoing cardiopulmonary bypass for surgical repair of congenital heart disease.

Using the neurogranin sandwich assay described above, serum samples from an infant on ECMO support for 27 days for cardio-respiratory failure. The infant had normal daily head ultrasounds and at the time of death was thought to not have brain injury. At autopsy, the brain had multiple cortical infarcts they were not diagnosed by ultrasound. As shown in FIG. 34, GFAP levels were unchanged during the entire coarse of ECMO support. However, neurogranin levels increased to a peak 15 fold over baseline over 14 days of ECMO support. As neurogranin is a gray matter, neuronal marker it was more sensitive to cortical gray matter injury than GFAP a marker of white matter injury. This provides evidence that neurogranin is a circulating biomarker of acute cortical brain injury and in combination with GFAP is able to discriminate white matter from gray matter injury to the brain.

We claim:

1. A method of detecting brain injury in a patient, the method comprising the steps of:
   a. contacting a biological sample from the patient with an antibody that specifically binds biomarker glial fibrillary acidic protein (GFAP), an antibody that specifically binds biomarker neurogranin (NRGN) and an antibody that specifically binds one of Astrotactin 1 (ASTN1), Brain Angiogenesis Inhibitor 3 (BAI3), Carnosine Dipeptidase 1 (CNDP1), Ermin (ERMN), Glutamate Receptor Metabotropic 3 (GRM3), Ketch-Like Protein 32 (KLH32), Melanoma Antigen Family E2 (MAGE2), Neuregulin 3 (NRG3), Oligodendrocyte Myelin Glycoprotein (OMG), Solute Carrier Family 39 (zinc transporter) member 12 (SLC39A12), and reticulon 1 (RTN1) in the sample; and
   b. detecting binding of the antibodies to the biomarkers, wherein detection of an increase in the levels of said biomarkers relative to an appropriate control detects brain injury in the patient.

2. The method of claim 1, wherein the biological sample is a blood, plasma, serum, cerebrospinal fluid (CSF), or urine sample.

3. The method of claim 1, wherein the brain injury is subclinical brain injury or traumatic brain injury.

4. A method of detecting traumatic brain injury in a patient,
   the method comprising the steps of:
   a. contacting a blood, serum, or plasma sample from the patient with an antibody that specifically binds biomarker GFAP, an antibody that specifically binds biomarker MT3, an antibody that specifically binds biomarker NRGN, and an antibody selected from the group consisting of antibodies that specifically binds a biomarker of brain injury selected from the group consisting of Astrotactin 1 (ASTN1), Brain Angiogenesis Inhibitor 3 (BAI3), Carnosine Dipeptidase 1 (CNDP1), Ermin (ERMN), Glutamate Receptor Metabotropic 3 (GRM3), Ketch-Like Protein 32 (KLH32), Melanoma Antigen Family E2 (MAGE2), Neuregulin 3 (NRG3), Oligodendrocyte Myelin Glycoprotein (OMG), Solute Carrier Family 39 (zinc transporter) member 12 (SLC39A12) and reticulon 1 (RTN1) in the sample; and b. detecting binding of the antibodies to the biomarkers, wherein detection of said biomarkers relative to an appropriate control detects traumatic brain injury in the patient.

* * * * *

SEQUENCE LISTING

```
<160> NUMBER OF SEQ ID NOS: 8

<210> SEQ ID NO 1
<211> LENGTH: 82
<212> TYPE: DNA
<213> ORGANISM: Artificial Sequence
<220> FEATURE:
<223> OTHER INFORMATION: Single strand DNA oligo pool with 40mer random
      central core.
<220> FEATURE:
<221> NAME/KEY: misc_feature
<222> LOCATION: (26)..(65)
<223> OTHER INFORMATION: n is a, c, g, or t

<400> SEQUENCE: 1
tctcggatcc tcagcgagtc gtctgnnnnn nnnnnnnnnn nnnnnnnnnn nnnnnnnnnn      60
nnnnnccgca tcgtcctccc ta                                              82

<210> SEQ ID NO 2
<211> LENGTH: 42
<212> TYPE: DNA
<213> ORGANISM: Artificial Sequence
<220> FEATURE:
<223> OTHER INFORMATION: Sel2 5' primer containing a T7 promoter for in
      vitro transcription.

<400> SEQUENCE: 2
gggggaattc taatacgact cactataggg aggacgatgc gg                        42

<210> SEQ ID NO 3
<211> LENGTH: 23
<212> TYPE: DNA
<213> ORGANISM: Artificial Sequence
<220> FEATURE:
<223> OTHER INFORMATION: Sel2 3' primer.

<400> SEQUENCE: 3
tctcggatcc tcagcgagtc gtc                                             23

<210> SEQ ID NO 4
```

```
-continued

<211> LENGTH: 40
<212> TYPE: DNA
<213> ORGANISM: Homo sapiens

<400> SEQUENCE: 4
tctaacgcct cccgtatgtt ttccttttc cattgcggat                40

<210> SEQ ID NO 5
<211> LENGTH: 40
<212> TYPE: DNA
<213> ORGANISM: Homo sapiens

<400> SEQUENCE: 5
tctaacgcct cccgcatgtt ttccttttc cattgcggat                40

<210> SEQ ID NO 6
<211> LENGTH: 43
<212> TYPE: DNA
<213> ORGANISM: Homo sapiens

<400> SEQUENCE: 6
ttttcatttt cattttttc caaatcgatc cgccggacct tat            43

<210> SEQ ID NO 7
<211> LENGTH: 14
<212> TYPE: PRT
<213> ORGANISM: Homo sapiens

<400> SEQUENCE: 7

Gly Pro Gly Pro Gly Gly Pro Gly Gly Ala Gly Val Ala Arg
1               5                   10

<210> SEQ ID NO 8
<211> LENGTH: 15
<212> TYPE: PRT
<213> ORGANISM: Homo sapiens

<400> SEQUENCE: 8

Lys Gly Pro Gly Pro Gly Gly Pro Gly Gly Ala Gly Val Ala Arg
1               5                   10                  15
```